US008985103B2

(12) United States Patent
Thoe et al.

(10) Patent No.: US 8,985,103 B2
(45) Date of Patent: *Mar. 24, 2015

(54) DRY POWDER INHALERS WITH DUAL PIERCING MEMBERS

(71) Applicant: Oriel Therapeutics, Inc., Durham, NC (US)

(72) Inventors: Gerald A. Thoe, New Richmond, WI (US); James G. Skakoon, Saint Paul, MN (US); David A. Schuelke, Hudson, WI (US); Thomas W. Ruckdeschel, Cary, NC (US); David Harris, Milton (GB); Scott Alexander Lewis, Cambridge (GB); Andrew Murray Gow, Fen Ditton (GB); Jonathan David Tuckwell, Cambridge (GB)

(73) Assignee: Oriel Therapeutics, Inc., Durham, NC (US)

( * ) Notice: Subject to any disclaimer, the term of this patent is extended or adjusted under 35 U.S.C. 154(b) by 85 days.

This patent is subject to a terminal disclaimer.

(21) Appl. No.: 13/744,923

(22) Filed: Jan. 18, 2013

(65) Prior Publication Data
US 2013/0133653 A1    May 30, 2013

Related U.S. Application Data

(63) Continuation of application No. 12/566,724, filed on Sep. 25, 2009, now Pat. No. 8,381,721.

(60) Provisional application No. 61/170,801, filed on Apr. 20, 2009, provisional application No. 61/100,482, filed on Sep. 26, 2008, provisional application No. 61/148,520, filed on Jan. 30, 2009.

(51) Int. Cl.
*A61M 15/00* (2006.01)

(52) U.S. Cl.
CPC ....... *A61M 15/0045* (2013.01); *A61M 15/0026* (2013.01); *A61M 15/0033* (2013.01); *A61M 15/0075* (2013.01)
USPC ............. 128/203.21; 128/203.12; 128/203.15

(58) Field of Classification Search
CPC ..................... A61M 15/0045; A61M 15/0048; A61M 15/0026; A61M 15/0075; A61M 2202/064; A61M 15/0041; A61M 15/0033; A61M 11/02; A61M 15/0003; A61M 15/001; A61M 15/0036; A61M 15/0043; A61M 15/005
USPC ............ 128/200.11–200.24, 203.12, 203.15, 128/203.19, 203.21; 224/196; 206/3, 533; 131/329

See application file for complete search history.

(56) References Cited

U.S. PATENT DOCUMENTS

| 2,828,005 | A | 3/1958 | Ricke |
| 4,307,734 | A | 12/1981 | Blankenship |

(Continued)

FOREIGN PATENT DOCUMENTS

| DE | 195 00 764 A1 | 7/1996 |
| EP | 1106196 | 3/2001 |

(Continued)

OTHER PUBLICATIONS

Australian Office Action Corresponding to Australian Patent Application No. 2009296535; Date of Issue: Mar. 1, 2013; 3 Pages.

(Continued)

*Primary Examiner* — Annette Dixon
(74) *Attorney, Agent, or Firm* — Myers Bigley Sibley & Sajovec

(57) ABSTRACT

A dry powder inhaler includes a dose container assembly having a dose container disk with opposing upper and lower surfaces, a first row of circumferentially spaced apart dose containers at a first radius and a second row of circumferentially spaced apart dose containers at a second radius. The dose containers have dry powder therein and are sealed via a first flexible sealant over apertures in the upper surface and a second flexible sealant over apertures in the lower surface. A piercing mechanism includes two reciprocating piercers that serially alternate between the two rows of dose containers in the dose container disk. A rotatable ramp disk includes first and second sets of circumferentially spaced-apart ramp elements in staggered, concentric relationship that are configured to move the first and second piercing members between retracted and extended positions.

20 Claims, 42 Drawing Sheets

(56) References Cited

U.S. PATENT DOCUMENTS

| | | | |
|---|---|---|---|
| 4,627,432 A | 12/1986 | Newell et al. |
| 4,778,054 A | 10/1988 | Newell et al. |
| 4,811,731 A | 3/1989 | Newell et al. |
| 5,035,237 A | 7/1991 | Newell et al. |
| 5,138,138 A | 8/1992 | Theilacker et al. |
| 5,327,883 A | 7/1994 | Williams et al. |
| 5,337,740 A | 8/1994 | Armstrong et al. |
| 5,388,572 A | 2/1995 | Mulhauser et al. |
| 5,394,868 A | 3/1995 | Ambrosio et al. |
| 5,529,059 A | 6/1996 | Armstrong et al. |
| 5,533,502 A | 7/1996 | Piper |
| 5,590,645 A | 1/1997 | Davies et al. |
| 5,622,166 A | 4/1997 | Eisele et al. |
| 5,634,900 A | 6/1997 | Makino et al. |
| 5,715,810 A | 2/1998 | Armstrong et al. |
| 5,727,607 A | 3/1998 | Ichikawa et al. |
| 5,769,073 A | 6/1998 | Eason et al. |
| 5,860,419 A | 1/1999 | Davies et al. |
| 5,873,360 A | 2/1999 | Davies et al. |
| 5,909,829 A | 6/1999 | Wegman et al. |
| 5,921,237 A | 7/1999 | Eisele et al. |
| 5,947,169 A | 9/1999 | Wegman et al. |
| 6,029,663 A | 2/2000 | Eisele et al. |
| 6,032,666 A | 3/2000 | Davies et al. |
| 6,082,356 A | 7/2000 | Stradella |
| 6,116,237 A | 9/2000 | Schultz et al. |
| 6,116,238 A | 9/2000 | Jackson et al. |
| 6,245,339 B1 | 6/2001 | Van Oort et al. |
| 6,328,033 B1 | 12/2001 | Avrahmi |
| 6,367,473 B1 | 4/2002 | Käfer |
| 6,378,519 B1 | 4/2002 | Davies et al. |
| 6,445,941 B1 | 9/2002 | Hampton et al. |
| 6,536,427 B2 | 3/2003 | Davies et al. |
| 6,543,448 B1 | 4/2003 | Smith et al. |
| 6,550,477 B1 | 4/2003 | Casper et al. |
| 6,591,832 B1 | 7/2003 | DeJonge |
| 6,655,381 B2 | 12/2003 | Keane et al. |
| 6,668,827 B2 | 12/2003 | Schuler et al. |
| 6,679,254 B1 | 1/2004 | Rand et al. |
| 6,792,945 B2 | 9/2004 | Davies et al. |
| 6,810,872 B1 | 11/2004 | Ohki et al. |
| 6,871,647 B2 | 3/2005 | Allan et al. |
| 6,880,555 B1 | 4/2005 | Brunnberg |
| 6,889,690 B2 | 5/2005 | Crowder et al. |
| 6,915,802 B1 | 7/2005 | Anderson et al. |
| 6,923,178 B2 | 8/2005 | Snow |
| 6,948,494 B1 | 9/2005 | Snow |
| 7,089,935 B1 | 8/2006 | Rand |
| 7,219,665 B1 | 5/2007 | Braithwaite |
| 7,225,808 B2 | 6/2007 | Davies et al. |
| 7,275,538 B2 | 10/2007 | Nakamura et al. |
| 7,318,436 B2 | 1/2008 | Snow |
| 7,389,775 B2 | 6/2008 | Davies et al. |
| 7,503,324 B2 | 3/2009 | Barney et al. |
| 7,571,723 B2 | 8/2009 | Braithwaite |
| 7,571,724 B2 | 8/2009 | Braithwaite |
| 7,669,597 B2 | 3/2010 | Sullivan et al. |
| 8,381,721 B2 * | 2/2013 | Thoe et al. | 128/203.21 |
| 8,550,071 B2 * | 10/2013 | Striebig et al. | 128/203.15 |
| 2001/0007853 A1 | 7/2001 | Dimarchi et al. |
| 2001/0053761 A1 | 12/2001 | Dimarchi et al. |
| 2002/0040713 A1 | 4/2002 | Eisele et al. |
| 2002/0170560 A1 | 11/2002 | Young et al. |
| 2003/0178024 A1 | 9/2003 | Allan et al. |
| 2004/0025877 A1 | 2/2004 | Crowder et al. |
| 2005/0056281 A1 | 3/2005 | Snow |
| 2005/0126568 A1 | 6/2005 | Davies et al. |
| 2005/0154491 A1 | 7/2005 | Anderson et al. |
| 2005/0161041 A1 | 7/2005 | Schuler et al. |
| 2005/0172963 A1 | 8/2005 | Allan et al. |
| 2006/0102511 A1 | 5/2006 | Pasbrig et al. |
| 2006/0157053 A1 | 7/2006 | Barney et al. |
| 2007/0062525 A1 | 3/2007 | Bonney et al. |
| 2007/0137643 A1 | 6/2007 | Bonney et al. |
| 2007/0137645 A1 | 6/2007 | Eason et al. |
| 2007/0181123 A1 | 8/2007 | Houzego |
| 2007/0181124 A1 | 8/2007 | Casper et al. |
| 2007/0215149 A1 | 9/2007 | King et al. |
| 2007/0221218 A1 | 9/2007 | Warden et al. |
| 2007/0235029 A1 | 10/2007 | Zhu et al. |
| 2008/0001008 A1 | 1/2008 | Thoemmes et al. |
| 2008/0127971 A1 | 6/2008 | King et al. |
| 2008/0223366 A1 | 9/2008 | Davies et al. |
| 2009/0114220 A1 | 5/2009 | Wachtel et al. |
| 2009/0139516 A1 | 6/2009 | Augustyn et al. |
| 2009/0194105 A1 | 8/2009 | Besseler et al. |
| 2010/0078022 A1 | 4/2010 | Striebig et al. |
| 2010/0163042 A1 | 7/2010 | Bhowmick et al. |
| 2011/0162648 A1 | 7/2011 | Ruckdeschel |

FOREIGN PATENT DOCUMENTS

| | | |
|---|---|---|
| EP | 1 779 884 A1 | 5/2007 |
| EP | 1844805 | 10/2007 |
| GB | 873410 A | 7/1961 |
| GB | 2 246 299 A | 1/1992 |
| GB | 2340758 | 3/2000 |
| JP | 2002-536080 | 10/2002 |
| JP | 2003-512102 A | 4/2003 |
| JP | 2004-527271 A | 9/2004 |
| JP | 2007-520247 A | 7/2007 |
| WO | WO 94/14490 | 7/1994 |
| WO | WO 94/20164 | 9/1994 |
| WO | WO 98/41265 | 9/1998 |
| WO | WO 99/36116 | 7/1999 |
| WO | WO 00/45879 | 8/2000 |
| WO | WO 00/45879 A1 | 8/2000 |
| WO | WO 01/17595 A1 | 3/2001 |
| WO | WO 01/28616 | 4/2001 |
| WO | WO 01/34234 | 5/2001 |
| WO | WO 02/053215 | 7/2002 |
| WO | WO 02/053215 A2 | 7/2002 |
| WO | WO 02/053216 | 7/2002 |
| WO | WO 03/011708 | 2/2003 |
| WO | WO 2004/045487 | 6/2004 |
| WO | WO 2004/045487 A2 | 6/2004 |
| WO | WO 2005/002654 | 1/2005 |
| WO | WO 2005/037353 | 4/2005 |
| WO | WO 2005/044173 A1 | 5/2005 |
| WO | WO 2005/110519 | 11/2005 |
| WO | WO 2006/031775 | 3/2006 |
| WO | WO 2006/108877 | 10/2006 |
| WO | WO 2007/007110 | 1/2007 |
| WO | WO 2007/012871 | 2/2007 |
| WO | WO 2007/118648 A1 | 10/2007 |
| WO | WO 2008/039182 A1 | 4/2008 |
| WO | WO 2010/036355 A2 | 4/2010 |
| WO | WO 2010/036839 A2 | 4/2010 |

OTHER PUBLICATIONS

Japanese Office Action Corresponding to Japanese Patent Application No. 2011-529238; Dispatch Date: Mar. 1, 2013; 3 Pages (Foreign Text Only).

JP Office action corresponding to Japanese Patent Application No. 2011-530042; Dispatch Date: Aug. 16, 2013; 3 pages.

JP Office action corresponding to Japanese Patent Application No. 2011-529237; Dispatch Date: Aug. 16, 2013; 4 pages.

Australian Examination Report Corresponding to Australian Patent Application No. 2009296538; Date of Issue: Oct. 19, 2012; 4 Pages.

European Search Report Corresponding to European Application No. 09 816 585.5; Dated: Feb. 1, 2012; 8 pages.

Extended European Search Report including the Supplementary European Search Report and the European Search Opinion corresponding to European Application No. 09818090.4; Mailing Date: Mar. 21, 2012; 5 pages.

Hickey et al., A new millennium for inhaler technology, 21 Pharm. Tech., n. 6, pp. 116-125 (1997).

International Search Report and Written Opinion for corresponding PCT application No. PCT/US2009/058285, date of mailing Apr. 14, 2010.

(56) References Cited

OTHER PUBLICATIONS

International Search Report and Written Opinion for corresponding PCT Application No. PCT/US2009/005321, date of mailing Mar. 29, 2010.
Notification of Transmittal of the International Search Report and the Written Opinion of the International Searching Authority, or the Declaration issued by the European Patent Office on Jan. 7, 2010 for the corresponding International Application No. PCT/US2009/058281.
Notification of Transmittal of the International Search Report and the Written Opinion of the International Searching Authority issued May 14, 2010 by the Korean Intellectual Property Office for PCT Application No. PCT/US2009/005338.
Notification of Transmittal of the International Search Report and the Written Opinion of the International Searching Authority issued May 4, 2010 by the Korean Intellectual Property Office for corresponding PCT Application No. PCT/US20098/005336.
PCT Invitation to Pay Additional Fees and Partial Search for corresponding PCT Application No. PCT/US2009/058285, Date of Mailing Dec. 30, 2009.
Prime et al., Review of Dry Powder Inhalers, 26 Adv. Drug Delivery Rev., pp. 51-58 (1997).
Wolff et al., Generation of Aerosolized Drugs, J. Aerosol. Med., pp. 88-106 (1994).
JP Office action corresponding to Japanese Patent Application No. 2011-529238; Dispatch Date: Nov. 29, 2013; 3 pages.

\* cited by examiner

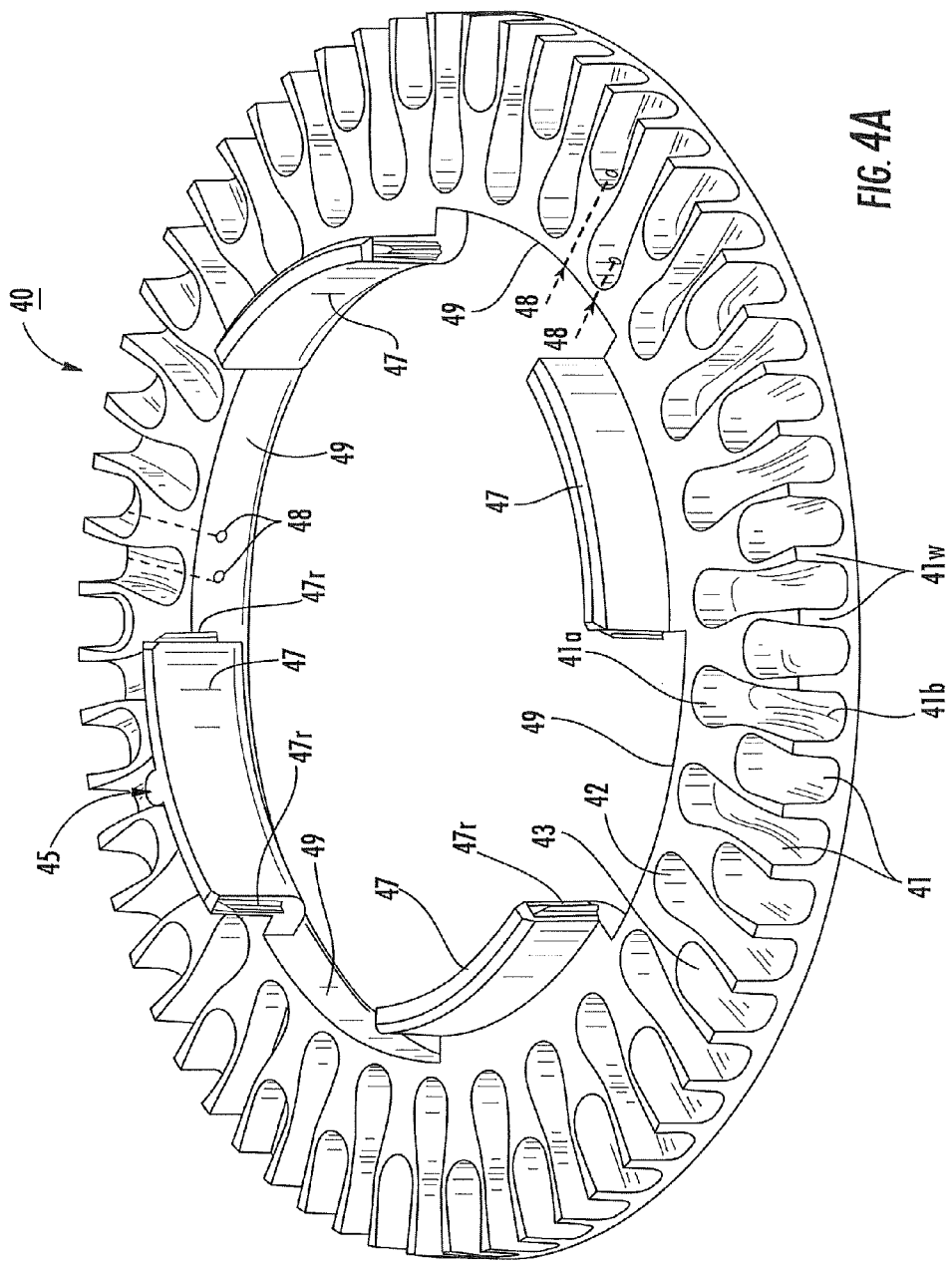

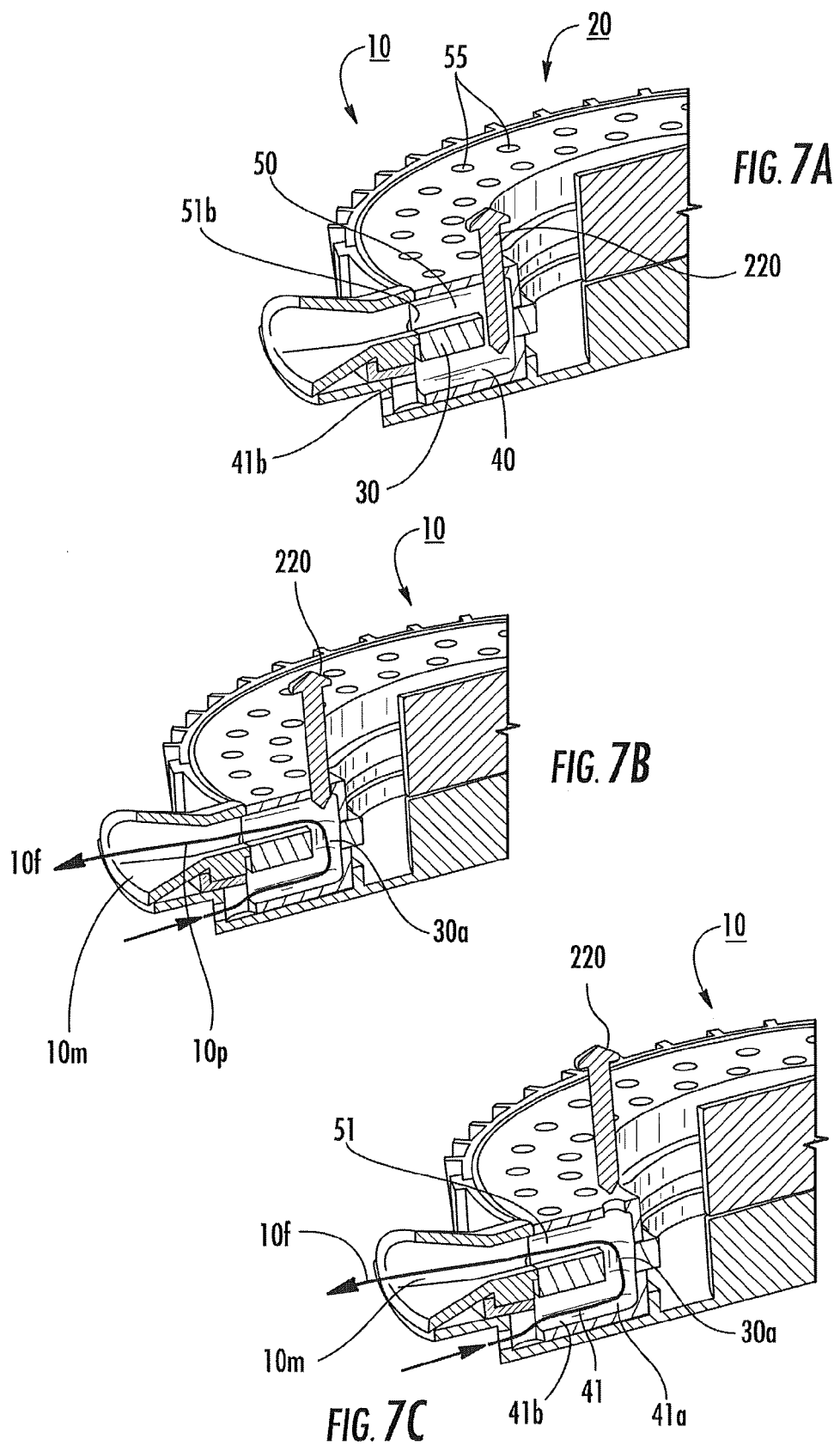

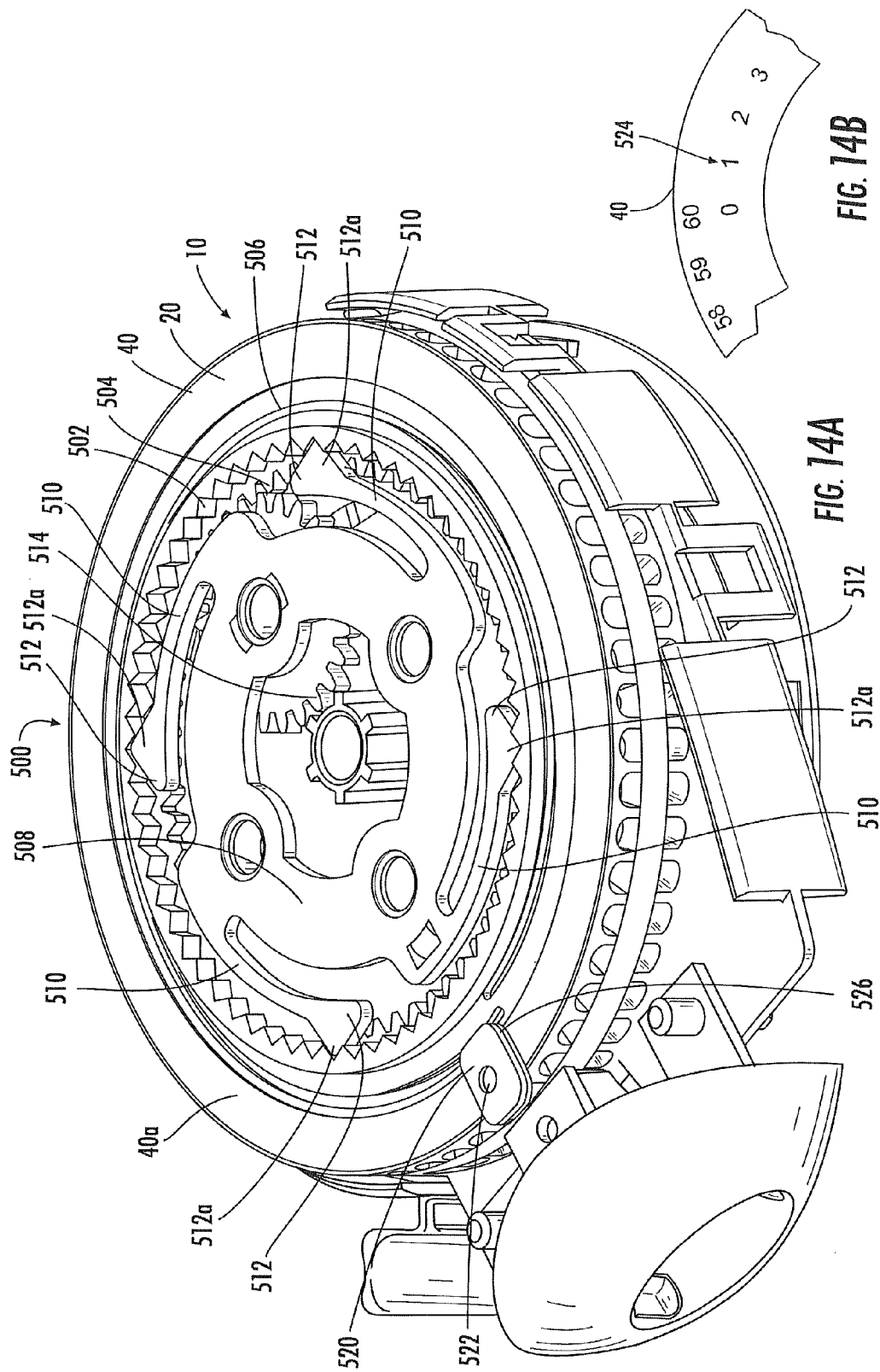

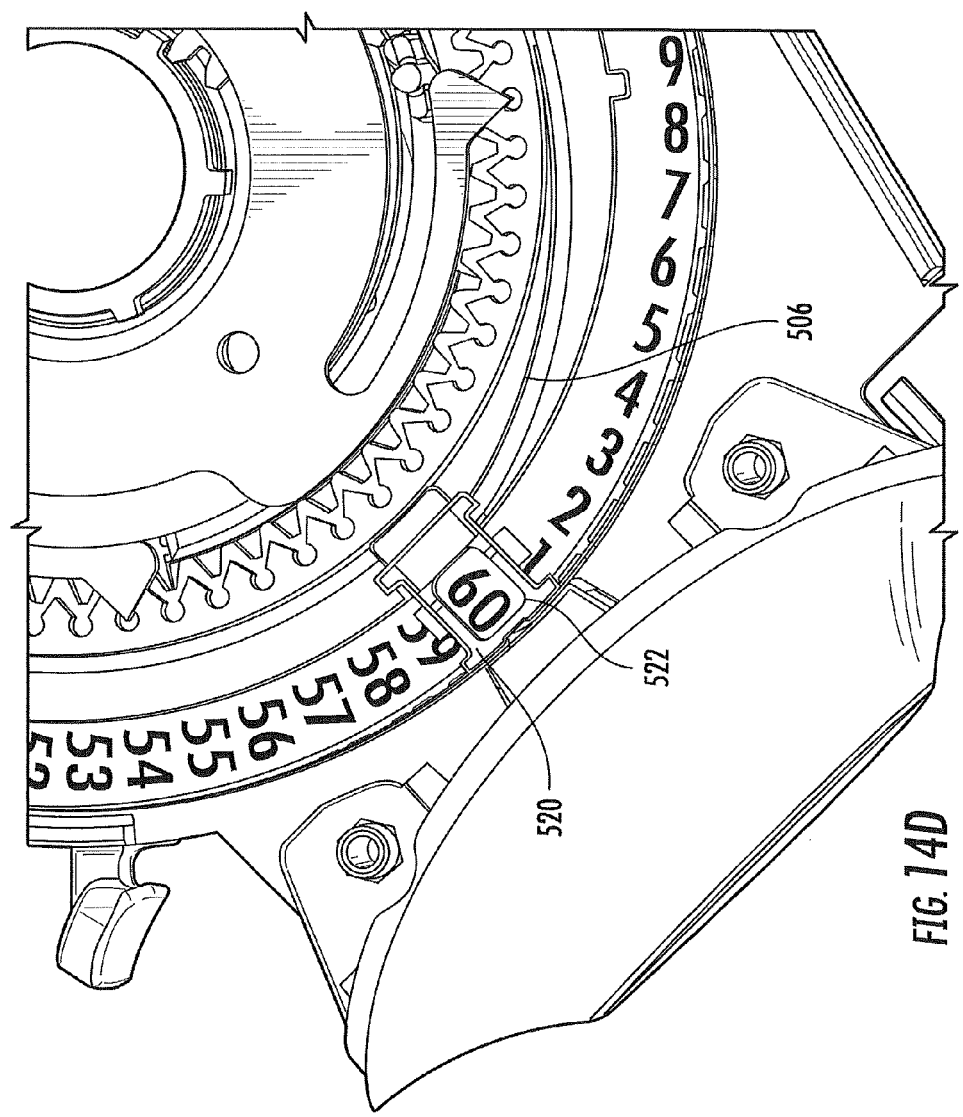

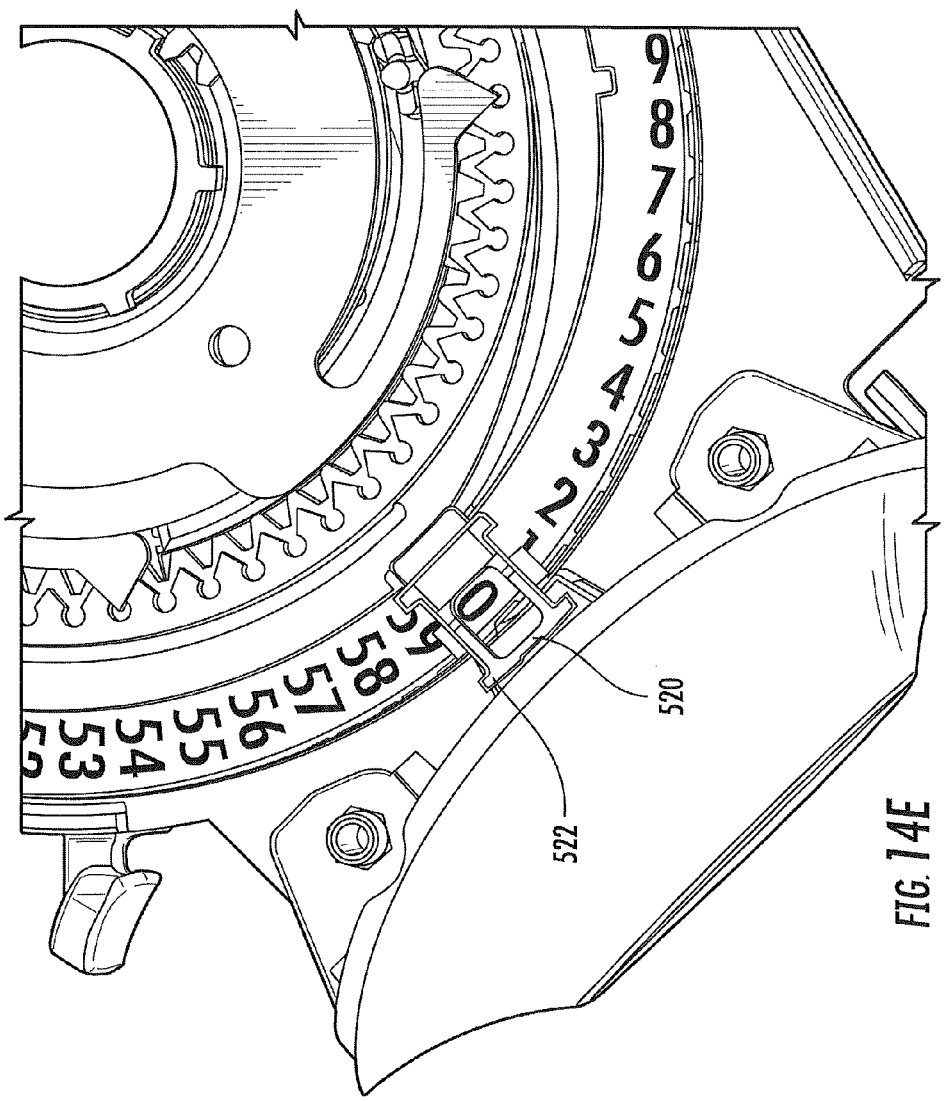

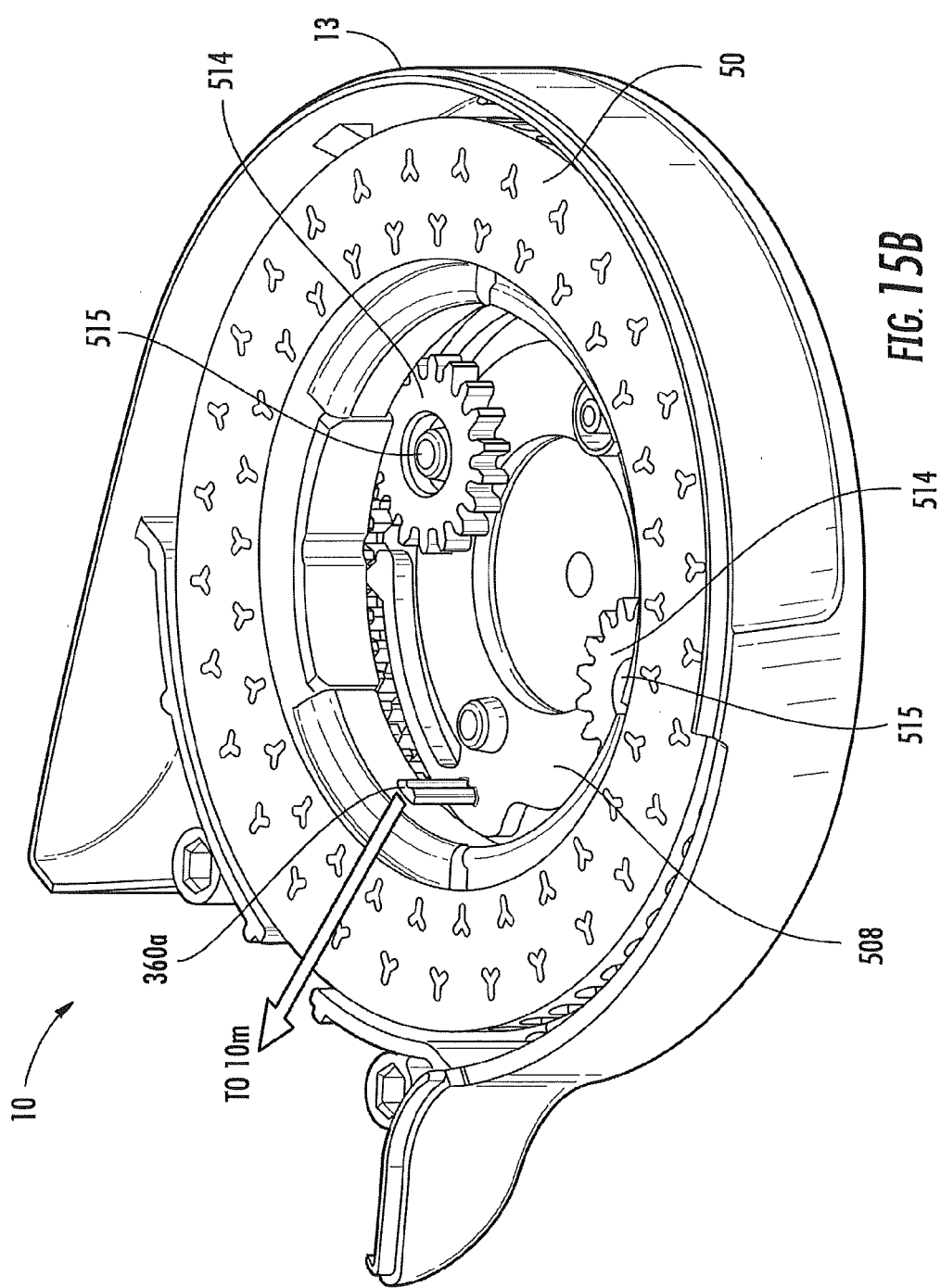

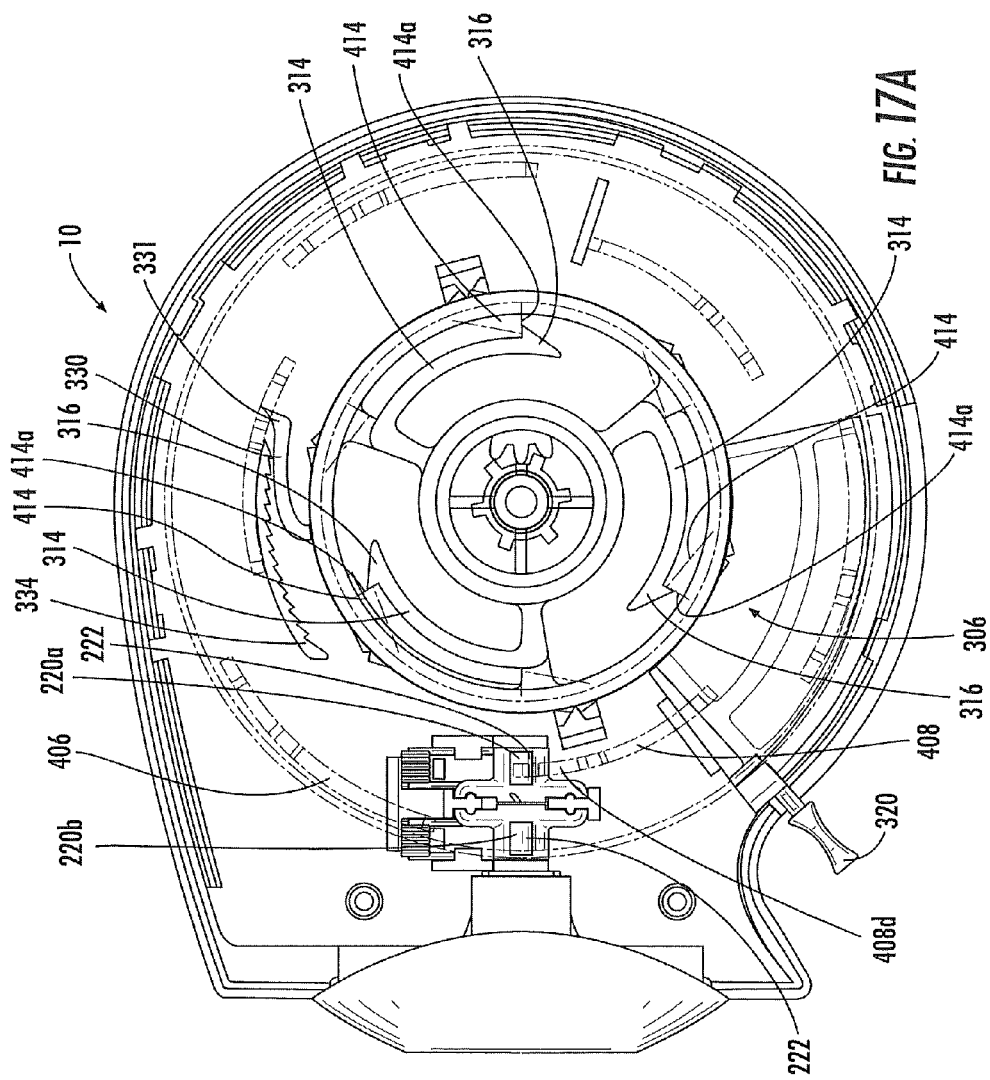

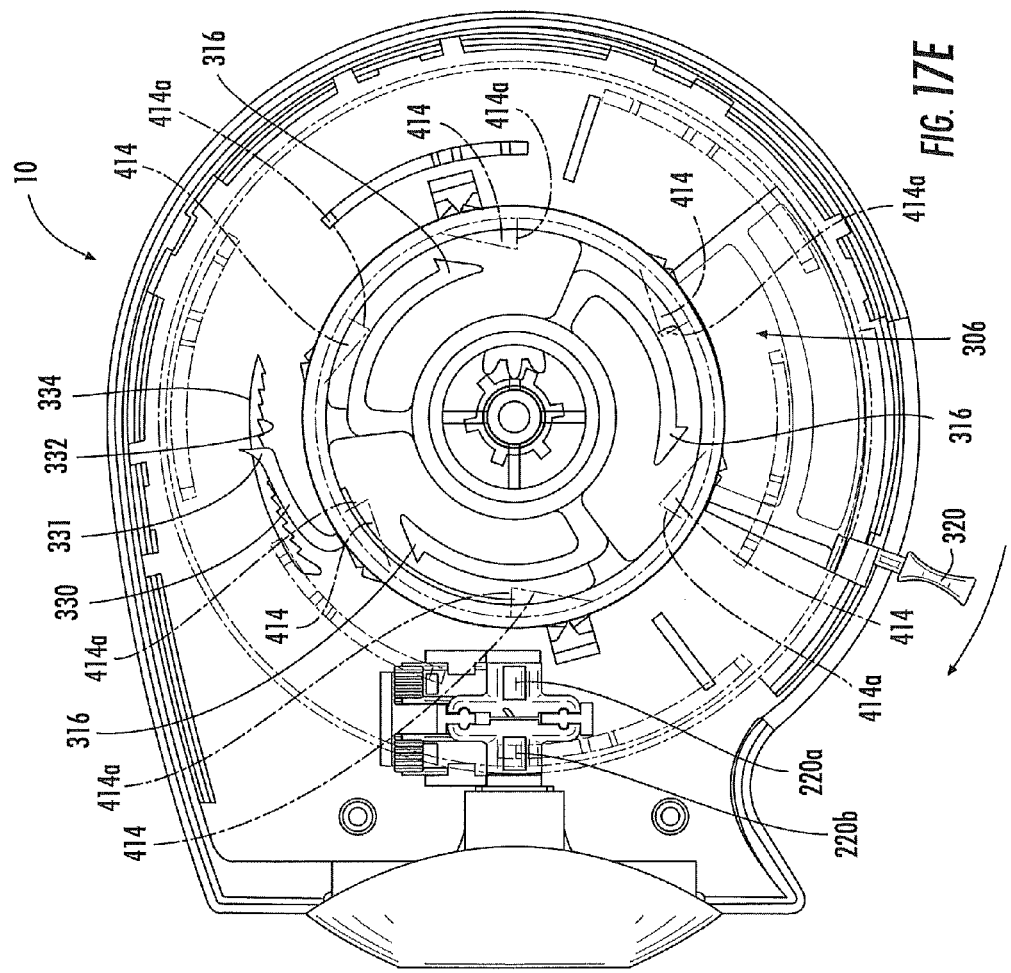

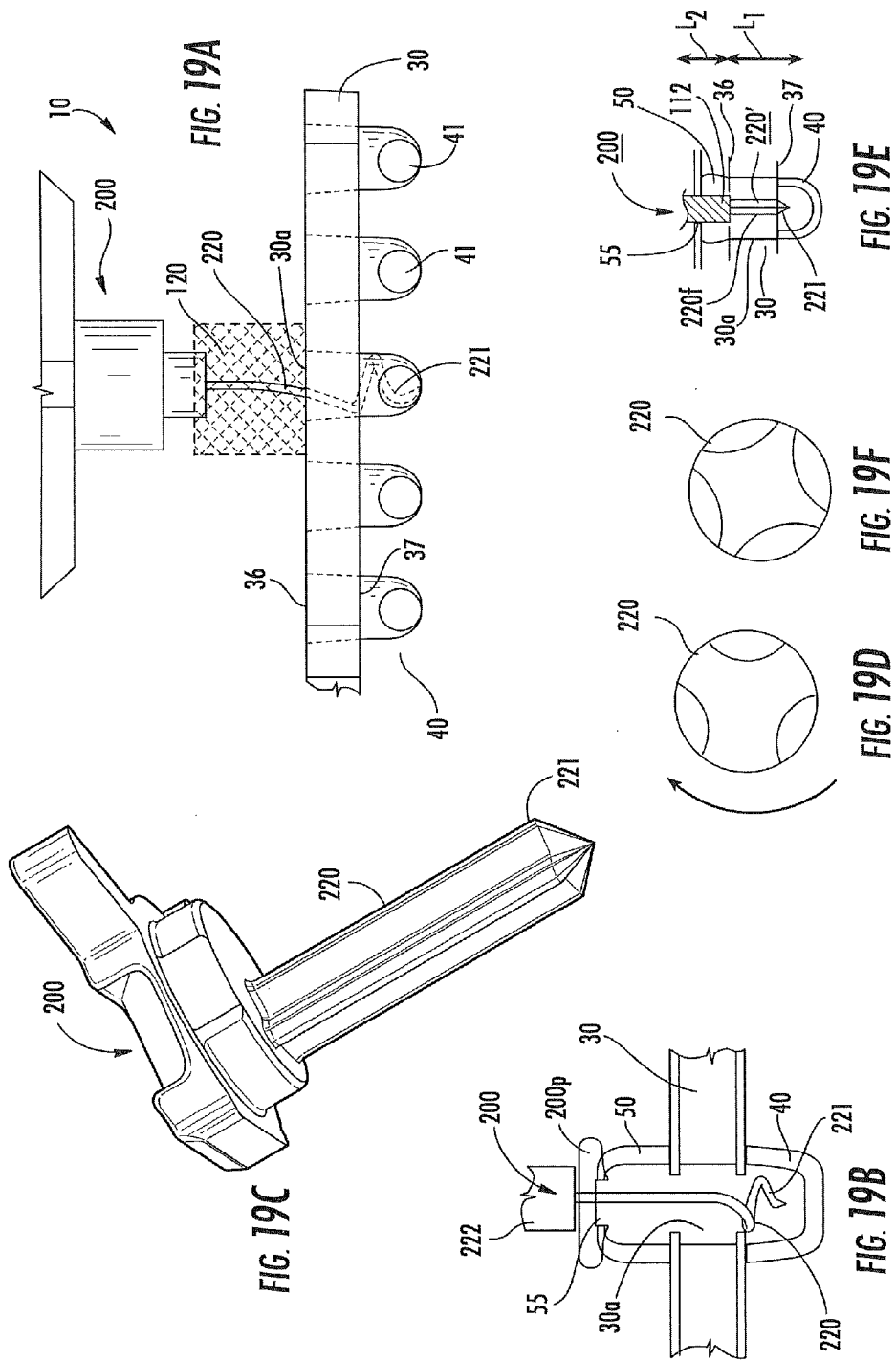

DRY POWDER INHALERS WITH DUAL PIERCING MEMBERS

RELATED APPLICATIONS

This application is a continuation application of U.S. patent application Ser. No. 12/566,724, filed Sep. 25, 2009, now U.S. Pat. No. 8,381,721, which claims the benefit of and priority to U.S. Provisional Patent Application No. 61/170,801, filed Apr. 20, 2009; U.S. Provisional Patent Application No. 61/100,482, filed Sep. 26, 2008; and U.S. Provisional Patent Application No. 61/148,520, filed Jan. 30, 2009, the disclosures of which are incorporated herein by reference as if set forth in their entireties.

FIELD OF THE INVENTION

The present invention relates to inhalers, and may be particularly suitable for dry powder inhalers.

BACKGROUND

Dry powder inhalers (DPIs) are an alternative to pMDI (pressurized metered dose inhaler) devices for delivering drug aerosols without using propellants. Typically, DPIs are configured to deliver a powdered drug or drug mixture that includes an excipient and/or other ingredients. Generally described, known single and multiple dose dry powder DPI devices use: (a) individual pre-measured doses in blisters containing the drug, which can be inserted into the device prior to dispensing; or (b) bulk powder reservoirs which are configured to administer successive quantities of the drug to the patient via a dispensing chamber which dispenses the proper dose.

In operation, DPI devices strive to administer a uniform aerosol dispersion amount in a desired physical form of the dry powder (such as a particulate size or sizes) into a patient's airway and direct it to a desired internal deposit site(s).

There remains a need for alternative inhalers and/or dose containment devices that can be used to deliver medicaments.

SUMMARY

Embodiments of the present invention provide dry powder inhalers with reciprocating inner and outer piercing mechanisms that facilitate the use of dose rings or disks having dose containers arranged in concentric rows. According to some embodiments, a dry powder inhaler includes a dose container disk having a plurality of circumferentially spaced apart dry powder dose containers arranged in first and second concentric rows of different radius, and a piercing mechanism that is configured to sequentially open a dry powder dose container on the first row then open a dry powder dose container on the second row. The piercing mechanism includes first and second elongate piercing members in adjacent radially spaced-apart relationship. Each piercing member is capable of reciprocal movement between piercing and non-piercing positions, and includes a distal piercing portion and a proximal head portion. The first piercing member is configured to pierce the sealant of a dose container in the first row, and the second piercing member is configured to pierce the sealant of a dose container in the second row.

According to some embodiments, a dry powder inhaler includes a dose container disk having opposing upper and lower primary surfaces, a first row of circumferentially spaced apart dose containers at a first radius and a second row of circumferentially spaced apart dose containers at a second radius so that the first and second rows are concentric with respect to a center of the disk. The dose containers have dry powder therein. A first flexible sealant resides over apertures in the upper surface, and a second flexible sealant resides over apertures in the lower surface to contain the powder within the dose containers.

A piercing mechanism is operably associated with the dose container disk and is configured to pierce the first and second sealants that seal a dose container. The piercing mechanism includes two reciprocating piercers that serially alternate between the two rows of dose containers in the dose container disk. Each elongate piercing member is extended and retracted to pierce the first and second sealants of a dose container in a respective row. Each elongate piercing member includes a distal piercing portion and a proximal head portion. In some embodiments, the distal piercing portion can be a solid piercer configured to pierce the sealants. In some embodiments, the distal piercing portion can be a corkscrew piercer configured to pierce the sealants with a straight vertical non-rotational movement. In some embodiments, the distal piercing portion can have a fluted piercer, for example with three or four lobes, that is configured to pierce the sealants.

Each elongate piercing member is capable of reciprocal movement between piercing and non-piercing positions. In the piercing position, the piercing member distal piercing portion extends through the first and second sealants of a dose container. In a retracted position, the distal piercing portion is retracted above a dose container, such that the dose container is free to rotate. A biasing member is configured to urge each of the piercing members toward retracted positions.

A rotatable ramp disk includes first and second sets of circumferentially spaced-apart ramp elements in staggered, concentric relationship. The ramp disk rotates only in one direction, and is driven by an actuator mechanism, which is moved forward by the user, and returned backward by the user action of closing the mouthpiece cover of the inhaler. When the ramp disk is rotated as a result of the user moving the actuator mechanism, the first set of ramp elements are configured to move the first piercing member between retracted and extended positions, and the second set of ramp elements are configured to move the second piercing member between retracted and extended positions. The ramp elements are staggered such that piercing alternates between dose containers in the first and second rows. Each ramp element in the first and second sets includes a first inclined portion, a plateau portion, a second inclined portion, and a shelf portion.

The actuator mechanism is movable between first and second positions by a user. Movement of the actuator from the first position to the second position causes the ramp disk to rotate such that a ramp element in the first set causes the first piercing member to pierce the sealants over and under a dose container in the first row. Subsequent movement of the actuator from the first position to the second position (i.e., the next time the inhaler is used) causes the ramp disk to rotate such that a ramp element in the second set causes the second piercing member to pierce the sealants over and under a dose container in the second row. This alternating piercing scheme is repeated as the inhaler is used. In some embodiments, movement of the actuator from the first position to the second position causes a piercing member to pierce the sealants over and under a dose container, and then partially retract therefrom.

Inhalers, according to embodiments of the present invention have numerous advantages over conventional inhalers. For example, the use of two piercing members takes away the need to tightly control the position and actions of a single, moving piercer. Moreover, by using two piercing members, wear can be significantly reduced for each piercing member. As such, a less expensive material may be utilized for the piercing members than may otherwise be necessary if only a single piercing member were to be utilized. In addition, the configuration of the two piercing members allows more flexibility for the design of a spring used to urge the piercing members to a retracted position. For example, the spring is not required to be positioned under the piercing members. As such, inhaler devices with less height requirements than conventional inhaler devices can be achieved.

Other advantages of inhaler devices according to embodiments of the present invention is provided by the use of a separate ramp disk and actuator mechanism. Because indexing of a dose container assembly is driven by the ramp disk, the indexing mechanism can be moved to the interior of the inhaler where more space is available, thereby helping to reduce the overall size of the inhaler. Because the ramp disk and actuator mechanism are separate components, the material selection of each can be optimized. For example, material with better friction properties can be selected for the ramp disk, and materials with strength and cosmetic features can be selected for the actuator mechanism.

It is noted that aspects of the invention described with respect to one embodiment may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIG. 4A is a greatly enlarged top perspective view of a lower airway disk according to some embodiments of the present invention.

FIGS. 7A-7C are partial cutaway views of a dose container assembly in an inhaler cooperating with a piercing mechanism having a three-stage operation sequence according to some embodiments of the present invention.

FIG. 14A is a bottom, cutaway perspective view of the inhaler of FIG. 10A illustrating the dose disk indexing mechanism, according to some embodiments of the present invention.

FIG. 14B is a partial plan view of the lower disk of the dose container assembly and illustrating dose indicia thereon, according to some embodiments of the present invention.

FIG. 14D is an enlarged, partial plan view of the inhaler of FIG. 14C illustrating the window aperture centered over dose indicia that indicates that 60 doses are remaining.

FIG. 14E is an enlarged, partial plan view of the inhaler of FIG. 14C illustrating the window aperture centered over dose indicia that indicates that no (zero) doses are remaining.

FIG. 15B is a top, cutaway perspective view of the inhaler of FIG. 10B illustrating the dose disk indexing mechanism in relation to a dose container assembly, according to some embodiments of the present invention.

FIGS. 17A-17E are top, cutaway views, with partial transparent layers or members/disks for clarity, of the inhaler of FIG. 10A that illustrate an exemplary sequence of operations thereof, according to some embodiments of the present invention.

FIG. 19A is an enlarged partial section view of a piercing member according to some embodiments of the present invention.

FIG. 19B is an enlarged partial section view of a piercing member similar to that shown in FIG. 19A, according to some embodiments of the present invention.

FIG. 19C is a partial front schematic view of a piercing member with a fluted configuration, according to some embodiments of the present invention.

FIG. 19D is an end view of the device shown in FIG. 19C.

FIG. 19E is a partial front schematic view of another fluted piercer configuration according to some embodiments of the present invention.

FIG. 19F is an end view of an exemplary four lobe fluted piercer, according to some embodiments of the present invention.

DETAILED DESCRIPTION

Figure 1A:
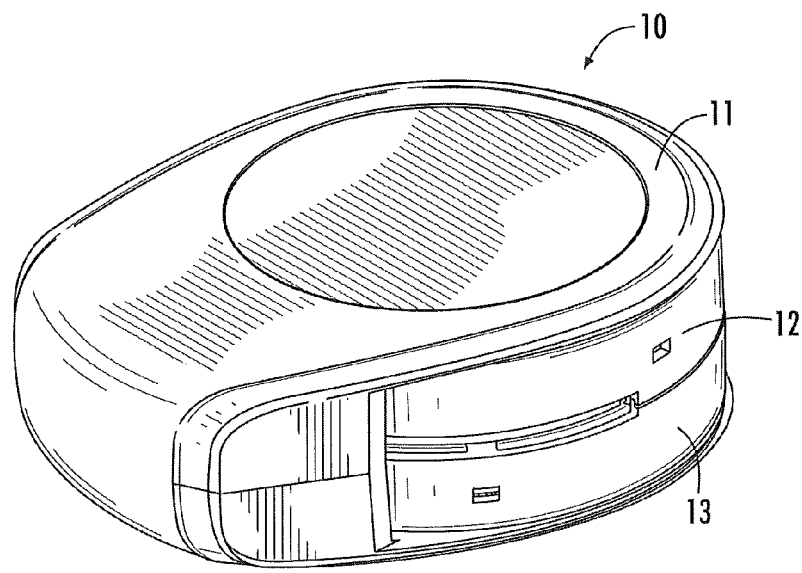
FIG. 1A is a front perspective view of an inhaler with a cover, according to some embodiments of the present invention, and where the cover is in a closed position.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. Features described with respect to one figure or embodiment can be associated with another embodiment of figure although not specifically described or shown as such.

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that although the terms first and second are used herein to describe various regions, layers and/or sections, these regions, layers and/or sections should not be limited by these terms. These terms are only used to distinguish one region, layer or section from another region, layer or section. Thus, a first region, layer or section discussed below could be termed a second region, layer or section, and similarly, a second region, layer or section discussed below could be termed a first region, layer or section without departing from the teachings of the present invention. Like numbers refer to like elements throughout.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

In the description of the present invention that follows, certain terms are employed to refer to the positional relationship of certain structures relative to other structures. As used herein, the term "front" or "forward" and derivatives thereof refer to the general or primary direction that the dry powder travels to be dispensed to a patient from a dry powder inhaler; this term is intended to be synonymous with the term "downstream," which is often used in manufacturing or material flow environments to indicate that certain material traveling or being acted upon is farther along in that process than other material. Conversely, the terms "rearward" and "upstream" and derivatives thereof refer to the direction opposite, respectively, the forward or downstream direction. The term "deagglomeration" and its derivatives refer to processing dry powder in the inhaler airflow path to inhibit the dry powder from remaining or becoming agglomerated or cohesive during inspiration.

The inhalers and methods of the present invention may be particularly suitable for holding a partial or bolus dose or doses of one or more types of particulate dry powder substances that are formulated for in vivo inhalant dispersion (using an inhaler) to subjects, including, but not limited to, animal and, typically, human subjects. The inhalers can be used for nasal and/or oral (mouth) respiratory inhalation delivery, but are typically oral inhalers.

The terms "sealant", "sealant layer" and/or "sealant material" includes configurations that have at least one layer of at least one material and can be provided as a continuous layer that covers the entire upper surface and/or lower surface or may be provided as strips or pieces to cover portions of the device, e.g., to reside over at least a target one or more of the dose container apertures. Thus, terms "sealant" and "sealant layer" includes single and multiple layer materials, typically comprising at least one foil layer. The sealant or sealant layer can be a thin multi-layer laminated sealant material with elastomeric and foil materials. The sealant layer can be selected to provide drug stability as they may contact the dry powder in the respective dose containers.

The term "reciprocating" means the piercing members travel up and down to open respective dose containers.

The sealed dose containers can be configured to inhibit oxygen and moisture penetration to provide a sufficient shelf life.

The term "primary surface" refers to a surface that has a greater area than another surface and the primary surface can be substantially planar or may be otherwise configured. For example, a primary surface can include protrusions or recessions, such as where some blister configurations are used. Thus, a disk can have upper and lower primary surfaces and a minor surface (e.g., a wall with a thickness) that extends between and connects the two.

The dry powder substance may include one or more active pharmaceutical constituents as well as biocompatible additives that form the desired formulation or blend. As used herein, the term "dry powder" is used interchangeably with "dry powder formulation" and means that the dry powder can comprise one or a plurality of constituents or ingredients with one or a plurality of (average) particulate size ranges. The term "low-density" dry powder means dry powders having a density of about 0.8 $g/cm^3$ or less. In particular embodiments, the low-density powder may have a density of about 0.5 $g/cm^3$ or less. The dry powder may be a dry powder with cohesive or agglomeration tendencies.

The term "filling" means providing a bolus or sub-bolus metered amount of dry powder. Thus, the respective dose container is not required to be volumetrically full.

In any event, individual dispensable quantities of dry powder formulations can comprise a single ingredient or a plurality of ingredients, whether active or inactive. The inactive ingredients can include additives added to enhance flowability or to facilitate aerosolization delivery to the desired target. The dry powder drug formulations can include active particulate sizes that vary. The device may be particularly suitable for dry powder formulations having particulates which are in the range of between about 0.5-50 μm, typically in the range of between about 0.5 μm-20.0 μm, and more typically in the range of between about 0.5 μm-8.0 μm. The dry powder formulation can also include flow-enhancing ingredients, which typically have particulate sizes that may be larger than the active ingredient particulate sizes. In certain embodiments, the flow-enhancing ingredients can include excipients having particulate sizes on the order of about 50-100 μm. Examples of excipients include lactose and trehalose. Other types of excipients can also be employed, such as, but not limited to, sugars which are approved by the United States Food and Drug Administration ("FDA") as cryoprotectants (e.g., mannitol) or as solubility enhancers (e.g., cyclodextrine) or other generally recognized as safe ("GRAS") excipients.

"Active agent" or "active ingredient" as described herein includes an ingredient, agent, drug, compound, or composition of matter or mixture, which provides some pharmacologic, often beneficial, effect. This includes foods, food supplements, nutrients, drugs, vaccines, vitamins, and other beneficial agents. As used herein, the terms further include any physiologically or pharmacologically active substance that produces a localized and/or systemic effect in a patient.

The active ingredient or agent that can be delivered includes antibiotics, antiviral agents, anepileptics, analgesics, anti-inflammatory agents and bronchodilators, and may be inorganic and/or organic compounds, including, without limitation, drugs which act on the peripheral nerves, adrenergic receptors, cholinergic receptors, the skeletal muscles, the cardiovascular system, smooth muscles, the blood circulatory system, synoptic sites, neuroeffector junctional sites, endocrine and hormone systems, the immunological system, the reproductive system, the skeletal system, autacoid systems, the alimentary and excretory systems, the histamine system, and the central nervous system. Suitable agents may be selected from, for example and without limitation, polysaccharides, steroids, hypnotics and sedatives, psychic energizers, tranquilizers, anticonvulsants, muscle relaxants, anti-Parkinson agents, analgesics, anti-inflammatories, muscle contractants, antimicrobials, antimalarials, hormonal agents including contraceptives, sympathomimetics, polypeptides and/or proteins (capable of eliciting physiological effects), diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.

The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines. Where the active agent is insulin, the term "insulin" includes natural extracted human insulin, recombinantly produced human insulin, insulin extracted from bovine and/or porcine and/or other sources, recombinantly produced porcine, bovine or other suitable donor/extraction insulin and mixtures of any of the above. The insulin may be neat (that is, in its substantially purified form), but may also include excipients as commercially formulated. Also included in the term "insulin" are insulin analogs where one or more of the amino acids of the naturally occurring or recombinantly produced insulin has been deleted or added.

It is to be understood that more than one active ingredient or agent may be incorporated into the aerosolized active agent formulation and that the use of the term "agent" or "ingredient" in no way excludes the use of two or more such agents. Indeed, some embodiments of the present invention contemplate administering combination drugs that may be mixed in situ.

Examples of diseases, conditions or disorders that may be treated according to embodiments of the invention include, but are not limited to, asthma, COPD (chronic obstructive pulmonary disease), viral or bacterial infections, influenza, allergies, cystic fibrosis, and other respiratory ailments as well as diabetes and other insulin resistance disorders. The dry powder inhalation may be used to deliver locally-acting agents such as antimicrobials, protease inhibitors, and nucleic acids/oligionucleotides as well as systemic agents such as peptides like leuprolide and proteins such as insulin. For example, inhaler-based delivery of antimicrobial agents such as antitubercular compounds, proteins such as insulin for diabetes therapy or other insulin-resistance related disorders, peptides such as leuprolide acetate for treatment of prostate cancer and/or endometriosis and nucleic acids or ogligo-nucleotides for cystic fibrosis gene therapy may be performed. See e.g. Wolff et al., *Generation of Aerosolized Drugs*, J. Aerosol. Med. pp. 89-106 (1994). See also U.S. Patent Application Publication No. 20010053761, entitled Method for Administering ASPB28-Human Insulin and U.S. Patent Application Publication No. 20010007853, entitled Method for Administering Monomeric Insulin Analogs, the contents of which are hereby incorporated by reference as if recited in full herein.

Typical dose amounts of the unitized dry powder mixture dispersed in the inhalers may vary depending on the patient size, the systemic target, and the particular drug(s). The dose amounts and type of drug held by a dose container system may vary per dose container or may be the same. In some embodiments, the dry powder dose amounts can be about 100 mg or less, typically less than 50 mg, and more typically between about 0.1 mg to about 30 mg.

In some embodiments, such as for pulmonary conditions (i.e., asthma or COPD), the dry powder can be provided as about 5 mg total weight (the dose amount may be blended to provide this weight). A conventional exemplary dry powder dose amount for an average adult is less than about 50 mg, typically between about 10-30 mg and for an average adolescent pediatric subject is typically from about 5-10 mg. A typical dose concentration may be between about 1-5%. Exemplary dry powder drugs include, but are not limited to, albuterol, fluticasone, beclamethasone, cromolyn, terbutaline, fenoterol, β-agonists (including long-acting β-agonists), salmeterol, formoterol, cortico-steroids and glucocorticoids.

In certain embodiments, the administered bolus or dose can be formulated with an increase in concentration (an increased percentage of active constituents) over conventional blends. Further, the dry powder formulations may be configured as a smaller administrable dose compared to the conventional 10-25 mg doses. For example, each administrable dry powder dose may be on the order of less than about 60-70% of that of conventional doses. In certain particular embodiments, using the dispersal systems provided by certain embodiments of the DPI configurations of the instant invention, the adult dose may be reduced to under about 15 mg, such as between about 10 µg-10 mg, and more typically between about 50 µg-10 mg. The active constituent(s) concentration may be between about 5-10%. In other embodiments, active constituent concentrations can be in the range of between about 10-20%, 20-25%, or even larger. In particular embodiments, such as for nasal inhalation, target dose amounts may be between about 12-100 µg.

In certain particular embodiments, during inhalation, the dry powder in a particular drug compartment or blister may be formulated in high concentrations of an active pharmaceutical constituent(s) substantially without additives (such as excipients). As used herein, "substantially without additives" means that the dry powder is in a substantially pure active formulation with only minimal amounts of other non-biopharmacological active ingredients. The term "minimal amounts" means that the non-active ingredients may be present, but are present in greatly reduced amounts, relative to the active ingredient(s), such that they comprise less than about 10%, and preferably less than about 5%, of the dispensed dry powder formulation, and, in certain embodiments, the non-active ingredients are present in only trace amounts.

In some embodiments, the unit dose amount of dry powder held in a respective drug compartment or dose container is less than about 10 mg, typically about 5 mg of blended drug and lactose or other additive (e.g., 5 mg LAC), for treating pulmonary conditions such as asthma. Insulin may be provided in quantities of about 4 mg or less, typically about 3.6 mg of pure insulin. The dry powder may be inserted into a dose container/drug compartment in a "compressed" or partially compressed manner or may be provided as free flowing particulates.

Some embodiments of the invention are directed to inhalers that can deliver multiple different drugs for combination delivery. Thus, for example, in some embodiments, some or all of the dose containers may include two different drugs or different dose containers may contain different drugs configured for dispensing substantially concurrently.

In some embodiments, a dose container disk for an inhaler device may include a first row of circumferentially spaced apart dose containers at a first radius and a second row of circumferentially spaced apart dose containers at a second radius so that the first and second rows are substantially concentric. In some embodiments, the same drug may be included in all of the dose containers. In other embodiments, a first drug may be included within the dose containers of the first row, and a second drug, different from the first drug, may be included within the dose containers of the second row.

The inhalers can be configured to provide any suitable number of doses, typically between about 30-120 doses, and more typically between about 30-60 doses. The inhalers can deliver one drug or a combination of drugs. In some embodiments, the inhalers can provide between about 30-60 doses of two different drugs (in the same or different unit amounts), for a total of between about 60-120 individual unit doses, respectively. The inhaler can provide between a 30 day to a 60 day (or even greater) supply of medicine. In some embodiments, the inhalers can be configured to hold about 60 doses of the same drug or drug combination, in the same or different unit amounts, which can be a 30 day supply (for a twice per day dosing) or a 60 day supply for single daily treatments.

Certain embodiments may be particularly suitable for dispensing medication to respiratory patients, diabetic patients, cystic fibrosis patients, or for treating pain. The inhalers may also be used to dispense narcotics, hormones and/or infertility treatments.

The dose container assembly and inhaler may be particularly suitable for dispensing medicament for the treatment of respiratory disorders. Appropriate medicaments may be selected from, for example, analgesics, e.g., codeine, dihydromorphine, ergotamine, fentanyl or morphine; anginal preparations, e.g., diltiazem; antiallergics, e.g., cromoglycate, ketotifen or nedocromil; antiinfectives e.g., cephalosporins, penicillins, streptomycin, sulphonamides, tetracyclines and pentamidine; antihistamines, e.g., methapyrilene; anti-inflammatories, e.g., beclomethasone dipropionate, fluticasone propionate, flunisolide, budesonide, rofleponide, mometasone furoate or triamcinolone acetonide; antitussives, e.g., noscapine; bronchodilators, e.g., albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3, 5-dichloro-α-[[6-[2-(2-pyridinyl) ethoxy]hexyl]methyl] benzenemethanol; diuretics, e.g., amiloride; anticholinergics, e.g., ipratropium, tiotropium, atropine or oxitropium; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon. It will be clear to a person of skill in the art that, where appropriate, the medicaments may be used in the form of salts, (e.g., as alkali metal or amine salts or as acid addition salts) or as esters (e.g., lower alkyl esters) or as solvates (e.g., hydrates) to optimize the activity and/or stability of the medicament.

Some particular embodiments of the dose container assembly and/or inhaler include medicaments that are selected from the group consisting of: albuterol, salmeterol, fluticasone propionate and beclometasone dipropionate and salts or solvates thereof, e.g., the sulphate of albuterol and the xinafoate of salmeterol. Medicaments can also be delivered in combinations. Examples of particular formulations containing combinations of active ingredients include those that contain salbutamol (e.g., as the free base or the sulphate salt) or salmeterol (e.g., as the xinafoate salt) in combination with an anti-inflammatory steroid such as a beclomethasone ester (e.g., the dipropionate) or a fluticasone ester (e.g., the propionate).

Some attributes of DPI devices, according to embodiments of the present invention, can be: 1) the ability to protect the dry powder from moisture ingress; 2) the number of doses contained within the inhaler; and 3) the overall size of the inhaler. In addition, it may be advantageous to fit the largest practical number of doses within the smallest possible inhaler. However, it may be necessary for individual doses to be spaced apart from each other to allow sufficient seal area and material thickness for moisture protection of the powder. One solution may be to use a dose ring with dose containers spaced equidistant from each other at two different radii, also referred to as a "staggered concentric" arrangement of doses.

Unfortunately, a challenge with a staggered concentric dose ring can be how to access each dose container for opening and inhalation. If all of the outer dose containers are opened first, followed by all inner dose containers, this may require an indexing device that will index a "half step" in order to effect the transition from the outer to inner ring of dose containers, but index a "full step" for all other dose containers. This indexing functionality may be difficult to achieve in inhaler devices. An alternative may be to create dose rings with a special arrangement of dose containers on the dose ring. Unfortunately, this may complicate the automated handling and filling of the powder into the dose ring.

Figure 1B:
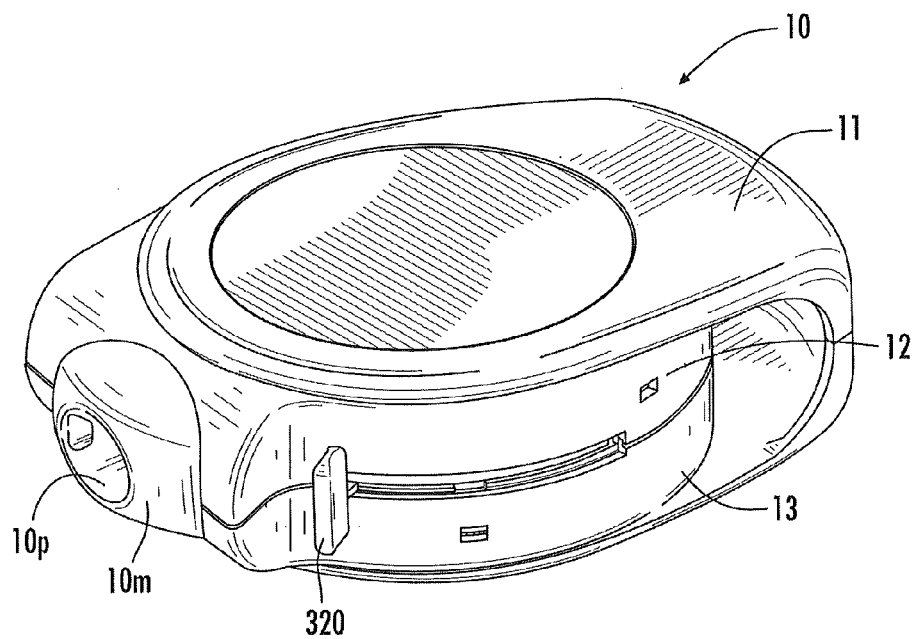
FIG. 1B is a front perspective view of the inhaler of FIG. 1A with the cover moved to an open or operational position.
Figure 1C:
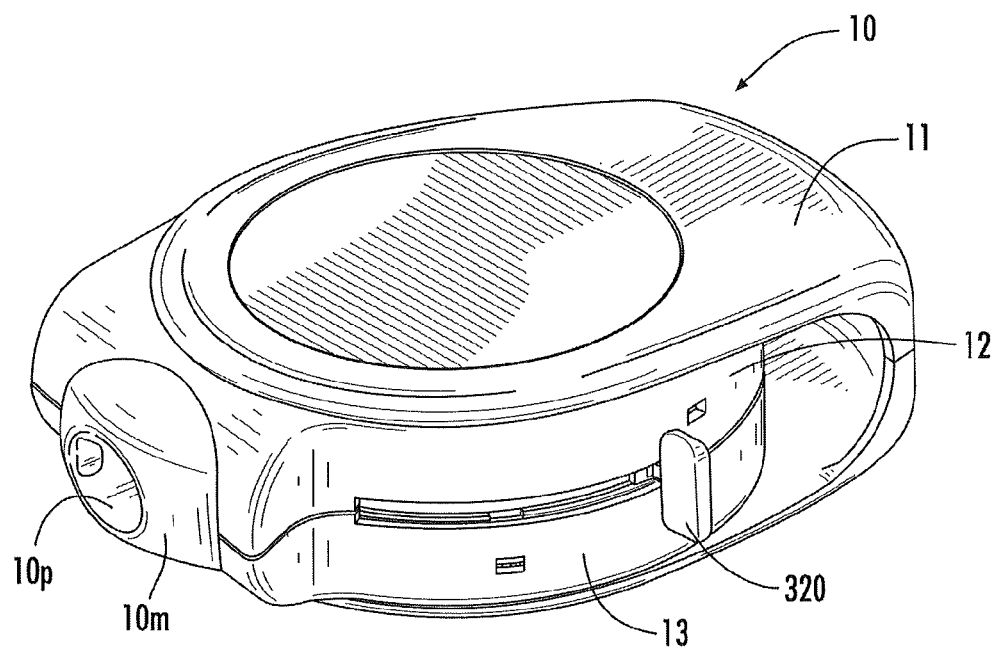
FIG. 1C is a front perspective view of the inhaler of FIG. 1B illustrating a user-accessible actuator lever moved to a second position.

Turning now to the figures, FIGS. 1A-1C illustrate an example of a multi-dose inhaler 10 with a cover 11, inhalation port 10p, and upper and lower housing portions 12, 13. However, this inhaler configuration is shown merely for completeness and embodiments of the invention are not limited to this inhaler configuration as other form factors, covers and inhalation port configurations may be used. In FIG. 1A the cover 11 is in a closed position. In FIG. 1B the cover 11 has been moved to an open or operational position. FIG. 1C illustrates the user lever 320 of an actuator mechanism 306 moved from a first position (FIG. 1B) to a second position, as will be described below.

Figure 2A:
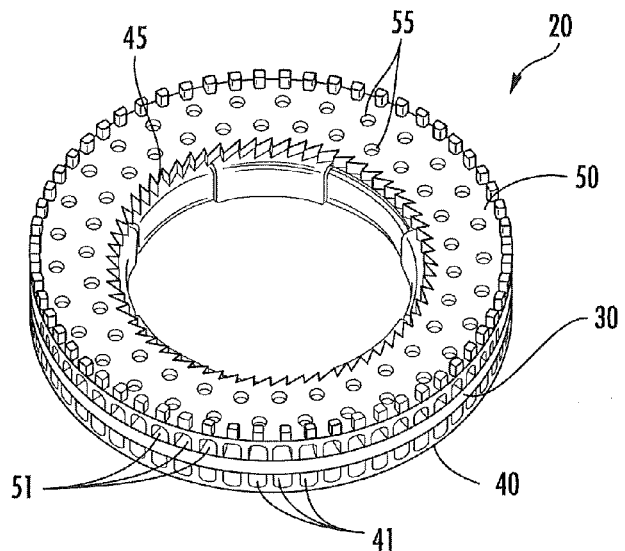
FIG. 2A is a top perspective view of a dose container assembly according to some embodiments of the present invention.
Figure 2C:
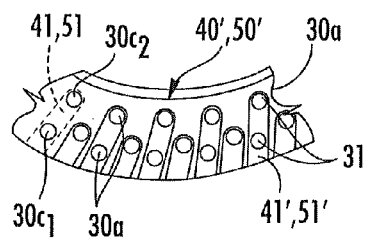
FIG. 2C is a partial cutaway view of airway channels aligned with two dose containers according to some embodiments of the present invention.
Figure 2B:
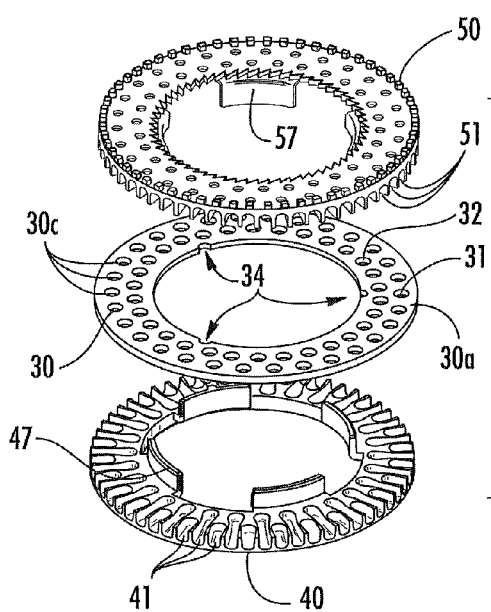
FIG. 2B is an exploded view of the assembly shown in FIG. 2A.

FIG. 2A illustrates a dose container assembly 20 for use within the multi-dose inhaler 10. The dose container assembly 20 includes a dose ring or disk 30 having a plurality of dose containers 30c. As shown in FIGS. 2B and 2E, in some embodiments, the dose ring or disk 30 can include a plurality of circumferentially spaced apart through apertures 30a that forms a portion of the dose containers 30c. As shown in FIG. 2E, the dose containers 30c can be defined by dose container apertures 30a and upper and lower sealants 36,37.

As shown, the dose container assembly 20 includes a lower airway disk 40 and an upper airway disk 50. In other embodiments, the dose container assembly 20 can include the dose container disk 30 and only one of the lower airway disk 40 or the upper airway disk 50. In such a configuration, another type of airway can be used for the other side of the disk 30, such as, but not limited to, a fixed or "global" upper or lower airway can be used with the individual airways provided by either an upper or lower airway disk 50, 40. Also, it is contemplated that the upper and lower airway disks 50, 40 described herein can be reversed for normal operation (or inadvertently for atypical operation) so that the lower airway disk is the upper airway disk and the upper airway disk is the lower airway disk.

As shown in FIGS. 2A and 2B, the lower and upper airway disks 40, 50, respectively, include a plurality of circumferentially spaced apart airway channels 41, 51, respectively. Typically, the disks 40, 50 include one channel 41, 51 for one dose container 30c. However, in other embodiments, as shown, for example, in FIG. 2C, a respective airway channel 51, 41 from one or both of the disks 50', 40' can be in communication with two different dose containers 30c. This configuration will allow for (simultaneous) combination delivery of dry powder from two containers in a respective airway channel pair (or single) or can allow one dose container $30c_1$ to release dry powder to the airway channel 41 and/or 51, then be used again later for the other dose container $30c_2$. Thus, embodiments of the invention allow for some or all airway channels 41, 51 to be used once or twice. Also, while embodiments of the invention are illustrated as releasing only a dose from a single dose container 30c during one delivery, other embodiments allow the inhalers to dispense a combination drug so that two or more dose containers 30c may use a respective airway channel 41, 51 for delivery.

In some embodiments, the airway channels 41, 51 can define airways that are not able to release dry powder residing in a respective airway channel to a user once the inhaler is indexed again to another position so that the respective airway channel is no longer in communication with the inhalation port 10p. The channels can be configured to have "sink traps" to inhibit spillage according to some embodiments of the present invention to provide overdose protection (unless the dual use configuration is used whereby only a single other dose may be released using that airway channel(s) as noted above).

Where two airway disks are used, e.g., both the lower and upper disks 40, 50, the inhaler device 10 can be configured to operate even when inverted and have the same overdose protection feature. Spillage of dry powder from the dose container 30c as the dose container 30c is opened can be influenced by gravity. For example, for a conventional obround or elliptical mouthpiece shape, there are two primary device orientations (right-side-up and upside-down), embodiments of the invention allow for operation of the inhaler device in both orientations. In the embodiment shown, for example, in FIG. 2A, this can be accomplished by having an individual airway section for a respective dose container 30c (or dose containers where combination drug delivery is desired) both above and below the target corresponding dose container(s) 30c.

Figure 2D:
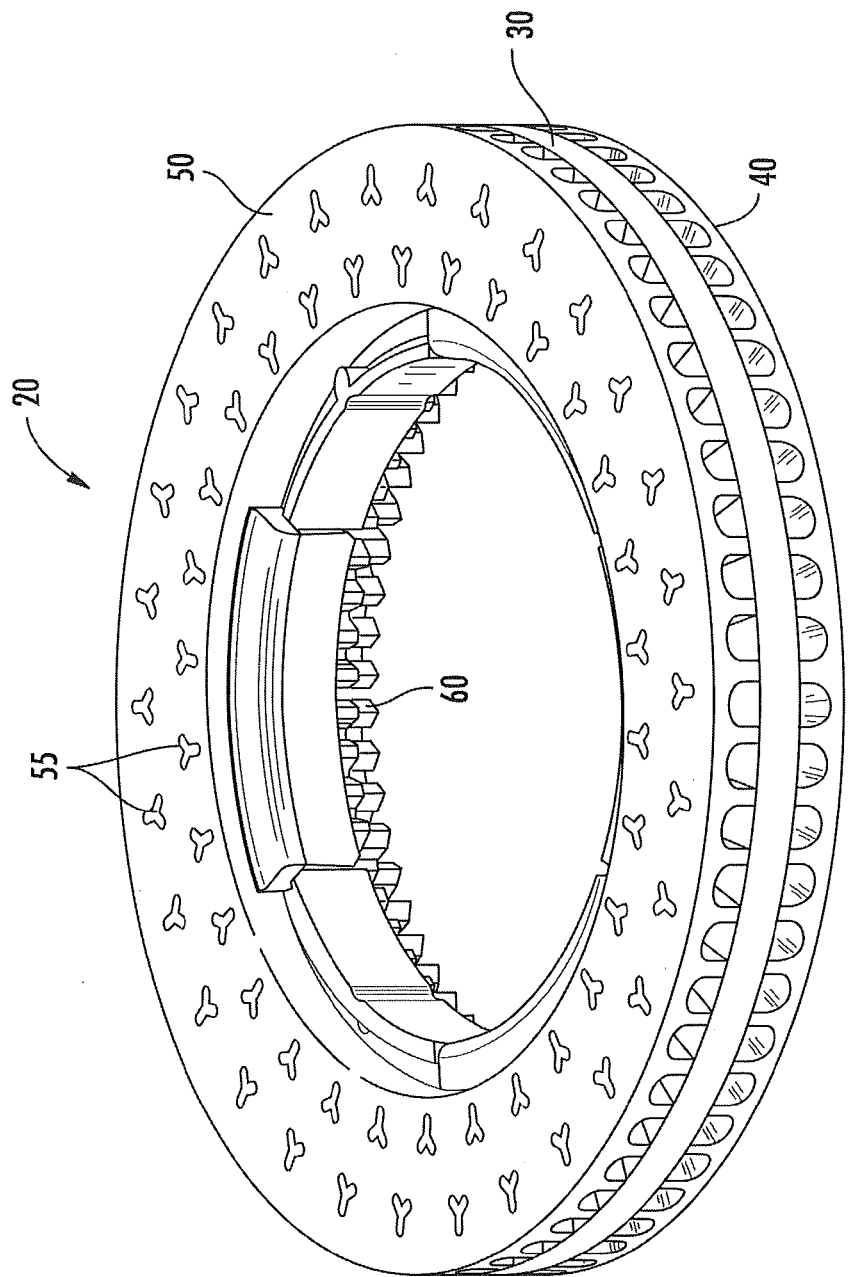
FIG. 2D is a top perspective view of another exemplary dose container assembly according to some embodiments of the present invention.
Figure 2E:
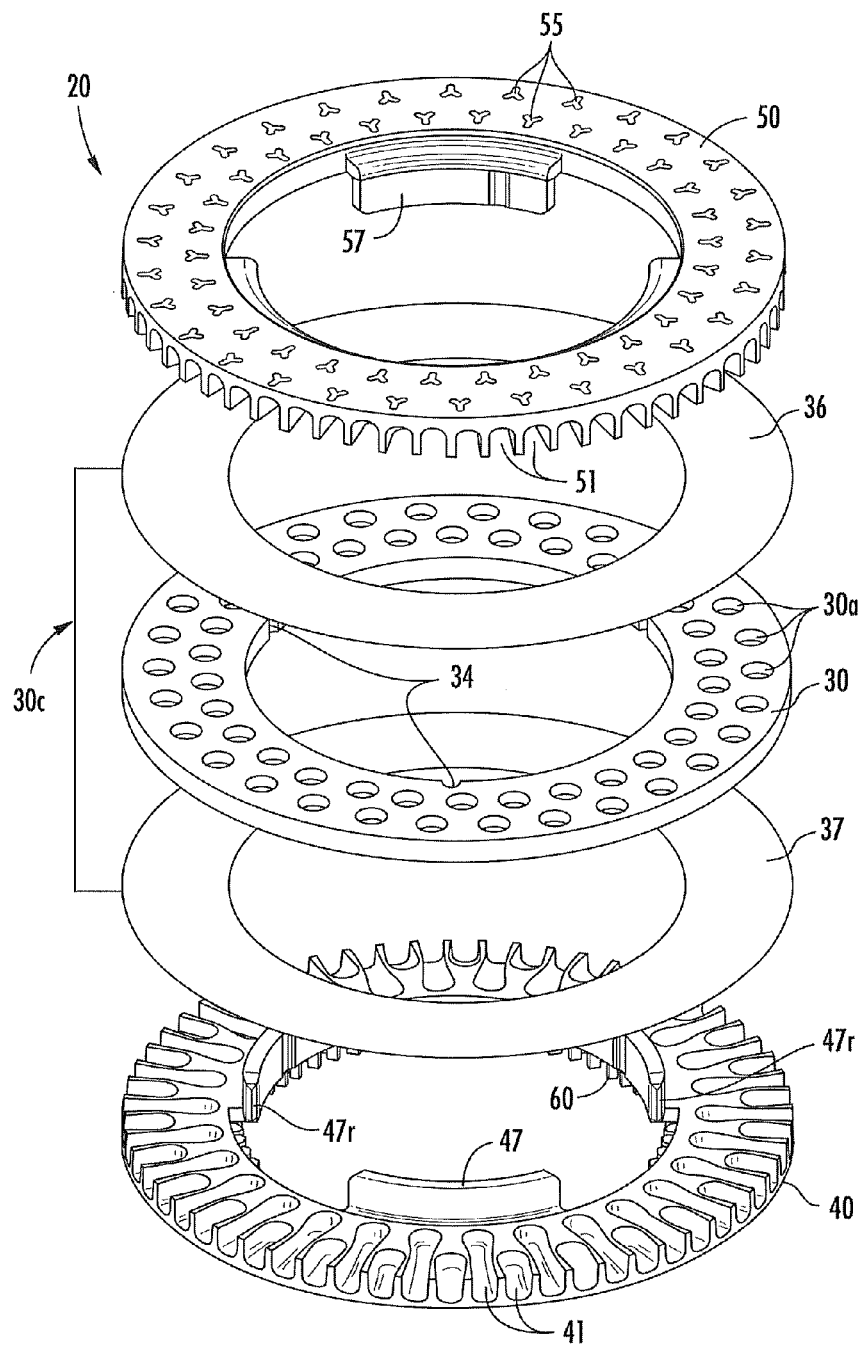
FIG. 2E is an exploded view of the dose container assembly shown in FIG. 2D according to embodiments of the present invention.
Figure 3A:
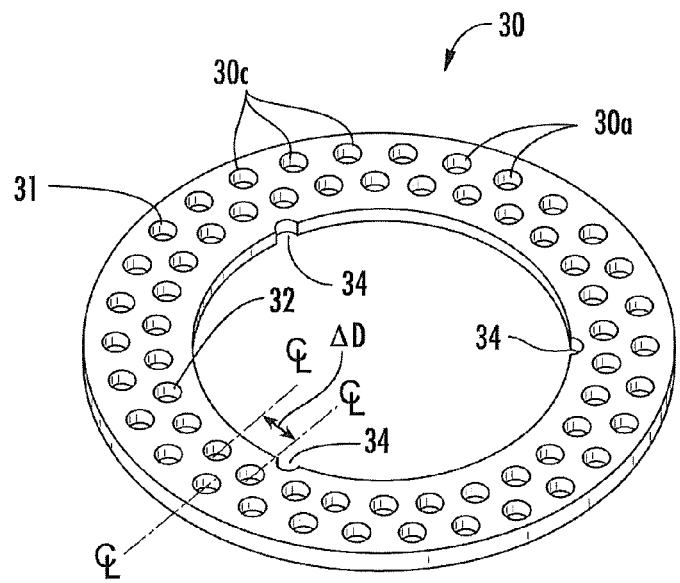
FIG. 3A is a top perspective view of a dose container ring according to some embodiments of the present invention.
Figure 3B:
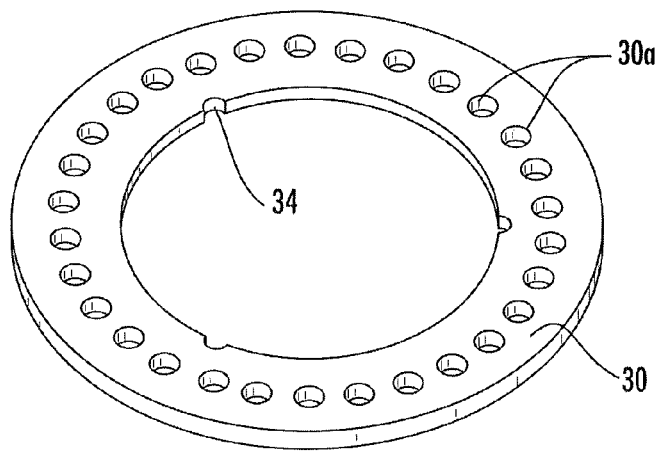
FIG. 3B is a top perspective view of a dose container ring according to some other embodiments of the present invention.

FIGS. 2A, 2D and 3A illustrate that the dose container disk 30 can include 60 dose containers 30c while FIG. 3B illustrates that the dose container disk 30 can include 30 dose containers 30c. Greater or lesser numbers of dose containers may be used. FIG. 2E illustrates that sealant layers 36, 37 may be configured as annular flat rings as shown and can be used to seal the top and bottom surfaces of the dose disk 30. The sealant layers 36, 37 can have the same or different material(s) and may include foil, polymer(s) and/or elastomer(s), or other suitable material or combinations of materials, including laminates. Typically, the sealant layers 36, 37 are thin flexible sealant layers comprising foil. The sealant layers 36, 37 (where used) may be provided as a substantially continuous ring as shown in FIG. 2E or may be attached to the dose container disk 30 as individual strips or spots of sealant that can be placed over and under the apertures 30a. In other embodiments, sealant layers may be provided on only one primary surface of the dose disk 30, and the apertures 30a may be closed on one side rather than have through apertures (not shown). In yet other embodiments, the dose disk 30 can have a blister configuration.

FIGS. 2B, 3A and 3B also illustrate that the dose container disk 30 can include at least one indexing notch 34, shown as a plurality of circumferentially spaced apart indexing notches 34. To assemble the assembly 20, a tab on one of the airway disks 40, 50, typically the lower disk 40, includes a radially extending tab 45 (FIG. 4A) that aligns with and engages one of those notches 34 to position the channels 41, 51 in alignment with the dose containers 30c. Other alignment means may be used including the reverse of the notch and tab configuration described (e.g., the airway disk can have the notch and the dose container disk can have the tab).

As shown in FIGS. 2B, 3A and 3B, the dose containers 30c may be arranged so that they are circumferentially spaced apart in one or more rows. As shown in FIG. 3A, the dose containers 30c are arranged in staggered concentric rows, an outer row 31 at a first radius from a center of the disk and an inner row 32 at a second different radius. As shown in FIG. 3A dose containers 30c on each respective row are spaced apart a distance "D" and the offset of the centerlines of those on the back row to those on the front row is "D/2". The dose container disk 30 can be a molded polymer, copolymer or blends and derivatives thereof, or may comprise metal, or combinations thereof, or other materials that are capable of providing sufficient moisture resistance.

The dose container disk 30 can have an outer diameter of between about 50-100 mm, typically about 65 mm and a thickness (FIG. 9) of between about 2-5 mm, typically about 3 mm. The disk 30 can comprise a cyclic olefin (COC) copolymer. The apertures 30a can have a diameter of between about 2-5 mm, typically about 3 mm and the sidewalls 30w of the dose containers 30c may have an angle or draft of about 1-3 degrees per side, typically about 1.5 degrees, as shown in FIG. 3D, to facilitate removal from a mold (where a molding process is used to form the disk 30). The dose container 30 is configured to be able to protect the powder from moisture ingress, while providing a desired number of doses in a compact overall inhaler size. The individual doses 30c are spaced apart from each other to allow sufficient seal area and material thickness for moisture protection of the powder.

Figure 3C:
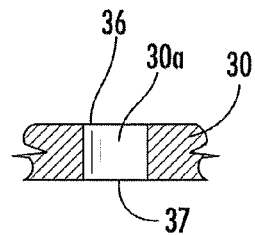
FIG. 3C is a partial cutaway view of a single dose container according to some embodiments of the present invention.
Figure 3D:
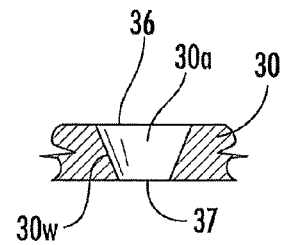
FIG. 3D is a partial cutaway view of a single dose container according to some embodiments of the present invention.

Similar to the embodiment shown in FIG. 2E, FIG. 3C illustrates that the dose containers 30c may be defined by apertures 30a sealed by sealant layers 36, 37 over and under the apertures 30a. The sealant can include foil, a polymer and/or elastomer, or other suitable materials or combinations of materials, including laminates. In a dry powder medicament inhaler 10, the drug powder is stored in a closed, moisture-resistant space provided by the dose containers 30c.

Embodiments of the invention provide a dose container assembly 20 that can provide a suitable seal and facilitate attachment of the airway disks 40, 50 to the dose ring or disk 30. In some embodiments, the dose container disk 30 contains sealants 36, 37 which may be a continuous layer over the upper and lower (primary) surfaces of the dose disk 30 and the upper and lower airway disks 50, 40 can contact the respective sealant and abut the dose disk to allow for a tight fit. The exemplary attachment features shown in FIG. 2E can reduce air leakage by allowing a close fit of the airway disks 40, 50 to the dose ring 30. The disks 40, 50 can sandwich the dose ring 30 and the dose ring can act as the "stop" to set the depth of engagement of the assembly features on the airway disks 40, 50. Embodiments of the invention provide a feature to index the airway disks 40, 50 relative to the dose ring 30, and some simple frictional engagement members, such as, but not limited to, "crush ribs", on one or both of the airway disks 40, 50 to secure their attachment to each other as will be discussed further below.

FIG. 4A illustrates an example of a lower airway disk 40. As shown, the disk 40 defines a plurality of circumferentially spaced apart channels 41. For the staggered concentric dose container configuration, the disk 40 can include alternating long and short airway channels 42, 43, respectively. Each channel 41 includes opposing end portions 41a, 41b, one (substantially or entirely) closed end portion 41a typically positioned adjacent the dose container 30c and one open end portion 41b. The open end portion 41b can merge into and/or is positioned adjacent the exit port 10p and/or mouthpiece 10m (FIGS. 7A-7C). The intake and flow can be in either direction and the open end 41b can be configured to face either the inner or outer perimeter of the disk 40 (e.g., be either positioned radially innermost or radially outermost on the disk 40). The channels 41 include upwardly extending sidewalls 41w with adjacent pairs of the long and short channels sharing one of the sidewalls 41w. Optionally, as shown by the broken line with respect to FIG. 4A, the channels 41 can include a small bleed hole 48 that allows air to enter but is sized to inhibit dry powder from exiting therefrom (the bleed holes 48 are shown only with a few of the channels 41 for ease of illustration).

Figure 4B:
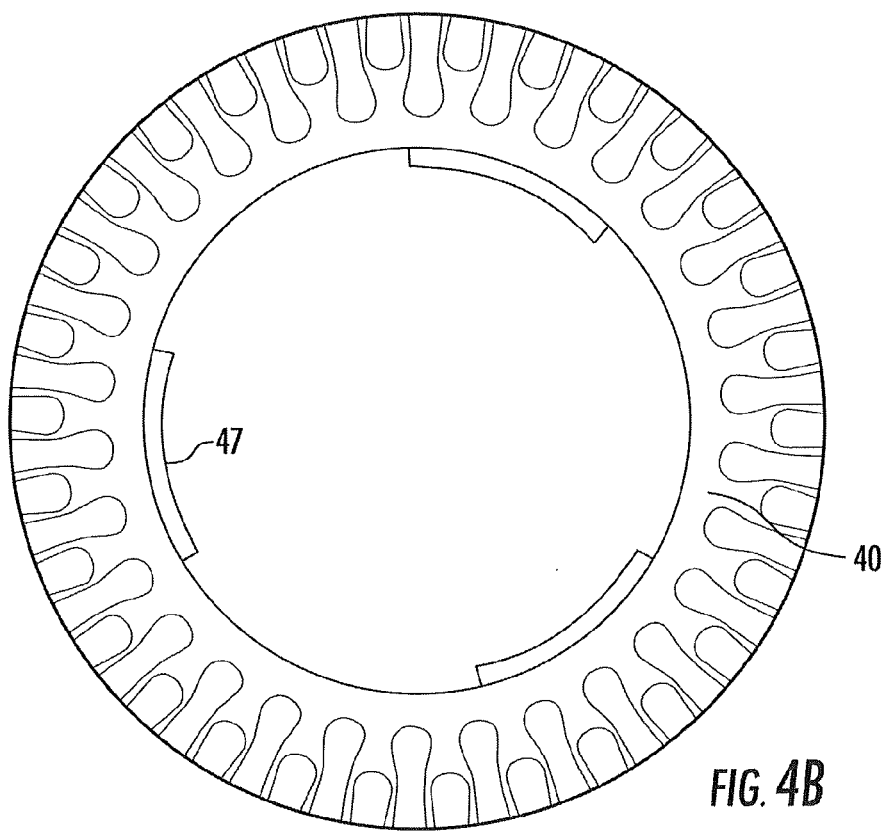
FIG. 4B is a top view of a lower airway disk according to some embodiments of the present invention.

FIGS. 4A and 4B illustrate that the disk 40 can include circumferentially spaced apart upwardly extending tabs 47, one of which includes the radially extending tab 45 discussed above. The disk 40 can also include circumferentially extending recesses 49 which align with tabs on the upper airway disk 50 to sandwich the dose disk therebetween. The tabs 47 can include crush ribs 47r that matably engage with tabs 57 on the upper airway disk 50 (FIG. 5A) to hold the three piece assembly 20 with sufficient force without requiring any additional attachment means.

Figure 4C:
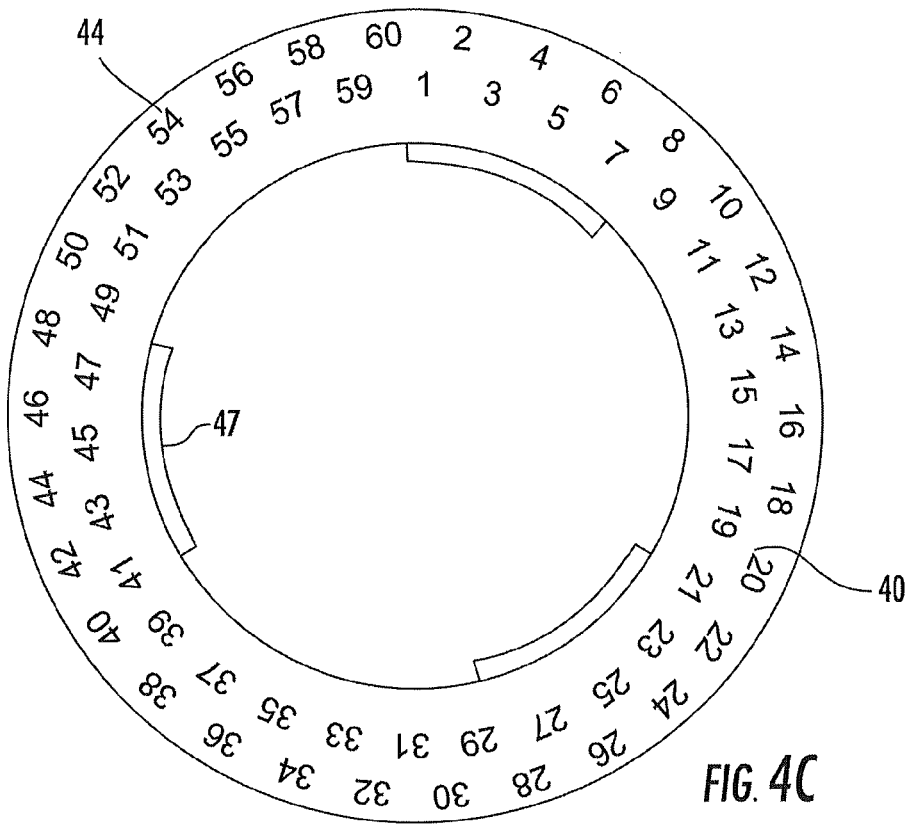
FIG. 4C is a bottom view of the lower airway disk shown in FIG. 4B.
Figure 14C:
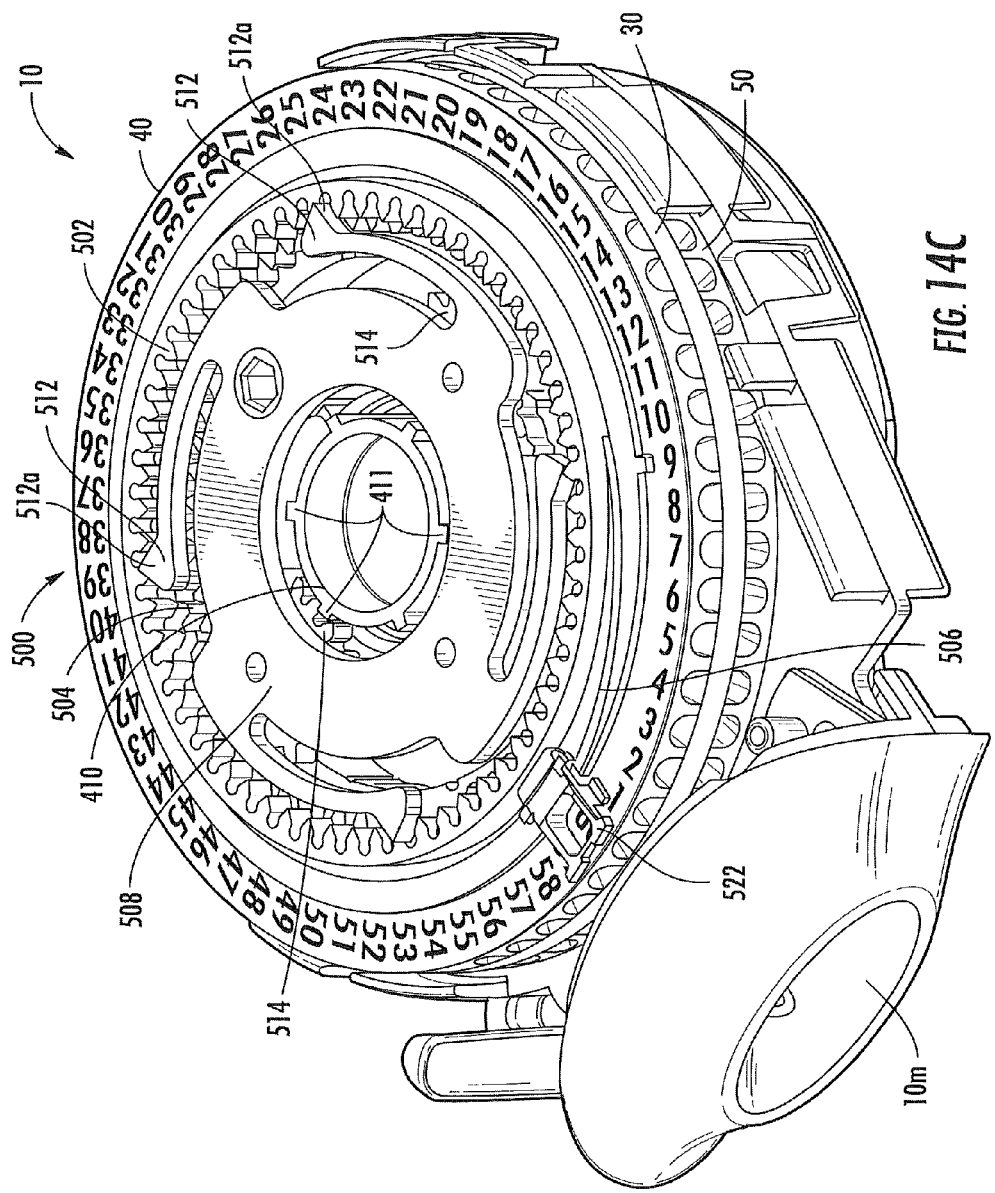
FIG. 14C is a bottom, cutaway perspective view of the inhaler of FIG. 10B illustrating the dose disk indexing mechanism, according to some embodiments of the present invention.

FIG. 4C illustrates that the disk 40 can also include dose indicia 44 so that a user can visually note what dose is being dispensed or a number of doses left in the inhaler. The dose indicia 44 can align with a dose reading aperture in the inhaler housing so that a user can visually assess the dose indicia/information that is visible to a user when a respective dose is indexed or is next to be indexed, to the dispensing position. Dose indicia 44 may also or alternatively be placed on the upper disk 50 and aligned with a dose reading aperture (not shown), or on both disks (also not shown). FIG. 14C illustrates that dose indicia may be placed along the outer perimeter edge of the lower surface of the lower disk 40, and numbered sequentially 1-60, but other patterns may be used, depending on the opening sequence (and the number of doses on the disk). In some embodiments, the dose indicia numbering can serially progress to alternate between rows of the dose containers 30 where the dose containers are opened in sequence in alternate rows, e.g., number 1 on the outer row, number 2 on the inner row, number 3 on the outer row (or vice versa) and so on. However, other dose numbering patterns may be used, depending on the opening sequence (and the number of doses on the disk). That is, this numbering may be appropriate where the inhaler is configured to open a dose container in one row, then open an adjacent dose container in the other row (e.g., inner to outer ring or outer to inner ring of dose containers), and repeating this sequence serially, where two rows of dose containers are used. However, other embodiments may open all the inner dose containers or all the outer dose containers, then open the dose containers in the other row or use a different alternating pattern of opening the dose containers on the inner and outer rows, and the dose numbering indicia on the disk 40 and/or 50 can be presented accordingly.

Figure 5A:
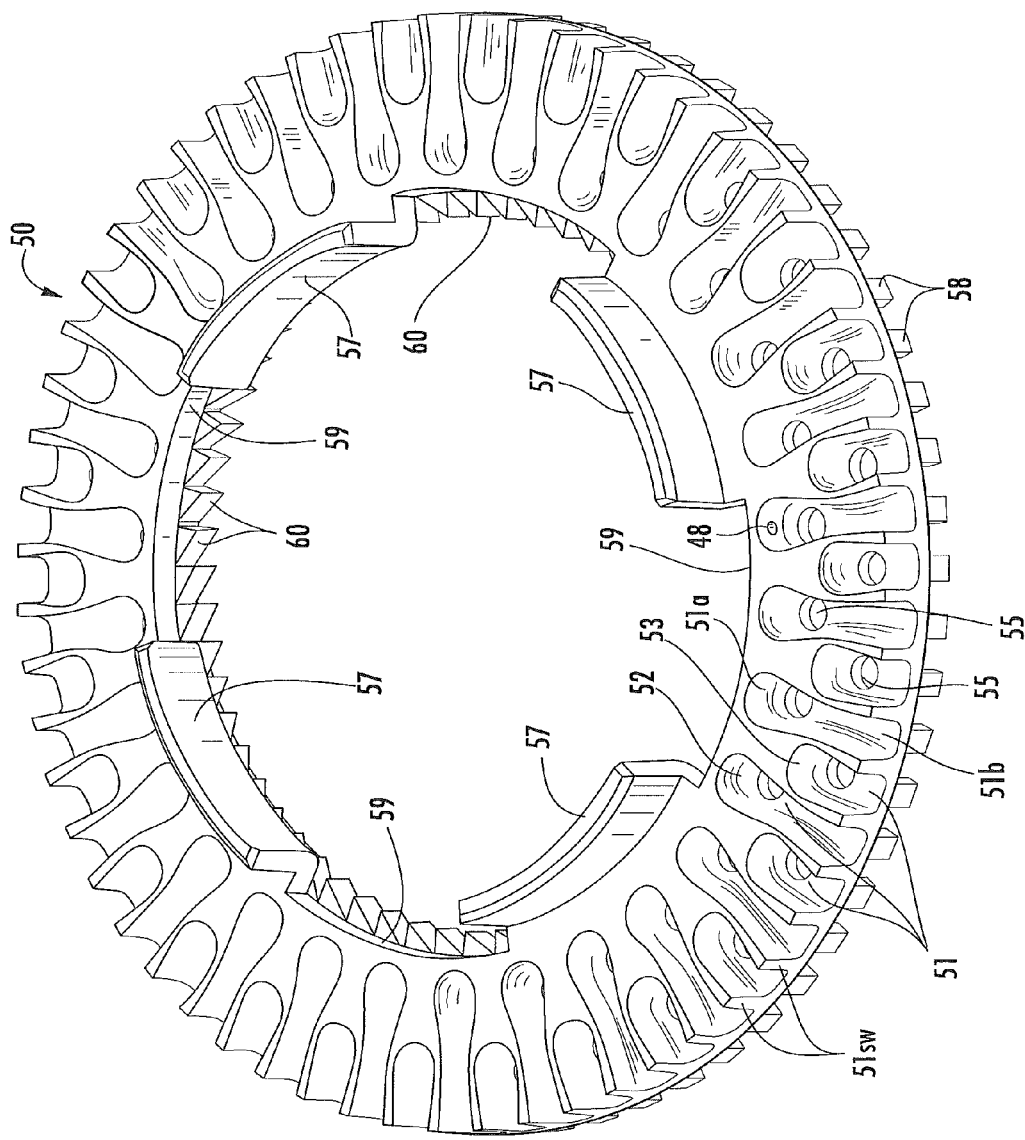
FIG. 5A is a greatly enlarged top perspective view of an upper airway disk according to some embodiments of the present invention.

FIG. 5A illustrates an example of an upper airway disk 50. In this embodiment, the upper airway disk 50 is shown inverted from its normal use position (and inverted relative to the orientation shown in FIG. 2A). As shown, the disk 50 defines a plurality of circumferentially spaced apart channels 51. For the staggered concentric dose container configuration, the disk 50 can include alternating long and short airway channels 52, 53, respectively. Each channel 51 includes opposing end portions 51a, 51b, the closed or substantially closed portion 51a is typically positioned adjacent the dose container 30c. The intake and flow can be in either direction and the open end 51b can be configured to face either the inner or outer perimeter of the disk 50 (e.g., be either positioned radially innermost or radially outermost). The other (open) end portion 51b merges into and/or is positioned adjacent the exit port 10p and/or mouthpiece 10m (FIGS. 7A-7C) and/or make-up air port or channel. The channels 51 include outwardly extending sidewalls 51sw with adjacent pairs of the long and short channels sharing one of the sidewalls 51sw. Optionally, the channels 51 can include a small bleed hole 48 (shown with only one channel for ease of illustration) that allows air to enter but is sized to inhibit dry powder from exiting therefrom.

As also shown in FIG. 5A, each channel 51 can include an aperture 55 that is configured to reside over a respective dose container 30c with the upper sealant layer 36 of the dose container 30c residing under the aperture 55. The apertures 55 allow a piercing (e.g., slicing or puncturing) member (e.g., 220a, 220b, FIG. 10A) to extend through the aperture 55 and open the sealant layers 36, 37 (FIG. 3C). As shown in FIG. 5A, the upper disk 50 can also include one or more of indexing ribs 58 and/or inner perimeter gear teeth 60 or other features that can index the disk within the inhaler to rotate the disk to provide the different dose containers 30c to a dispensing position and/or position a piercing mechanism over the target dose container for dispensing to open the dose container 30c. In other embodiments, one or both of these rotating and positioning mechanisms (or different features) can be provided on the lower disk 40 or the dose disk 30.

Figure 5B:
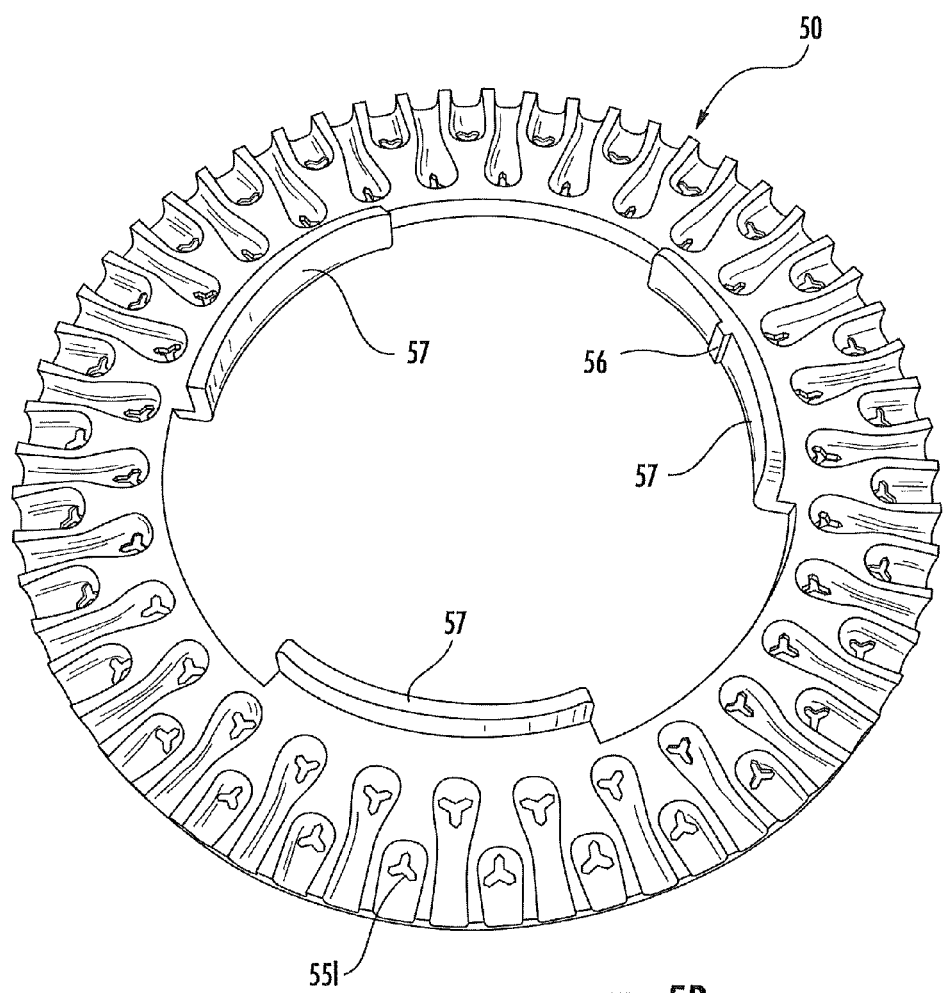
FIG. 5B is a greatly enlarged perspective view of an upper airway disk according to other embodiments of the present invention.

FIG. 5B illustrates that the disk 50 can include three tabs 57 instead of four as shown in FIG. 5A (the lower airway disk 40 can also include three tabs instead of four in this embodiment, see FIGS. 4B, 4C). One of the tabs 57 can have a vertically extending orientation rib 56, shown on an inner perimeter surface of the tab 57. In some embodiments, the orientation rib 56 on the upper disk 50 cooperates with a piercing frame associated with the piercing mechanism fixed in the inhaler housing so that the orientation rib 56 aligns to the frame to set a correct initial position according to dose number (e.g., 1) and prevents indexing past the number of doses in the disk assembly 20. Stated differently, the orientation rib 56 cooperates with the inhaler housing to set an initial position of the disk assembly 20 and also stops the disk assembly 20 from rotating around more than once.

FIG. 5B also illustrates that the apertures 55 can be configured with a geometry that corresponds to the shape of the piercer 220. The apertures 55 can be configured to closely surround the piercer 220. The piercer 220 can be a fluted piercer. As shown, the aperture 55 has three lobes 55l to snugly matably receive a correspondingly shaped three lobe (fluted) piercer 220 (FIG. 19D). The fluted piercer can have other number of lobes, such as, for example four circumferentially spaced apart lobes, as shown in FIG. 19F and the apertures 55 can have a corresponding four lobe shape. The lobes 55l can be in a different orientation in the inner row versus the outer row, e.g., rotated 180 degrees.

Figure 6:
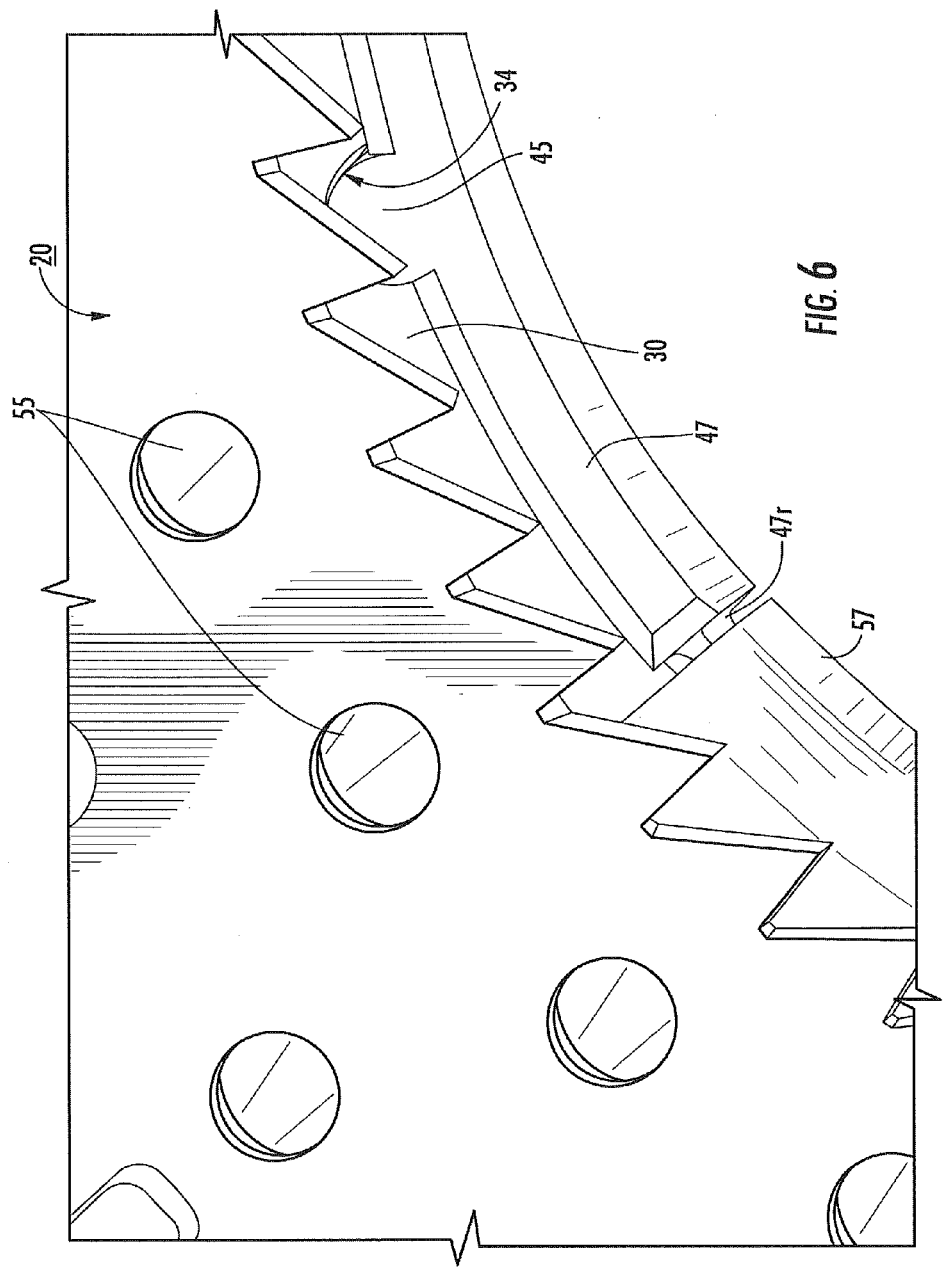
FIG. 6 is a greatly enlarged partial view of the dose container assembly shown in FIG. 2A according to embodiments of the present invention.

FIGS. 2A and 6 illustrate the dose container assembly 20 integrally attached together. FIGS. 2B, 4A, and 5A illustrate the exemplary disk components, 30, 40, 50. The tabs 57 of the disk 50 fit into recesses 49 of the disk 40 and the tabs 47 of the disk 40 fit into spaces 59 of the disk 50 with the crush ribs 47r firmly abutting the outer edges of tabs 57 to frictionally engage the components together with the dose disk 30 sandwiched therebetween with a flush fit via a relatively easy "press-fit" assembly method. The dose container disk 30 is aligned with the upper and lower airway disks 50, 40 via the (radially outward extending) tab 45 that engages one of the alignment notches 34 of the dose container ring 30 as discussed above. However, other alignment features or indicia may be used as well as other attachment configurations.

The upper and lower airway disks 50, 40 (where both are used) can be attached to the dose container disk 30 so as to reduce any gaps in the airway path defined thereby. The disk 30 can be a stop for attachment features on the airway disks 40, 50. The disk 30 with the sealants 36, 37 can have substantially planar upper and lower primary surfaces without requiring any attachment features. The lower portion of the upper airway disk 50 and the upper portion of the lower airway disk 40 can snugly reside against the respective opposing primary surfaces of the dose container disk 30 so that the attachment features/components are only on the upper and lower disks 50, 40 allowing for a snug and sufficiently air-tight interface between the disks 30, 40, 50 without gaps created by tolerances in other build configurations. The press-fit attachment without use of adhesives while providing for the substantially air-tight interface can be advantageous and cost-effective. However, as noted above, other attachment configurations may be used, including, for example, ultrasonic welding, adhesive, laser weld, other friction fit and/or matable configurations, the use of seals (O-rings, gaskets and the like) between the connection regions of the walls of the airway channels facing the dose container 30c and the sealant layers 36, 37 over and/or under the dose containers 30c of the disk, including combinations thereof, and the like.

As shown in FIGS. 7A-7C, in operation, pairs of upper and lower aligned channels 41, 51 can reside over and under a respective dose container 30c and are in fluid communication via the opened dose container 30c and aperture 30a. That is, as shown in FIG. 7A, a piercing member 220 advances to pierce the upper and lower sealant layers 36, 37, respectively (FIG. 3C). The piercing member 220 can be configured to extend and remain in the lower airway channel or may (partially or fully) retract before dispensing after opening the lower sealant. Also, although shown as extending down to pierce the sealant layers, the piercing member 220 can be configured to extend upward from the bottom. Either way, the piercing member 220 can be configured to occlude the aperture 55 in the upper (or lower disk).

As shown in FIG. 7B, the piercing member 220 can then partially or fully retract, or stay extended in the lower (or upper) airway channel, depending on the configuration of the mechanism, but is typically configured to plug and/or cooperate with a member that can plug the aperture 55 of the upper disk 50 (or lower disk 40 if piercing from the bottom) or otherwise occlude this passage so that the piercing member 220 and/or cooperating member substantially blocks, occludes (and/or seals) the aperture/opening 55 (FIGS. 2A, 5A, 5B). In this way, if the inhaler is inverted, powder is prevented from spilling out of the channel 51 because of the blockage provided by the piercing member 220. The airflow path 10f may be any direction from above to below the dose container 30c or vice versa or from the inner perimeter to the outer or vice versa, shown for example only in FIG. 7B by the arrow to allow air to flow through the bottom channel up through the aperture 30a and out the top channel 51 to the mouthpiece 10m. It is also noted that the exit or open end portion of the channel 41b, 51b may face the inner perimeter rather than the outer perimeter of the disc assembly 20.

After dispensing, the piercing member 220 is fully retracted as shown in FIG. 7C and the dose container assembly 20 can be rotated to a dispensing position and/or the piercing member 220 can be activated to open a different dose container 30c. In operation, the dose container assembly 20 can be radially pushed outward to seal or provide a snug exit path for the airway channel 41 and/or 51 against the mouthpiece 10m. A seal, such as an O-ring may be used to provide a sufficiently air-tight path between the airflow exit path and the disk assembly 20. Other airpath seal or closure configurations may be used.

Figure 8A:
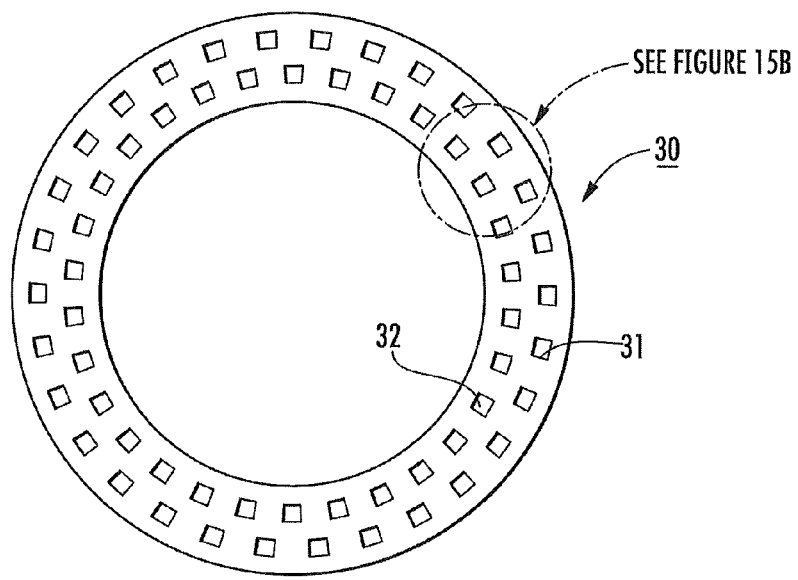
FIG. 8A is a top view of a dose container ring according to some embodiments of the present invention.
Figure 8B:
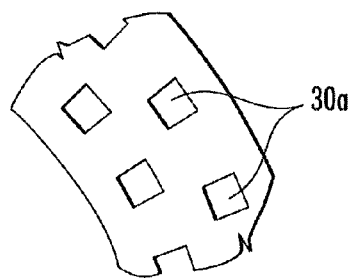
FIG. 8B is a partial enlarged fragmentary view of the ring shown in FIG. 8A.
Figure 9:
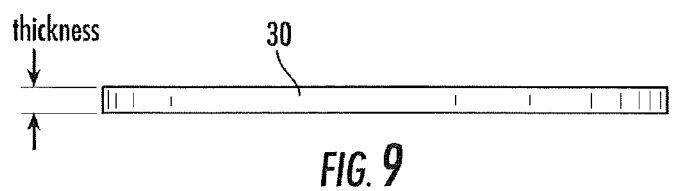
FIG. 9 is a side view of the ring shown in FIG. 8A.

FIGS. 8A, 8B and 9 illustrate an example of a dose container disk or ring 30 with two rows of apertures 30a used for dose containers 30c. The dose container disk 30 can be relatively thin, such as about 2-4 mm thick. The dose container apertures 30a can be configured so that the inner row 32 is at least about 2 mm from the outer row 31 and so that the inner and outer rows of dose containers are spaced inward from the respective perimeters by about 2 mm. This spacing can provide sufficient moisture permeability resistance and/or oxygen resistance.

Figure 10A:
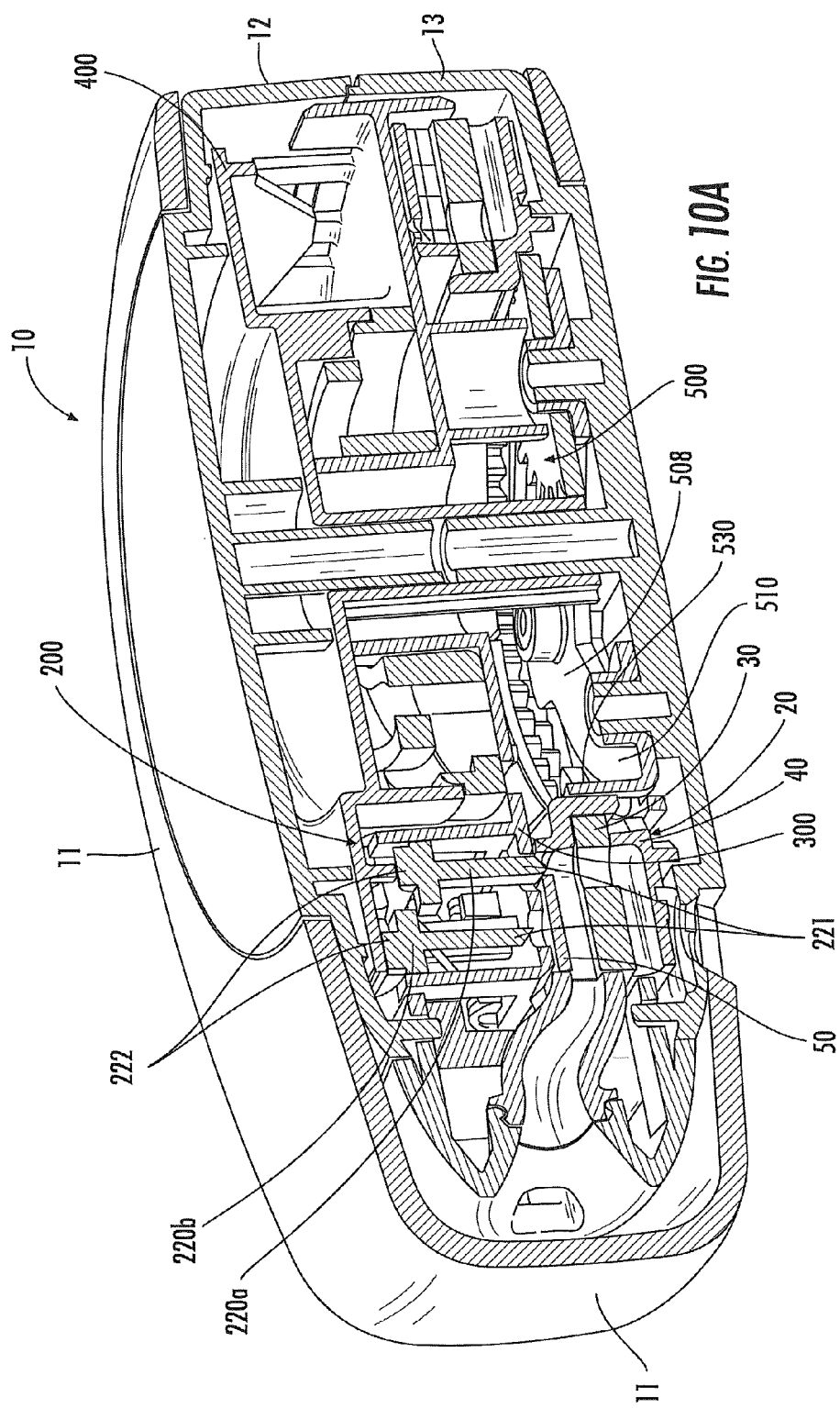
FIG. 10A is a cutaway, partial perspective view of an inhaler having a reciprocating dual piercing mechanism, according to some embodiments of the present invention.

FIG. 10A is a cutaway, partial perspective view of an inhaler 10, according to some embodiments of the present invention. A dose container assembly 20, including a dose container disk 30 and upper and lower airway disks 40, 50, is rotatably secured within the inhaler housing portions 12, 13. As described above with respect to FIGS. 3A and 3C, the dose container disk 30, in some embodiments, has opposing upper and lower primary surfaces, a first row of circumferentially spaced apart dose containers 30c at a first radius and a second row of circumferentially spaced apart dose containers 30c at a second radius so that the first and second rows are concentric with respect to a center of the disk 30. The dose containers 30c contain dry powder therein and are defined by apertures 30a, which can be sealed by sealants 36, 37 over and under the apertures 30a. In some embodiments, however, a dose container disk 30 may have a solid bottom with one sealant overlying dose container apertures, as would be understood by those skilled in the art.

As shown in FIG. 10A, in some embodiments the inhaler 10 includes a reciprocating dual piercing mechanism 200 that is mounted to a piercing frame 300 and which is controlled by a rotatable ramp disk 400. The inhaler 10 also includes an indexing mechanism 500 for rotating the disk container assembly 20. The piercing mechanism 200 is operably associated with the dose container assembly 20 and is configured to pierce the first and second sealants 36, 37 that seal a dose container 30c. The piercing mechanism 200 includes two piercing members 220a, 220b that are configured to pierce the sealants 36, 37 over and under dose containers 30c in the respective two rows of dose containers 30c. For example, the first piercing member 220a is configured to pierce the sealants 36, 37 over and under dose containers 30c in a first row of dose container apertures 30a, and the second piercing member 220b is configured to pierce the sealants 36, 37 over and under dose containers 30c in a second row of dose container apertures 30a. Each piercing member 220a, 220b includes a distal piercing end 221 and a proximal end 222.

Figure 10B:
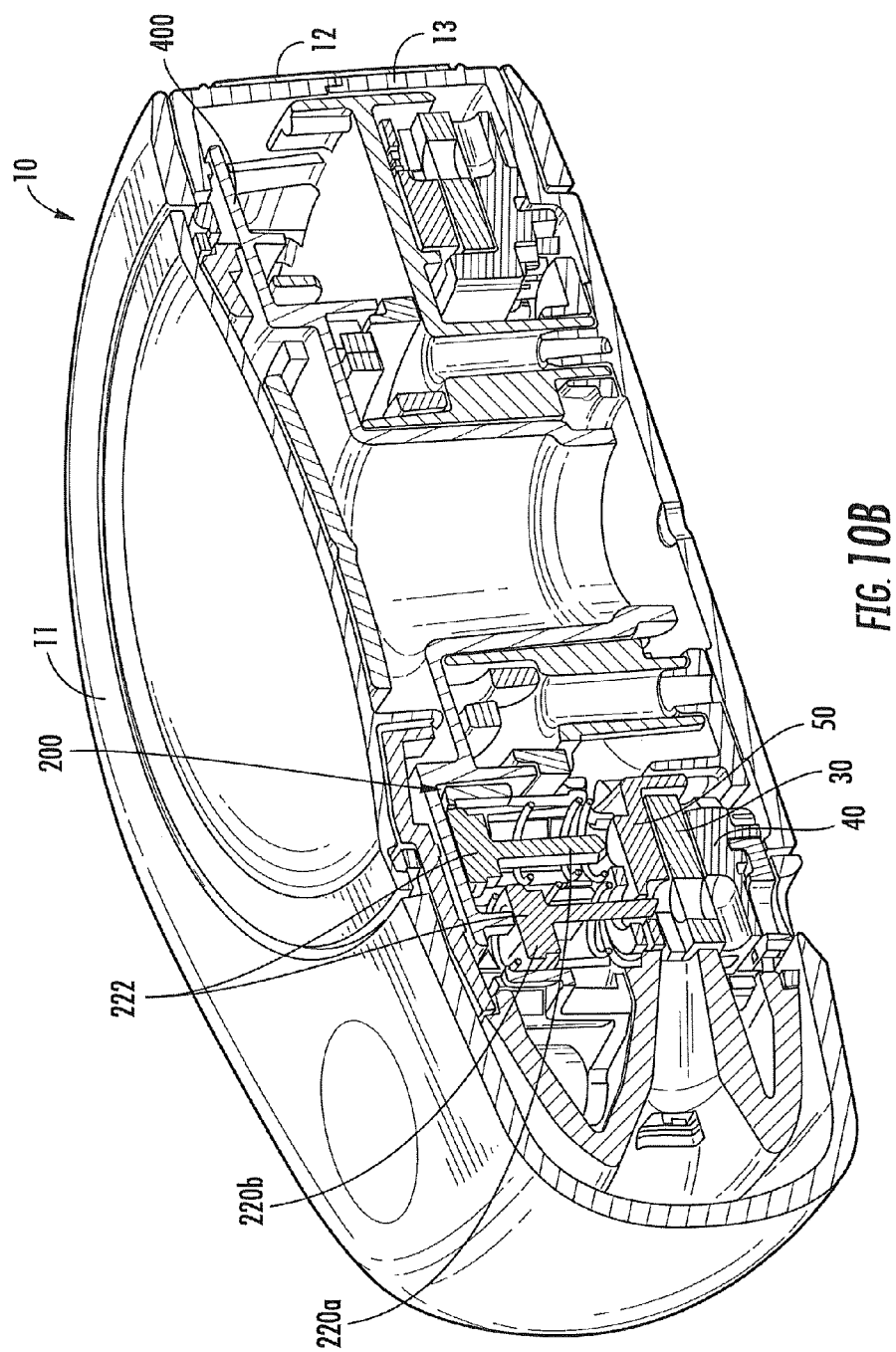
FIG. 10B is a cutaway, partial perspective view of an inhaler having a reciprocating dual piercing mechanism, according to some embodiments of the present invention.

FIG. 10B is a cutaway, partial perspective view of an inhaler 10 according to other embodiments of the present invention. The inhaler 10 illustrated in FIG. 10B incorporates the ramp disk 400 of FIGS. 11B, 13B and 13C, and the piercing frame 300 of FIG. 16B, which are described below.

Figure 11A:
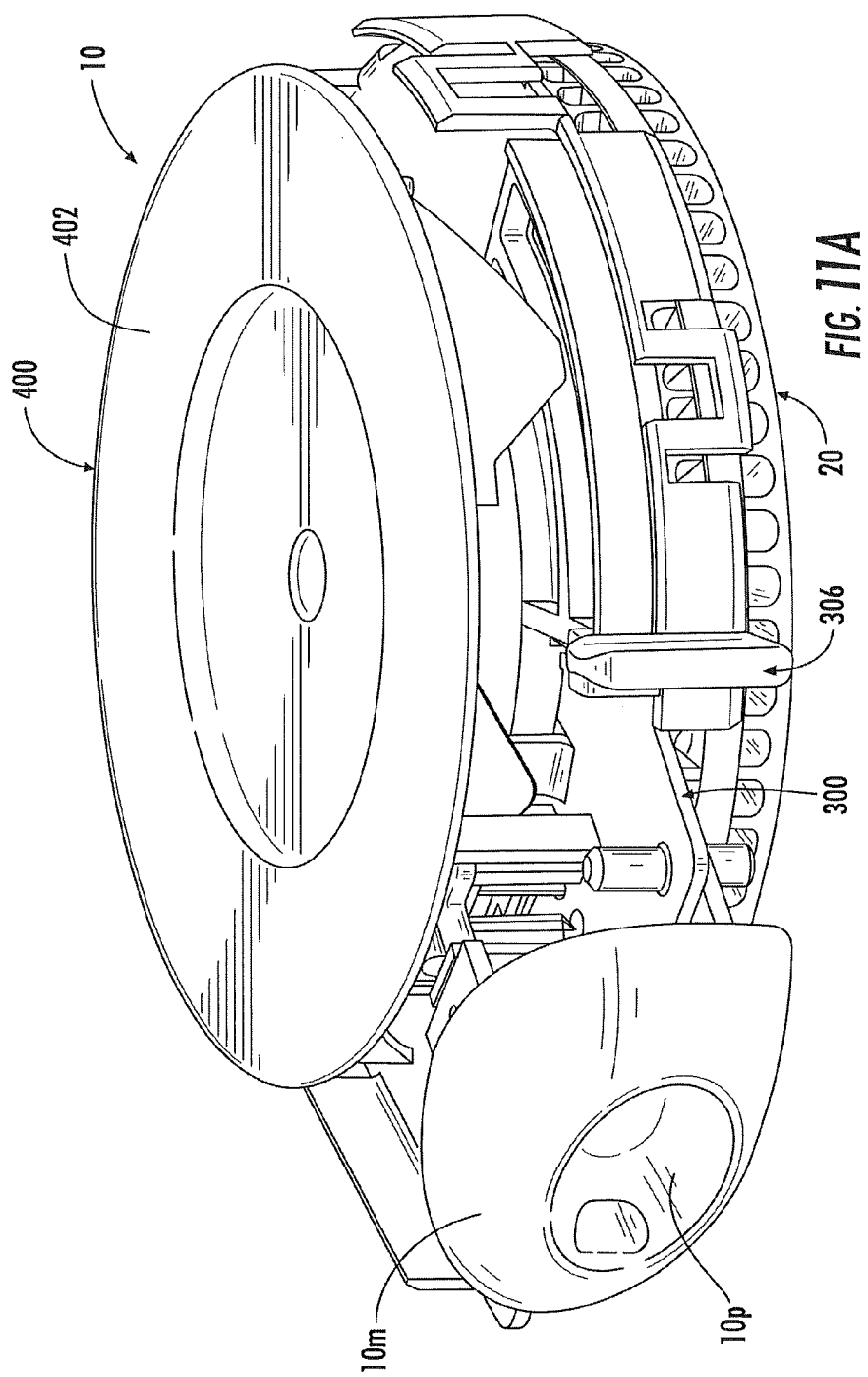
FIG. 11A is a top perspective view of the inhaler of FIG. 10A with the cover and upper and lower housing portions removed.

Referring now to FIGS. 11A-11C, 12A-12B, and 13A-13C, the piercing mechanism 200 and components operably associated therewith in various embodiments of the present invention are illustrated. FIG. 11A is a top perspective view of the inhaler of FIG. 10A with the cover 11 and upper and lower housing portions 12, 13 removed. In the illustrated orientation, a ramp disk 400 overlies a piercing frame 300, and the piercing frame 300 overlies the dose container assembly 20. An actuator mechanism 306 is rotatably secured to the piercing frame 300 and is operably associated with the ramp disk 400 to rotate the ramp disk 400 so as to selectively move each of the piercing members 220a, 220b of the piercing mechanism 200 between .respective piercing and retracted positions, and more specifically, between respective piercing positions, partially retracted positions, and fully retracted positions.

Figure 11B:
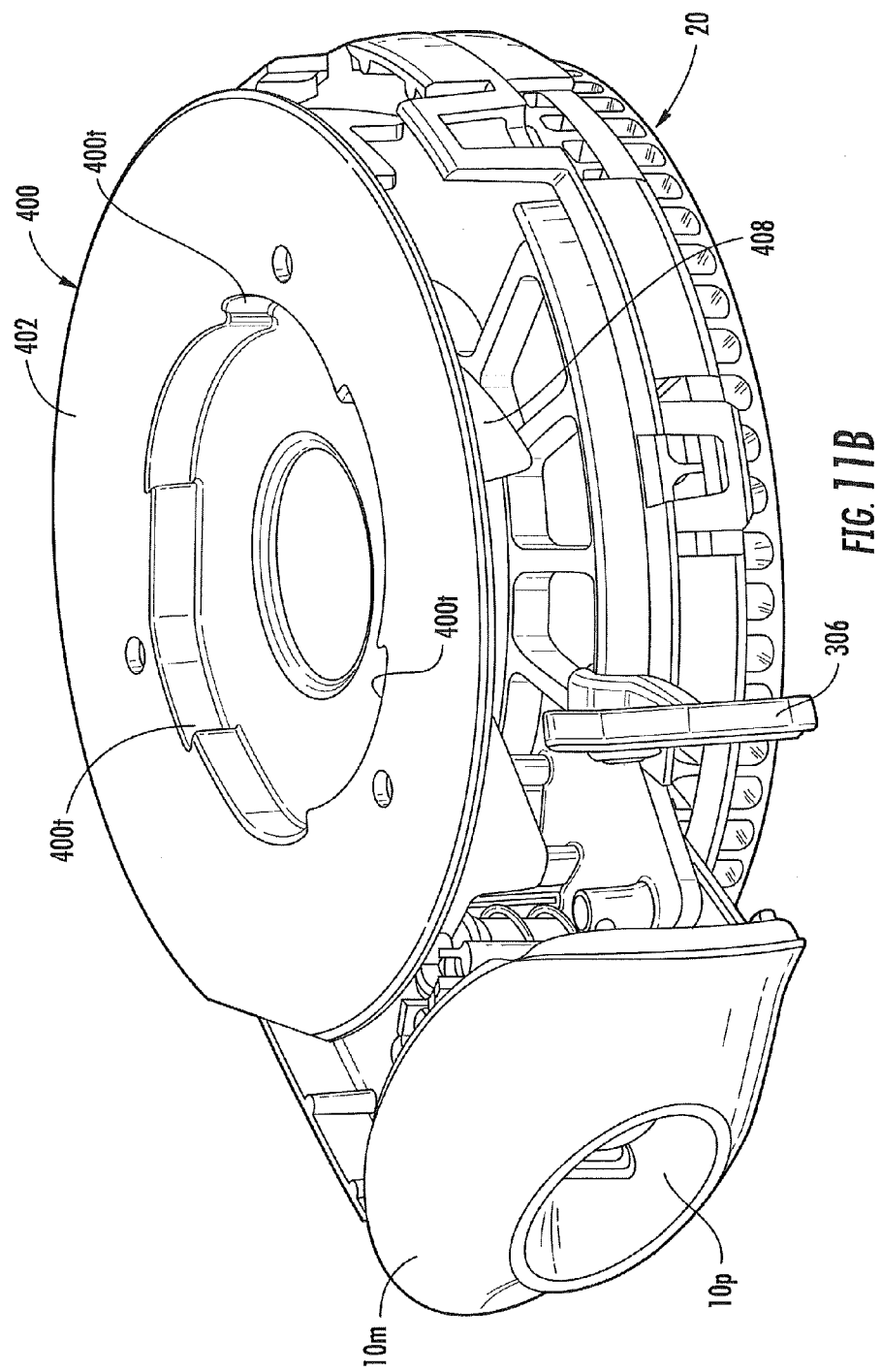
FIG. 11B is a top perspective view of the inhaler of FIG. 10B with the cover and upper and lower housing portions removed.
Figure 11C:
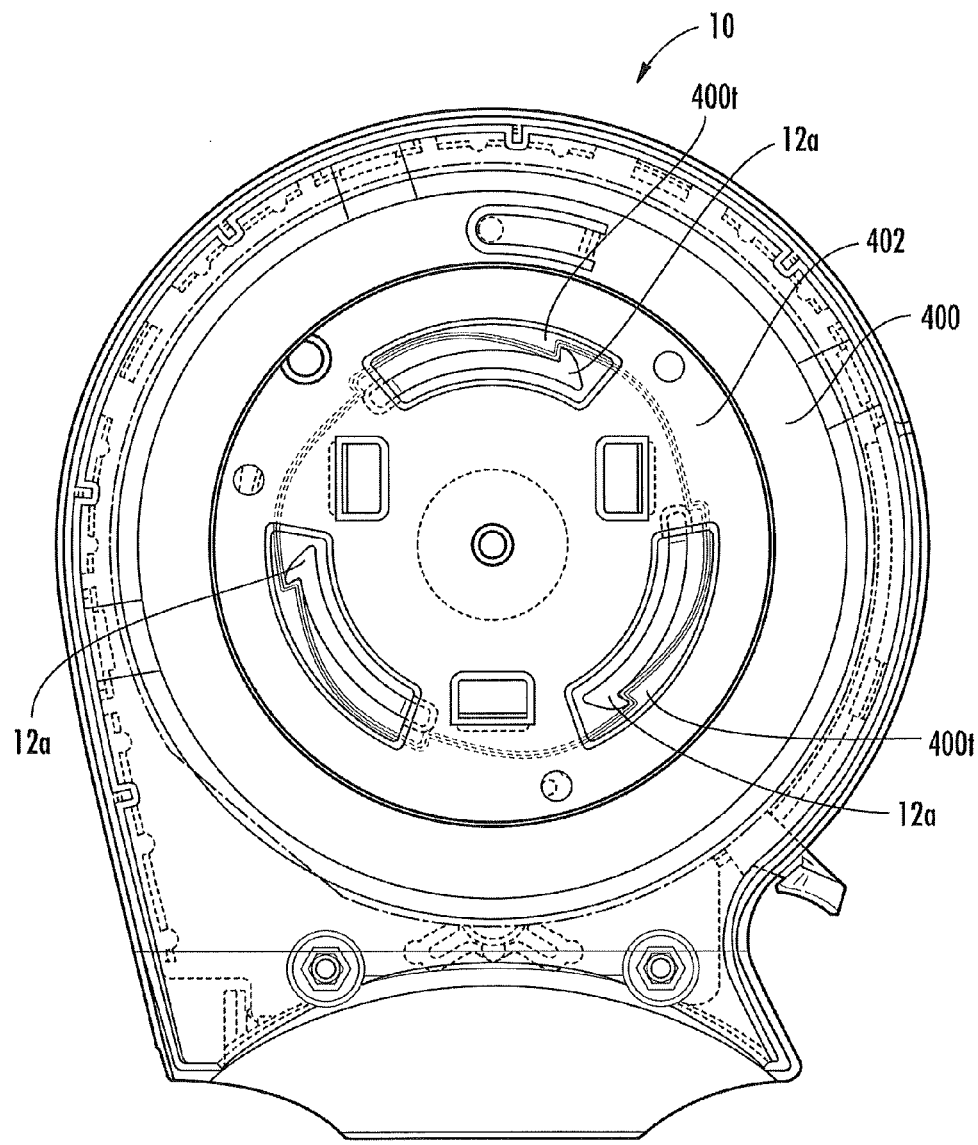
FIG. 11C is a top plan view of the inhaler of FIG. 10B with the cover 11 displayed transparently for clarity and illustrating ratchet arms in the cover that cooperate with teeth in the ramp disk.
Figure 12A:
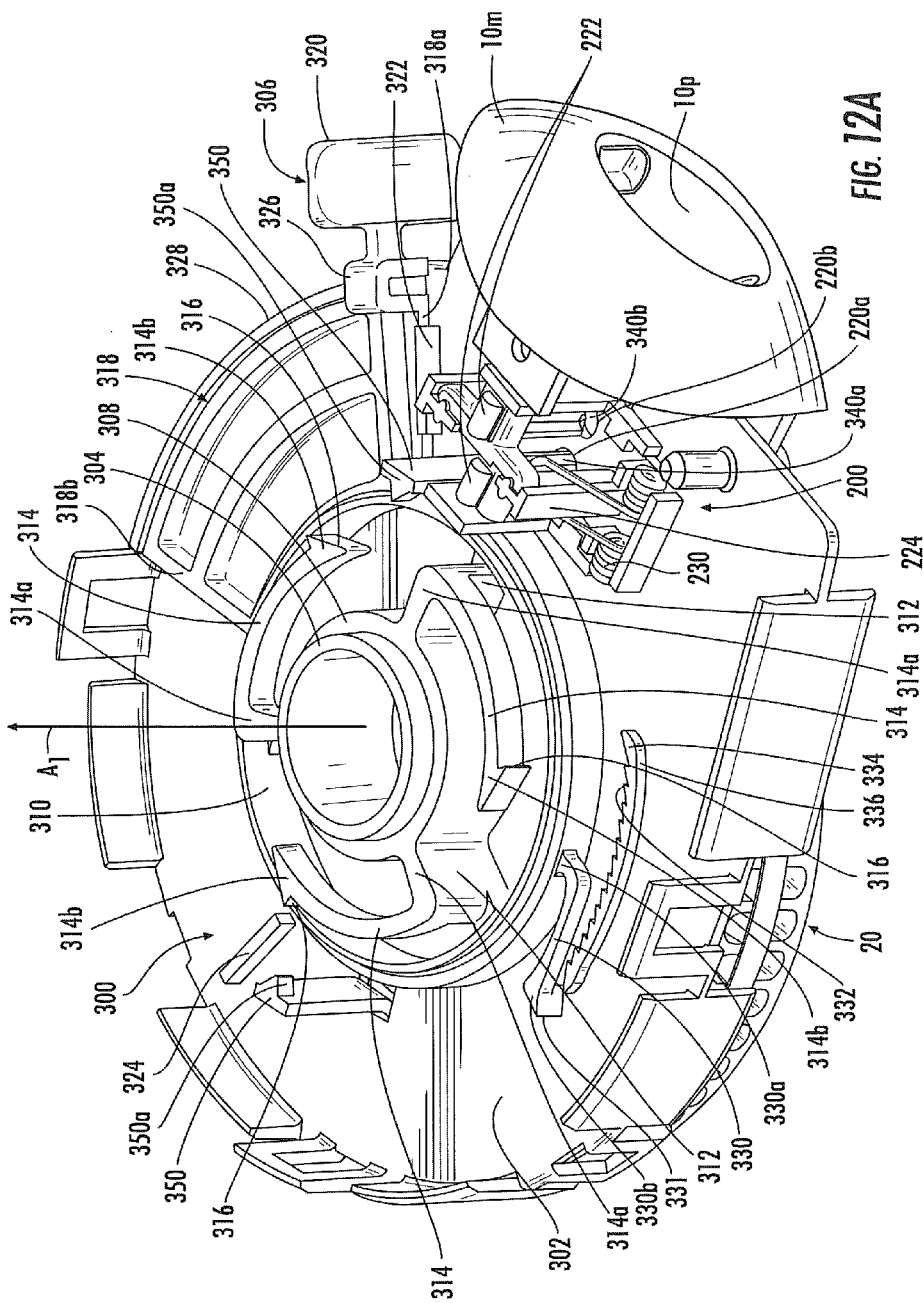
FIG. 12A is a top perspective view of the inhaler of FIG. 10A with the ramp disk removed therefrom, according to some embodiments of the present invention.
Figure 13A:
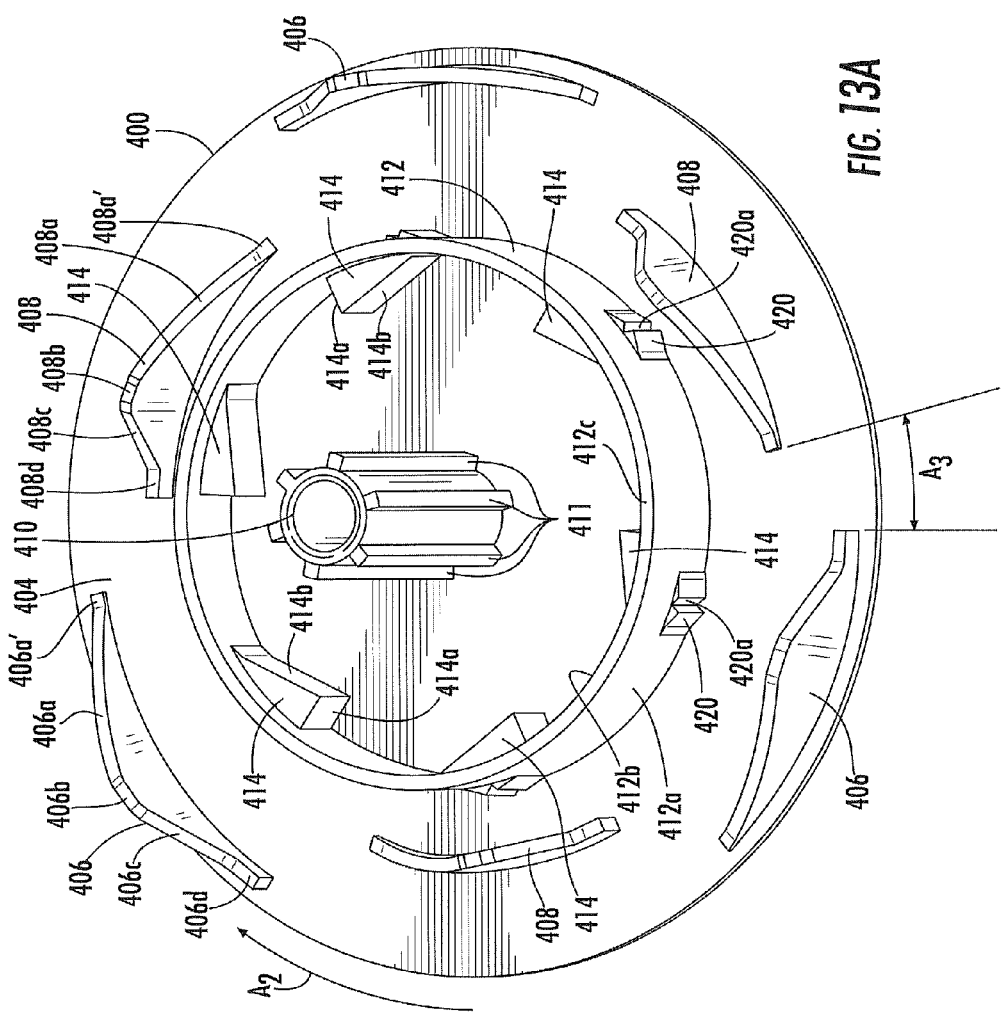
FIG. 13A is a bottom perspective view of the ramp disk of the inhaler of FIG. 10A, according to some embodiments of the present invention.
Figure 13B:
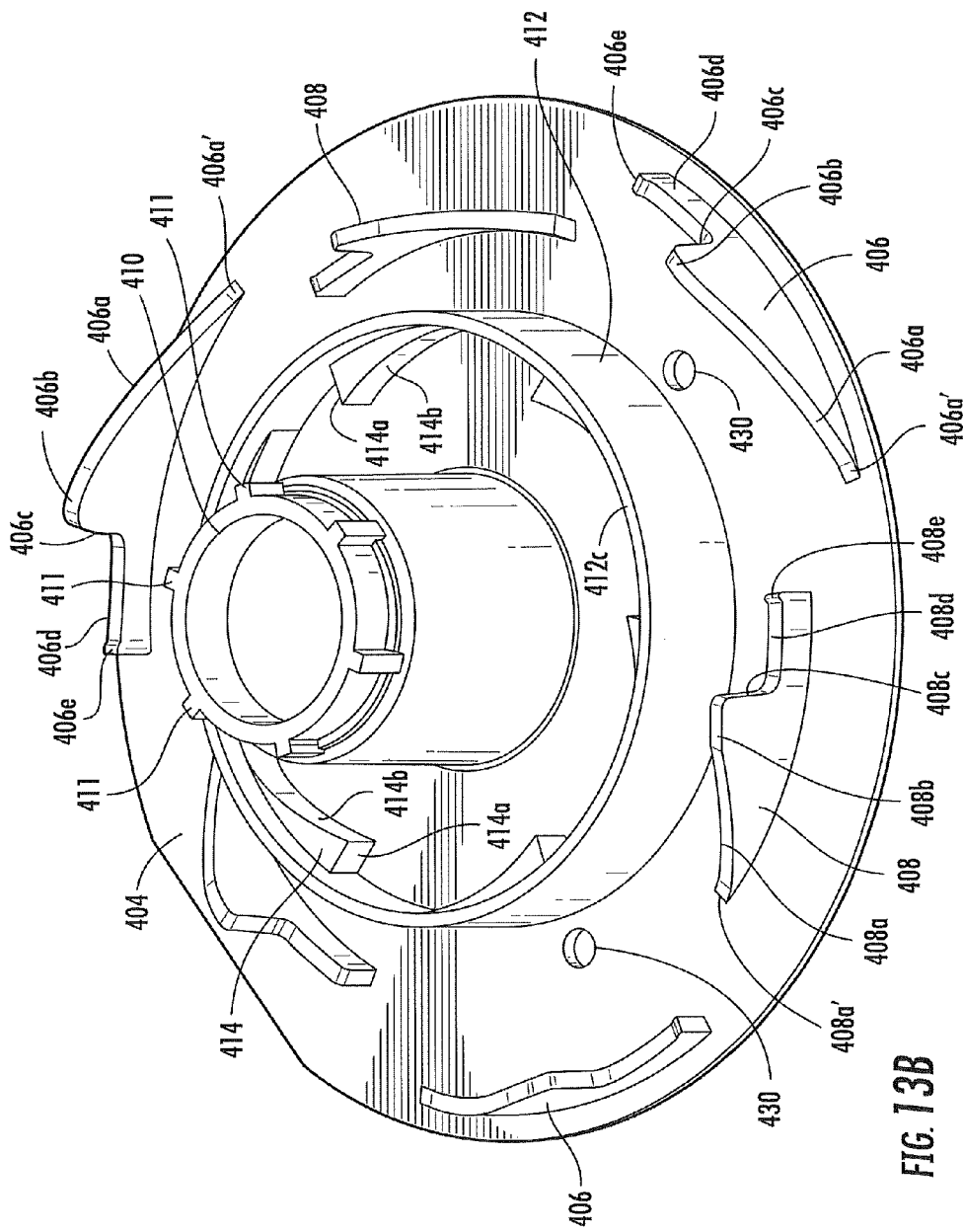
FIG. 13B is a bottom perspective view of the ramp disk of the inhaler of FIG. 10B, according to some embodiments of the present invention.
Figure 13C:
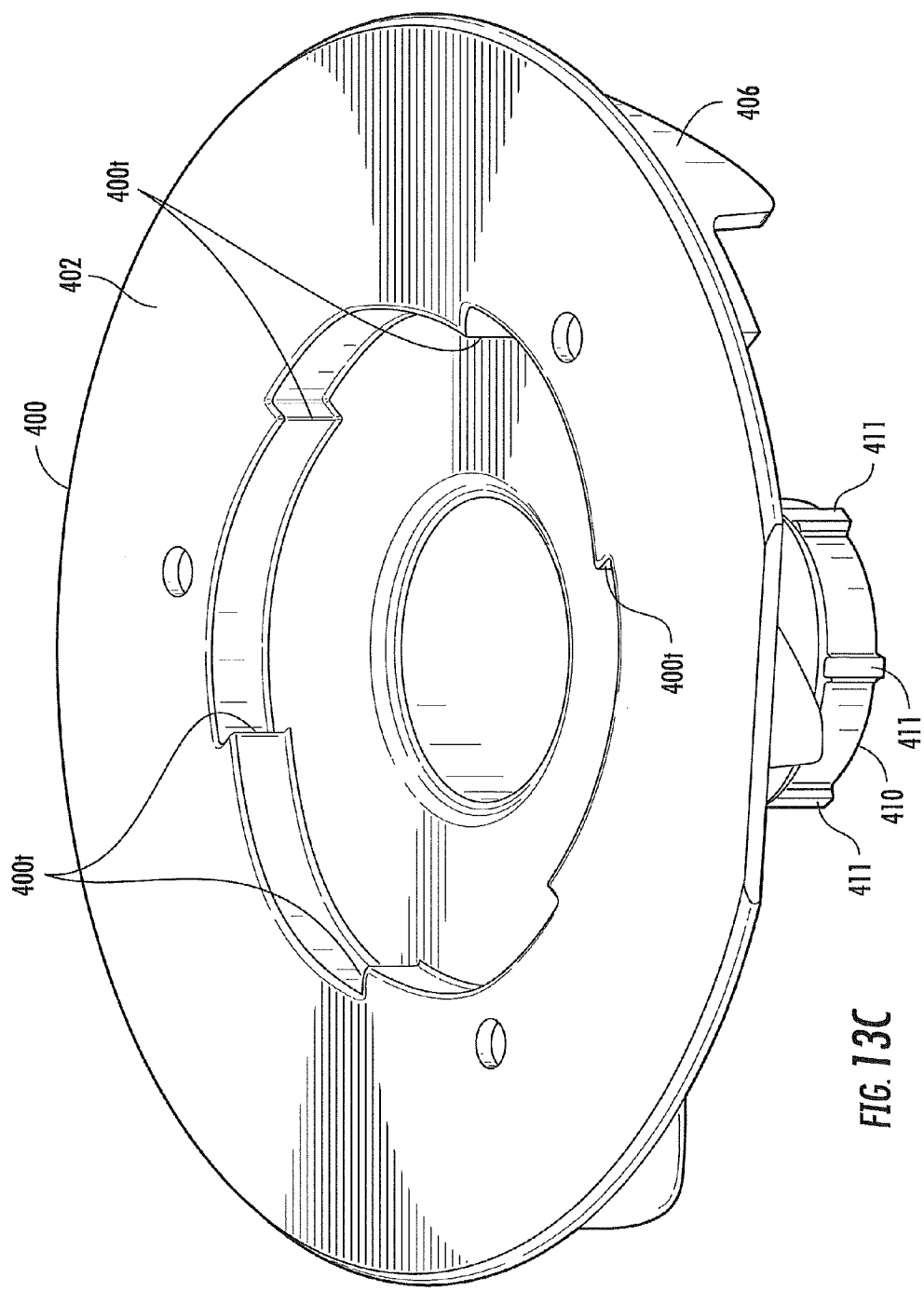
FIG. 13C is a top perspective view of the ramp disk of FIG. 13B, according to some embodiments of the present invention.

FIG. 11B is a top perspective view of the inhaler of FIG. 10B with the cover 11 and upper and lower housing portions 12, 13 removed and illustrating the ramp disk 400 of FIGS. 13B and 13C. FIG. 11C is a top plan view of the inhaler of FIG. 10B, with the cover 11 displayed transparently and with some elements displayed in broken line for clarity, and illustrating ratchet arms 12a in the upper housing portion 12 cooperating with teeth 400t in the first side 402 of the ramp disk 400. The cooperation of ratchet arms 12a and teeth 400t serve an anti-backup function similar to that described with respect to backup posts 350 and catches 420, illustrated in FIGS. 12A and 13A, which prevent backward rotation of the ramp disk 400, as described below.

FIG. 12A is a top perspective view of the piercing frame 300 for the inhaler 10 of FIG. 10A with the ramp disk 400 removed therefrom for ease of discussion and clarity. As shown, the piercing frame 300 has a substantially planar surface 302 with a centrally located, upwardly extending post 304. A user-accessible actuator mechanism 306 that is configured to rotate the ramp disk 400, as will be described below, is rotatably secured to the piercing frame 300. The illustrated actuator mechanism 306 includes first and second ring members 308, 310 connected by radially extending members 312 so as to be substantially concentric. The first ring member 308 is rotatably coupled to the post 304 such that the actuator mechanism 306 rotates about axis $A_1$ between a first position (FIG. 1B) and a second position (FIG. 1C), as will be described below.

The actuator mechanism 306 includes a plurality of spaced-apart, arcuate arms 314 positioned between the first and second ring members 308, 310, as illustrated in FIG. 12A. Each arcuate arm 314 has a proximal end 314a secured to the first ring 308 and a distal free end 314b. The distal free end 314b of each arcuate arm 314 includes a pawl 316 that is configured to engage spaced-apart step members 414 (FIG. 13A) on the ramp disk 400 to cause one way rotation of the ramp disk 400, as will be described below.

The illustrated actuator mechanism 306 also includes an arcuate body portion 318 that extends radially outward from the second ring member 310. The arcuate body portion 318 includes user lever 320 that extends outwardly from the inhaler so as to be gripped by a user of the inhaler 10. A user moves the actuator mechanism 306 from a first position to a second position via lever 320 to rotate the ramp disk 400 and pierce a dose container 30c, as will be described below. The configuration of the actuator mechanism 306 allows for a relatively short stroke (e.g., 60°) of the lever 320 from the first position (FIG. 1B) to the second position (FIG. 1C).

The actuator mechanism body portion 318 is configured to slide along the piercing frame surface 302 as the actuator mechanism 306 is moved between first and second positions. The piercing frame 300 includes first and second blocking members 322, 324 that extend upwardly from the piercing frame surface 302 and that are configured to limit the rotational movement of the actuator mechanism 306. For example, when the actuator mechanism 306 is in the first position, end 318a of the arcuate body portion 318 abuts blocking member 322. When the actuator mechanism 306 is moved to the second position, end 318b of the arcuate body portion 318 abuts blocking member 324.

In the illustrated embodiment, the illustrated body portion 318 includes a U-shaped guide 326 that slides along a rail 328 associated with the piercing frame 300. The guide 326 and rail 328 are designed to facilitate smooth sliding operation of the actuator mechanism 306 between the first and second positions. In addition, the U-shaped guide 326 and rail 328 can be configured to block the ingress of foreign material into the inhaler 10, and also to block the visibility of internal components of the inhaler 10.

Figure 16A:
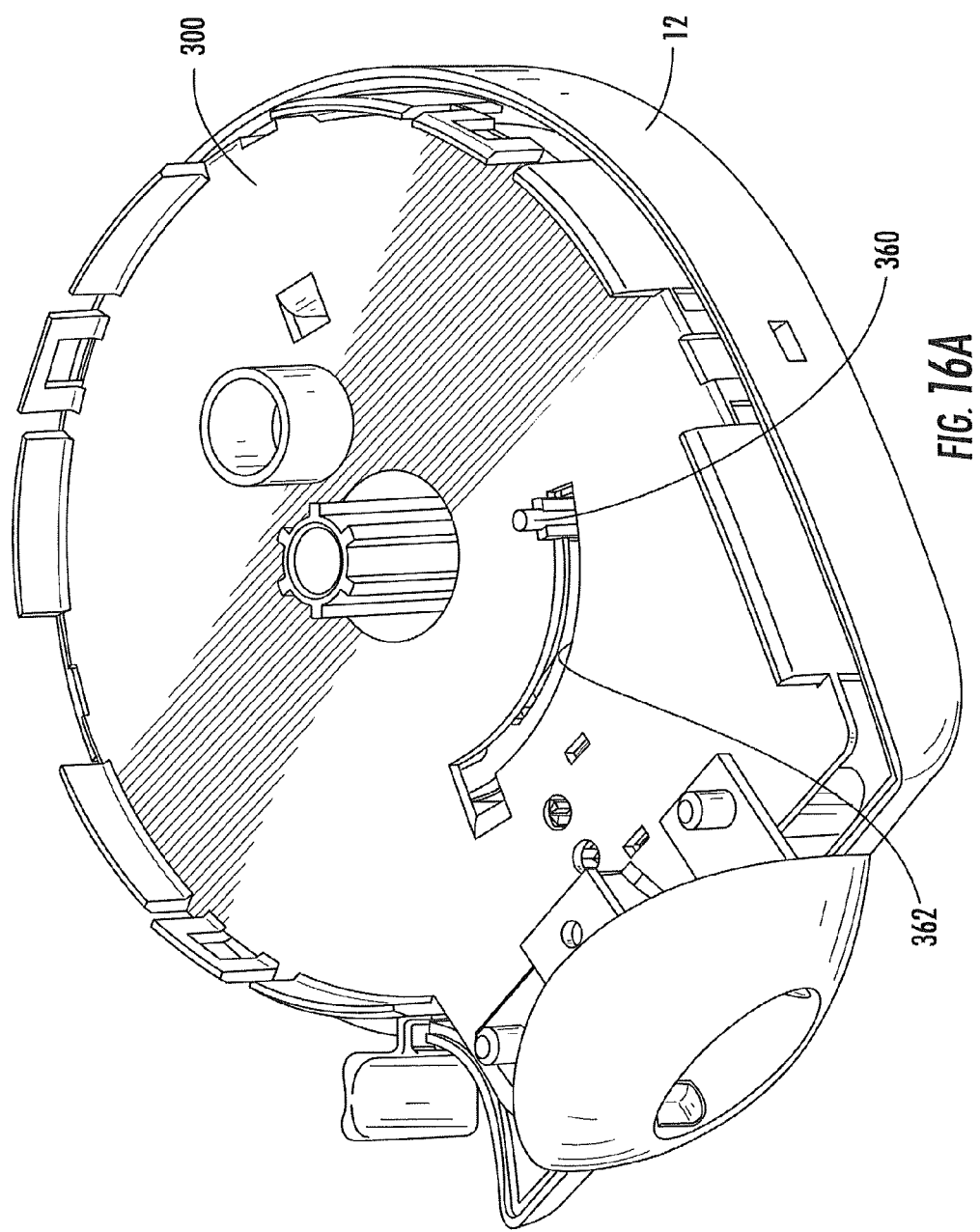
FIG. 16A is a bottom, cutaway perspective view of the inhaler of FIG. 10A illustrating a dose disk biasing post associated with the user-accessible actuator for biasing the dose disk toward the mouthpiece, according to some embodiments of the present invention.

The actuator mechanism 306 can also include a dose container assembly biasing post 360, as illustrated in FIG. 16A. The post 360 extends downwardly from the second ring member 310 of the actuator mechanism 306 and through an arcuate slot 362 formed in the piercing frame 300. The biasing post 360 is configured to make contact with a tab 530 on an indexing arm 510 of the indexing frame 508 (FIG. 10A) when the actuator mechanism 306 is moved to the second position. The biasing post 360 causes the tab 530 to flex against the inner perimeter of the dose container assembly 20 so as to urge the dose container assembly 20 toward the mouthpiece 10m for a tight interface with the dose container assembly 20 during inhalation.

Figure 15A:
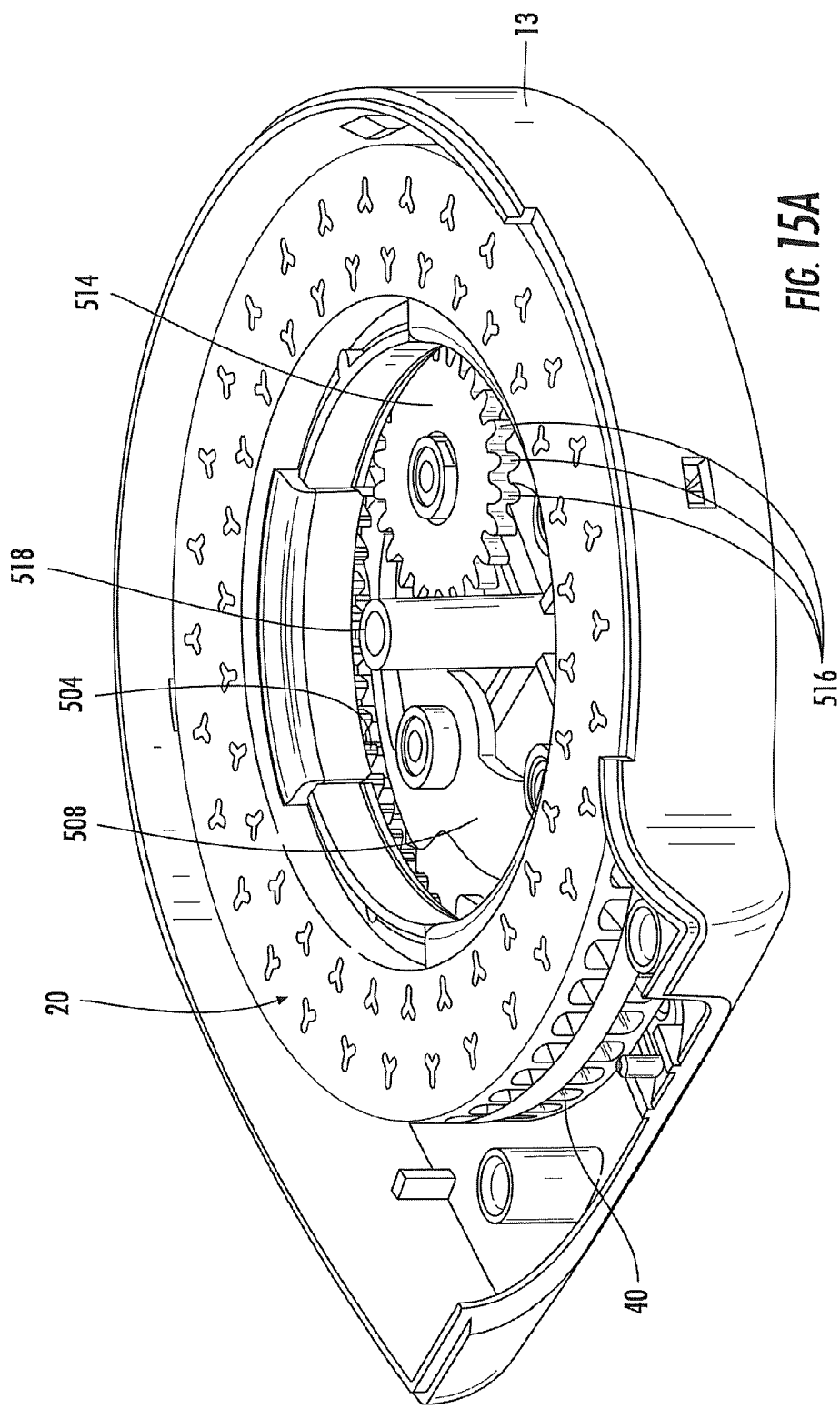
FIG. 15A is a top, cutaway perspective view of the inhaler of FIG. 10A illustrating the dose disk indexing mechanism in relation to a dose container assembly, according to some embodiments of the present invention.
Figure 16B:
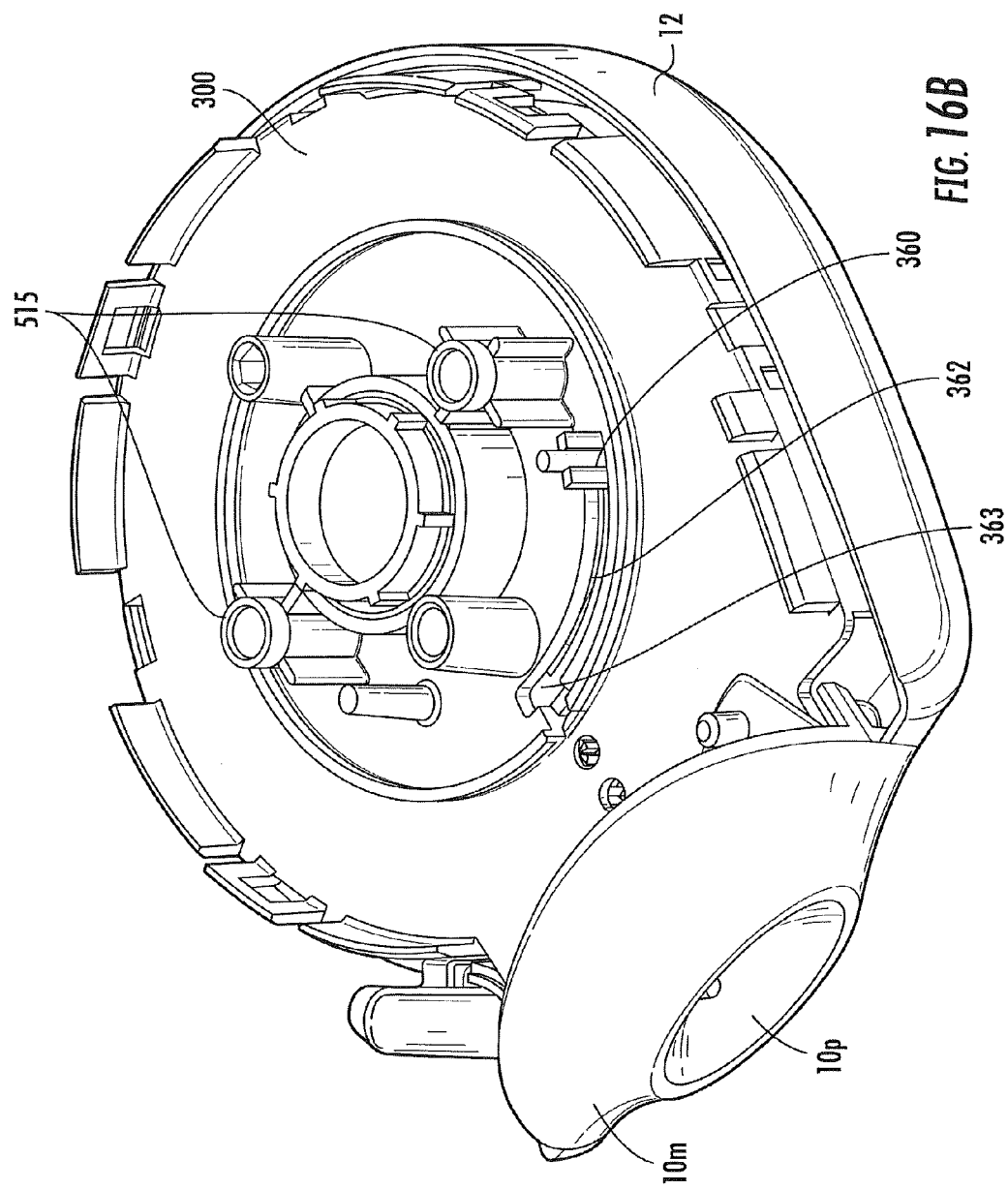
FIG. 16B is a bottom, cutaway perspective view of the inhaler of FIG. 10B illustrating a dose disk biasing post associated with the user-accessible actuator for biasing the dose disk toward the mouthpiece, according to some embodiments of the present invention.

FIGS. 15B and 16B illustrate an alternate embodiment of a biasing mechanism that can bias the disk assembly 20 toward the mouthpiece 10m of the inhaler 10 of FIG. 10B during inhalation then releasing or disengaging to allow rotation of the disk assembly 20 for indexing. As discussed above, in some embodiments, the inhaler 10 can be configured to rotate the disk assembly 20 a defined angular rotation, such as about 6 degrees, to serially dispense or access dose containers alternately on inner and outer rows. This biasing mechanism can be configured to operate with the lever 320 similar to that discussed above, but may also be activated using other components or features.

As shown in FIG. 16B, the biasing mechanism can include a post 360 that resides proximate an inner perimeter of the dose container disk assembly 20. The post 360 can reside in a circumferentially extending slot 362 having an end portion that merges into a slot portion 363 that extends radially outward toward the inner perimeter of the dose disk assembly 20. During and/or just prior to release of the medicament to a user for inhalation (e.g., "dosing"), the post 360 travels in slot 362 until it reaches slot portion 363 and pushes (typically indirectly) against the inner perimeter of the disk assembly 20 to bias the disk assembly 20 toward the mouthpiece 10m.

In some embodiments, the post 360 can communicate with a stationary post 360a on the indexing frame 508 (FIG. 15B). In the embodiment shown, the biasing post 360 is configured to contact and push against post 360a causing post 360a to flex radially outward against the dose container assembly 20. The two posts 360, 360a can be configured to project toward each other, one upwardly and one downwardly, with the post 360a typically residing closer to an inner perimeter of the dose disk assembly 20.

The post 360 is typically attached to or in communication with the lever 320 which is accessible by a user. However, the post 360 can be in communication with other mechanisms that cause the post 360 to move in the slot 362 and bias the disk assembly 20 toward the mouthpiece 10m. As shown in FIG. 15B, the indexing frame 508 can reside under gears 514 that are associated with the indexing mechanism 500. The rotatable gears 514 can be held on mounts 515 on the piercing frame member 300 as shown in 15C. Generally stated, the gears 514 communicate with teeth 411 on indexing post 410 (that can be part of the ramp disk 400) and gear teeth 504 on the disk assembly 20 (e.g., as shown, on the lower disk 40). Turning the indexing post 410 turns gears 514 which, in turn, indexes the disk assembly 20. The other gear teeth 502 (residing closer to the bottom of the inhaler housing) can communicate with indexing control arms 512 on the indexing frame 508 as shown in FIG. 14C which can help more precisely turn the dose container assembly a desired rotational amount.

Referring back to FIG. 12A, an arm 330 extends outwardly from the second ring member 310, as illustrated. The arm 330 includes a proximal end 330a attached to the second ring member 310 and a distal free end 330b. The distal free end 330b includes a pawl 331 extending therefrom that engages teeth 332 in a rack 334 attached to the piercing frame 300. The pawl 331 allows the actuator mechanism 306 to be moved by a user only in one direction from the first position to the second position. The pawl 331 prevents backward movement of the actuator mechanism (i.e., in a direction toward the first position) until the actuator mechanism 306 reaches the second position. When the actuator mechanism 306 reaches the second position, the pawl 331 disengages from the teeth 332 of the rack 334 and the actuator mechanism 306 is free to move back to the first position while the arm 330 travels over the rack 334. The actuator mechanism 306 is moved back to the first position as a result of a user closing the cover 11 of the inhaler 10.

In some embodiments, when the pawl 331 is engaged with teeth 332 in the rack 334 as the actuator mechanism 306 is moved from the first position to the second position, the distal free end 330b of arm 330 is urged inwardly toward the second ring member 310. When the pawl 331 disengages from the teeth 332, the distal free end 330b biases outwardly. The distal free end 330b of arm 330 has a tapered configuration such that when the free end 330b biases outwardly, the tapered configuration causes the free end 330b to slide along an outside wall 336 of the rack 334 such that the pawl 331 cannot engage any of the teeth 332 when the actuator mechanism 306 is returned to the first position. When the actuator mechanism 306 is in the first position, the tapered configuration of the distal free end 330b of arm 330 causes the pawl 331 to again become engaged with the teeth 332 of the rack 334 such that the pawl 331 prevents backward movement of the actuator mechanism 306 between the first and second positions.

Still referring to FIG. 12A, the reciprocating dual piercing mechanism 200 includes an inner or first piercing member 220a and an outer or second piercing member 220b in adjacent, spaced-apart relationship. Each piercing member 220a, 220b is configured to reciprocally move between a retracted position and an extended piercing position independently of the other. The piercing members 220a, 220b are movably secured to a support structure 224 that extends upwardly from the piercing frame 300, as illustrated. A pair of apertures 340a, 340b are formed through the piercing frame surface 302, as illustrated. Each aperture 340a, 340b is in alignment with, a respective row of dose containers 30c in the dose container assembly 20. As the dose container assembly 20 is indexed during use, a respective dose container 30c in at least one row is positioned under a respective aperture 340a, 340b such that a respective piercing member 220a, 220b can pierce the upper and lower sealant layers 36, 37 of the dose container 30c.

A biasing element 230, such as a torsion spring, is secured to the piercing frame 300 and contacts each piercing member 220a, 220b and during operation is configured to urge each piercing member 220a, 220b to a retracted position. Although illustrated as a single biasing element 230, more than one biasing element may be utilized, for example, one or more separate biasing elements for each piercing member 220a, 220b may be utilized. The configuration of the piercing mechanism 200 can allow more flexibility for the design of the spring 230. For example, the spring 230 is not required to be positioned under the piercing members 220a, 220b, but can reside laterally or radially spaced apart from the piercing members 220a, 220b. As such, a device with less height requirements than conventional inhaler devices can be achieved.

Each elongate piercing member 220a, 220b includes a distal piercing portion 221 (FIG. 10A) and a proximal end 222. In some embodiments, the distal piercing portion 221 can be a corkscrew piercer configured to pierce the sealants 36, 37 of a dose container 30c with a straight vertical non-rotational movement, as illustrated and described with respect to FIGS. 19A-19B, below. In some embodiments, the distal piercing portion 221 can be a fluted piercer configured to pierce the sealants 36, 37, as illustrated and described with respect to FIGS. 18C-18F. Various types of piercers and various piercer configurations may be utilized in accordance with embodiments of the present invention, without limitation.

As will be described below, in some embodiments each piercing member 220a, 220b partially retracts from a dose container 30c during a portion of the operation of the inhaler 10 so as to plug the aperture 55 of the upper disk 50 of the inhaler 10 during and/or after drug release/inhalation.

As shown in FIG. 12A, in some embodiments, the piercing frame 300 also includes a pair of anti-backup posts 350 in opposing relationship. Each illustrated anti-backup post 350 includes a radially inwardly extending tooth 350a at the post free end, as illustrated. The tooth 350a of each anti-backup post 350 is configured to engage a catch 420 (FIG. 13A) on the ramp disk 400 and prevent backward rotation of the ramp disk 400, as described below.

Figure 12B:
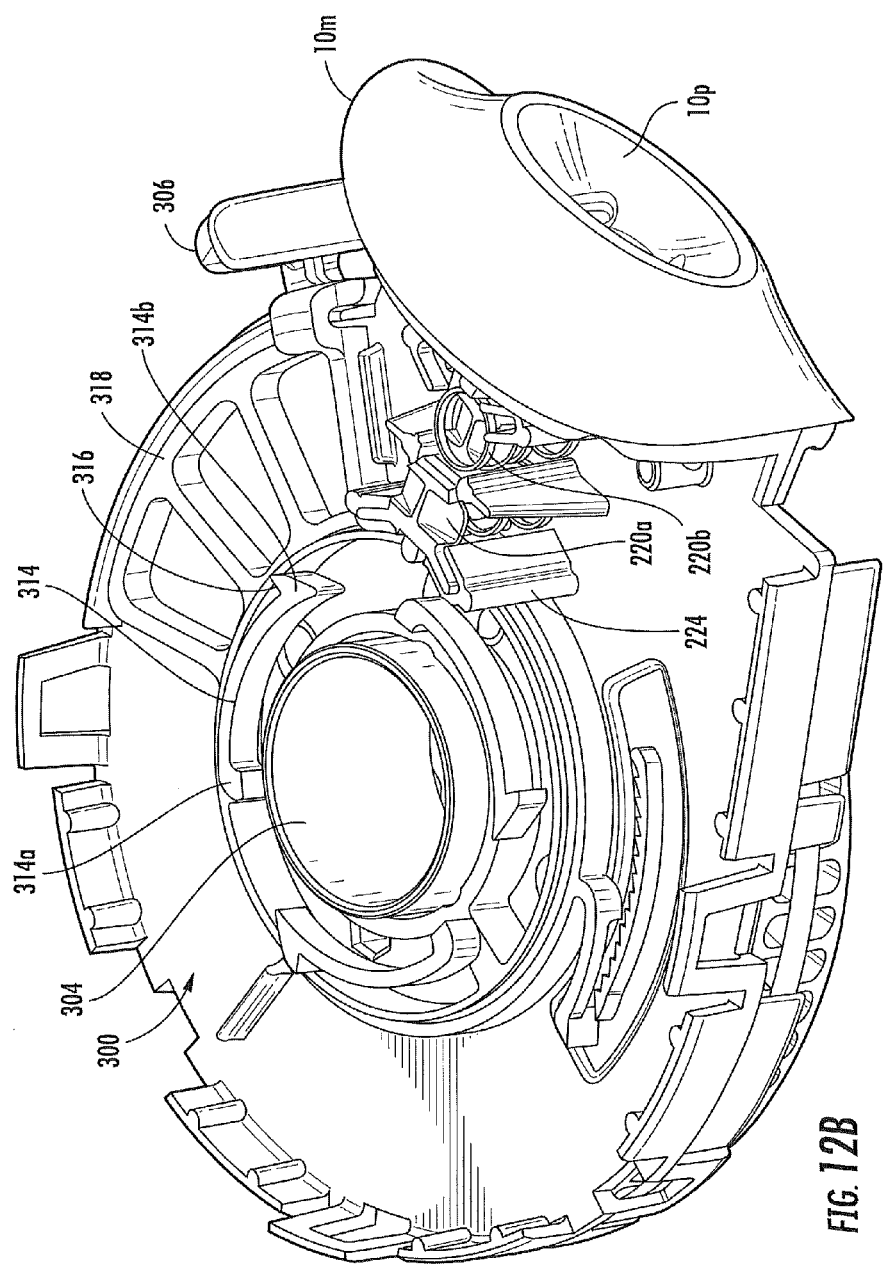
FIG. 12B is a top perspective view of the inhaler of FIG. 10B with the ramp disk removed therefrom, according to some embodiments of the present invention.

FIG. 12B is a top perspective view of the piercing frame 300 for the inhaler 10 of FIG. 10B with the ramp disk 400 removed therefrom for ease of discussion and clarity, according to other embodiments of the present invention. The illustrated piercing frame 300 of FIG. 12B does not include the pair of anti-backup posts 350 illustrated in FIG. 12A. Otherwise, the piercing frame 300 of FIG. 12B is substantially similar in construction and functionality to the piercing frame 300 of FIG. 12A.

Referring now to FIG. 13A, a bottom perspective view of the ramp disk 400 for the inhaler 10 of FIG. 10A is illustrated. The ramp disk 400 includes opposite first and second surfaces or sides 402, 404 (FIG. 11A). The ramp disk 400 includes first and second sets of ramp elements 406, 408 that extend outwardly from the second side 404 in staggered, concentric relationship. The ramp disk 400 also includes an indexing post 410 that extends outwardly from a central portion of the second side 404. In addition, a ring member 412 extends outwardly from the second side 404 between the second set of ramp elements 408 and the indexing post 410.

The ramp elements 406, 408 are typically substantially identical in configuration, and each have a substantially curvilinear configuration, as illustrated. Each first (outer) ramp element 406 includes a first inclined portion 406a, a plateau portion 406b, a second inclined portion 406c, and a shelf portion 406d. Similarly, each second (inner) ramp element 408 includes a first inclined portion 408a, a plateau portion 408b, a second inclined portion 408c, and a shelf portion 408d. The first set of ramp elements 406 are configured to engage a proximal end 222 of the outer piercing member 220b and move (push) the outer piercing member 220b between retracted and extended (piercing) positions as the ramp disk 400 is rotated in the direction indicated by arrow $A_2$. The second set of ramp elements 408 are configured to engage a proximal end 222 of the inner piercing member 220a and move (push) the inner piercing member 220a between retracted and extended (piercing) positions as the ramp disk 400 is rotated in the direction indicated by arrow $A_2$. The inner ramp elements 408 are spaced apart from each other by about one hundred twenty degrees (120°). Similarly, the outer ramp elements 406 are spaced apart from each other by about one hundred twenty degrees (120°).

The first and second sets of ramp elements 406, 408 are angularly separated by an angle indicated as $A_3$. In some embodiments, angle $A_3$ may be between about five degrees and fifteen degrees (5°-15°). In some embodiments, angle $A_3$ may be about eight degrees (8°). Indexing of the dose container assembly 20 (i.e., rotation of the dose container assembly 20 to position a medicament-containing dose container 30c beneath a piercing member 220a, 220b) occurs within this increment indicated by $A_3$. That is, indexing of the dose container assembly 20 occurs when neither ramp elements 406, 408 are in contact with a respective piercing member

220a, 220b. Typically, the dose container assembly 20 cannot be properly indexed (rotated) if a piercing member resides in a dose container 30c.

The ring member 412 that extends outwardly from ramp disk side 404 includes an outer surface 412a and an inner surface 412b, and an end portion 412c. A diameter of the ring member 412 and a diameter of the second ring member 310 of the actuator mechanism 306 (FIG. 12A) are substantially the same. Thus, in some embodiments, the end portion 412c of the ramp disk ring member 412 is in contacting relationship with the outer ring member 310 of the actuator mechanism 306 within the inhaler 10.

A plurality of spaced-apart step members 414 extend radially inwardly from the ring member inner surface 412b, as illustrated in FIG. 13A. Each step member 414 includes an end 414a and a tapered portion 414b extending away from the end 414a. Each end 414a of a step member 414 is configured to be engaged by a pawl 316 at the free end 314b of an arcuate arm 314 of the actuator mechanism 306 (FIG. 12A). The tapered portion 414b of each step member 414 allows the pawl 316 to slide along the step member 414 and engage the end 414a. User movement of the actuator mechanism 306 from the first position to the second position causes the ramp disk 400 to rotate along the direction indicated by arrow $A_2$.

Movement of a piercing member 220a, 220b by a respective ramp element 408, 406 will now be described with respect to a first ramp element 406 and the outer piercing member 220b. Each of the first and second ramp elements 408, 406 cause the same movement of respective piercing members 220a, 220b. When a user opens the cover 11 of the inhaler 10 to the position indicated in FIG. 1B, the actuator mechanism 306 is in the first position. When the actuator mechanism 306 is in the first position, a proximal end 222 of piercing member 220a is in contact with a shelf portion 408d of a ramp element 408. As the ramp disk 400 is rotated via user movement of the actuator mechanism 306 in the direction indicated by arrow $A_2$ (i.e., from the first position to the second position), the proximal end 222 of piercing member 220a no longer contacts the shelf portion 408d, and the piercing member 220a is fully retracted. The dose container assembly 20 is also indexed to the next dose container 30c during the rotation indicated by angle $A_3$ via the rotation of the indexing post 410. The first inclined portion 406a of the ramp element 406 then contacts the proximal end 222 of piercing member 220b and extends the piercing member 220b into a dose container 30c. Upon continued movement of the actuator mechanism 306, the plateau portion 406b is in contact with the piercing member proximal end 222 and the piercing member 220b is at maximum depth within a dose container 30c. Continued movement of the ramp disk 400 causes the piercing member proximal end 222 to follow the second inclined portion 406c under the force of spring 230 such that the piercing member 220b retracts from the dose container 30c.

When the actuator mechanism reaches the second position, the proximal end 222 of piercing member 220b is in contact with the shelf portion 406d, which causes the piercing member 220b to remain partially within the aperture 55 of the upper airway disk 50 so as to prevent medicament from falling out of the open dose container 30c prior to inhalation by a user, as described above with respect to FIGS. 7A-7C. The piercing member proximal end 222 remains in contact with the shelf portion 406d of the first ramp element 406 as the cover 11 of the inhaler 10 is returned to the closed position.

The indexing post 410 includes a plurality of spaced apart ribs 411 extending radially outward from the indexing post, as illustrated in FIG. 13A. As described below with respect to FIGS. 14A and 15A, these indexing post ribs 411 are configured to engage and cause rotation of an idler gear 514 (FIG. 14A) that is operably associated with the indexing mechanism 500. The ramp disk 400 is particularly advantageous because the ramp elements 406, 408 that cause piercing and the indexing post 410 that causes dose container assembly indexing are located on the same inhaler component. As such, the timing of dose container piercing and dose container assembly indexing is properly maintained at all times.

The illustrated ramp disk ring member 412 includes a plurality of anti-backup catches 420 extending from the outer surface 412a thereof in circumferentially spaced-apart relationship. Each catch 420 includes a recess 420a that is configured to engage a tooth 350a of an anti-backup post 350 on the piercing frame. This engagement of an anti-backup post tooth 350a within a catch recess 420a prevents the ramp disk 400 from rotating in a direction opposite to that indicated by arrow $A_2$ (i.e., prevents the ramp disk from being rotated in the wrong direction, particularly when pawl 316 is deflecting over tapered portion 414b).

Referring now to FIG. 13B, a bottom perspective view of the ramp disk 400 for the inhaler 10 of FIG. 10B is illustrated. The ramp disk 400 is substantially similar in construction and functionality to the ramp disk 400 of the inhaler 10 of FIG. 10A. The ramp disk 400 includes opposite first and second surfaces or sides 402 (FIG. 13C), 404, and includes first and second sets of ramp elements 406, 408 that extend outwardly from the second side 404 in staggered, concentric relationship, as described above with respect to FIG. 13A. However, the first and second sets of ramp elements 406, 408 of FIG. 13B have a slightly different configuration than the first and second sets of ramp elements 406, 408 of FIG. 13A. Each first (outer) ramp element 406 includes a first inclined portion 406a, a plateau portion 406b, and a shelf portion 406d similar to the ramp element 406 of FIG. 13A. However, second inclined portion 406c is substantially more steeply inclined in FIG. 13B than the second inclined portion 406c of FIG. 13A. This steeper incline facilitates faster movement of the piercing member 220b from an extended (piercing) position to a partially retracted position. In addition, ramp element 406 of FIG. 13B includes a raised portion 406e that is configured to prevent the piercing member 220b from slipping off the shelf portion 406d.

Similarly, each second (inner) ramp element 408 of FIG. 13B includes a first inclined portion 408a, a plateau portion 408b, and a shelf portion 408d similar to the ramp element 408 of FIG. 13A. However, second inclined portion 408c is substantially more steeply inclined in FIG. 13B than the second inclined portion 408c of FIG. 13A. This steeper incline facilitates faster movement of the piercing member 220a from an extended (piercing) position to a partially retracted position. In addition, ramp element 408 of FIG. 13B includes a raised portion 408e that is configured to prevent the piercing member 220a from slipping off the shelf portion 408d.

The indexing post 410 includes a plurality of spaced apart ribs 411 extending radially outward from the indexing post, as illustrated in FIG. 13B. These indexing post ribs 411 are configured to engage and cause rotation of a pair of idler gears 514 (FIG. 14C) that is operably associated with the indexing mechanism 500.

The illustrated ramp disk 400 of FIG. 13B includes alignment apertures 430 extending through the ramp disk 400 from the first side 402 to the second side 404. These apertures 430 can facilitate automated assembly and alignment of the ramp disk 400 in the inhaler 10. In addition, because the inhaler 10 of FIG. 10B does not include anti-backup posts 350, as illustrated in FIG. 12A, the ramp disk 400 of FIG. 13B does not include a plurality of anti-backup catches extending from the outer surface 412a of ring member 412.

FIG. 13C is a top perspective view of the ramp disk 400 of FIG. 13B that illustrates teeth 400t in the first side 402 thereof. Ratchet arms 12a in the upper housing portion 12 of the inhaler 10 of FIG. 10B are configured to engage the teeth 400t and prevent backward rotation of the ramp disk 400 similar to the function of the backup posts 350 and catches 420 of FIGS. 12A and 13A.

FIG. 14A is a bottom, cutaway perspective view of the inhaler of FIG. 10A illustrating the dose disk indexing mechanism 500. The lower disk 40 of the dose container assembly 20 includes first and second sets of inner perimeter gear teeth 502, 504 in vertically stepped relationship, as illustrated. The lower disk 40 also includes a spiral-shaped groove 506 that extends circumferentially around the disk 40, as illustrated. An indexing frame 508 includes a plurality of arcuate indexing arms 510 circumferentially spaced-apart, as illustrated in FIG. 14A. Each indexing arm 510 includes a free end 512 with a tooth 512a. The indexing frame 508 is positioned relative to the lower disk 40 such that a tooth 512a at the free end 512 of each indexing arm 510 engages with the first set of inner perimeter teeth 502. Indexing arms 510 serve as alignment members that assure exact positioning of a dose container 30c relative to apertures 340a, 340b in the piercing frame, and through which piercing members 220a, 220b are extended.

FIG. 14C is a bottom, cutaway perspective view of the inhaler of FIG. 10B illustrating the dose disk indexing mechanism 500. The indexing mechanism 500 is substantially similar in construction and function as the indexing mechanism 500 of the inhaler 10 of FIG. 10A with the exception that a pair of idler gears 514 are utilized. These idler gears 514 are engaged by and caused to rotate by indexing post ribs 411.

FIG. 14D is an enlarged, partial plan view of the inhaler of FIG. 14C illustrating a dose window 520 centered over dose indicia that indicates that 60 doses are remaining. FIG. 14E is an enlarged, partial plan view of the inhaler of FIG. 14C illustrating the dose window 520 centered over dose indicia that indicates that no (zero) doses are remaining. The dose window 520 includes a post extending therefrom that engages the spiral groove 506 in the lower disk 40. The groove 506 and post are configured to maintain the dose window 520 directly over the dose indicia on the lower disk surface 40a as the dose container assembly is indexed, as is described below.

Referring to FIG. 15A, the indexing frame 508 of the inhaler 10 of FIG. 10A is secured to the lower housing portion 13. An idler gear 514 is rotatably secured to the indexing frame 508 and is positioned such that the teeth 516 of the idler gear 514 engage the second set of inner perimeter teeth 504 of the lower disk 40. A centrally located post 518 extends upwardly from the lower housing portion 13 and is configured to receive the indexing post 410 of the ramp disk 400. The post 518 serves as an axis of rotation for the ramp disk 400. The indexing post ribs 411 are configured to engage the teeth 516 of the idler gear 514 when the post 518 is inserted within the indexing post 410.

To index the dose container assembly 20 by a predetermined amount, the ramp disk 400 is rotated via user movement of the actuator mechanism 306 via user lever 320 from the first position to the second position. Rotation of the ramp disk 400 causes the indexing post 410 to rotate which, in turn, causes rotation of the idler gear 514. Rotation of the idler gear 514 rotates the dose container assembly a predetermined amount via the second set of inner perimeter teeth 504 of the lower disk 40. According to some embodiments of the present invention, the actuator mechanism 306 is configured to rotate sixty degrees (60°). This correlates to six degrees (6°) of rotation of the dose container assembly 20 (i.e., 6° between a dose container in one row and a neighboring dose container in the other row).

The indexing mechanism 500, according to embodiments of the present invention, does not require dose container assemblies to have outer peripheral gear teeth. As such, smaller dose container assemblies can be utilized.

Referring back to FIG. 14A, the inhaler 10 includes a dose window 520 positioned above the bottom surface 40a of the lower disk 40. The dose window 520 is a separate component from the lower housing portion 13, and is configured to move relative to the lower housing portion 13. In some embodiments, the dose window 520 may be slidably attached to the lower housing portion 13. The dose window 520 includes an aperture 522 through which a user of the inhaler can view dose indicia 524 (FIG. 14B) on the lower disk surface 40a. The dose indicia 524 indicates the number of doses remaining in the inhaler 10. Alternatively, in some embodiments, the dose indicia 524 may indicate the number of doses that have already been consumed by the user of the inhaler 10. In some embodiments, the aperture 522 includes a transparent cover or lens to prevent the ingress of foreign material and/or to facilitate viewing the dose indicia 524. In some embodiments, a magnifying lens may be utilized to facilitate user viewing of dose indicia 524.

The dose window 520 also includes a post 526 extending therefrom that engages the spiral groove 506 in the lower disk 40. The groove 506 and post 526 are configured to maintain the aperture 522 directly over the dose indicia on the lower disk surface 40a as the dose container assembly is indexed. As illustrated in FIG. 14B, the dose container assembly includes sixty doses and dose indicia 524 includes the numbers zero to sixty (0-60). Because of the geometry of the dose container assembly, a dose container 30c is located every six degrees (6°) therearound. As such, the numbers "0" and "60" overlap. In order to properly show sixty (60) doses remaining when the inhaler is first used and to properly show zero (0) doses remaining when all of the doses in the inhaler have been consumed, the dose indicia 524 is displayed on the lower disk surface 40a in a spiral configuration: The spiral groove 506 in the lower disk surface 40a matches the spiral configuration of the dose indicia 524. As such, as the dose container assembly 20 is indexed, the post 526 engaged within the spiral groove 506 maintains the window aperture 522 centered over the dose indicia 524 at all times.

The post 526 also serves another important function. When all of the doses within the inhaler 10 have been consumed, the post abuts the end of the spiral groove 506 such that the dose container assembly 20 cannot be indexed further. As such, the post 526 serves as an "end of life" stop for the inhaler 10.

Figure 15C:
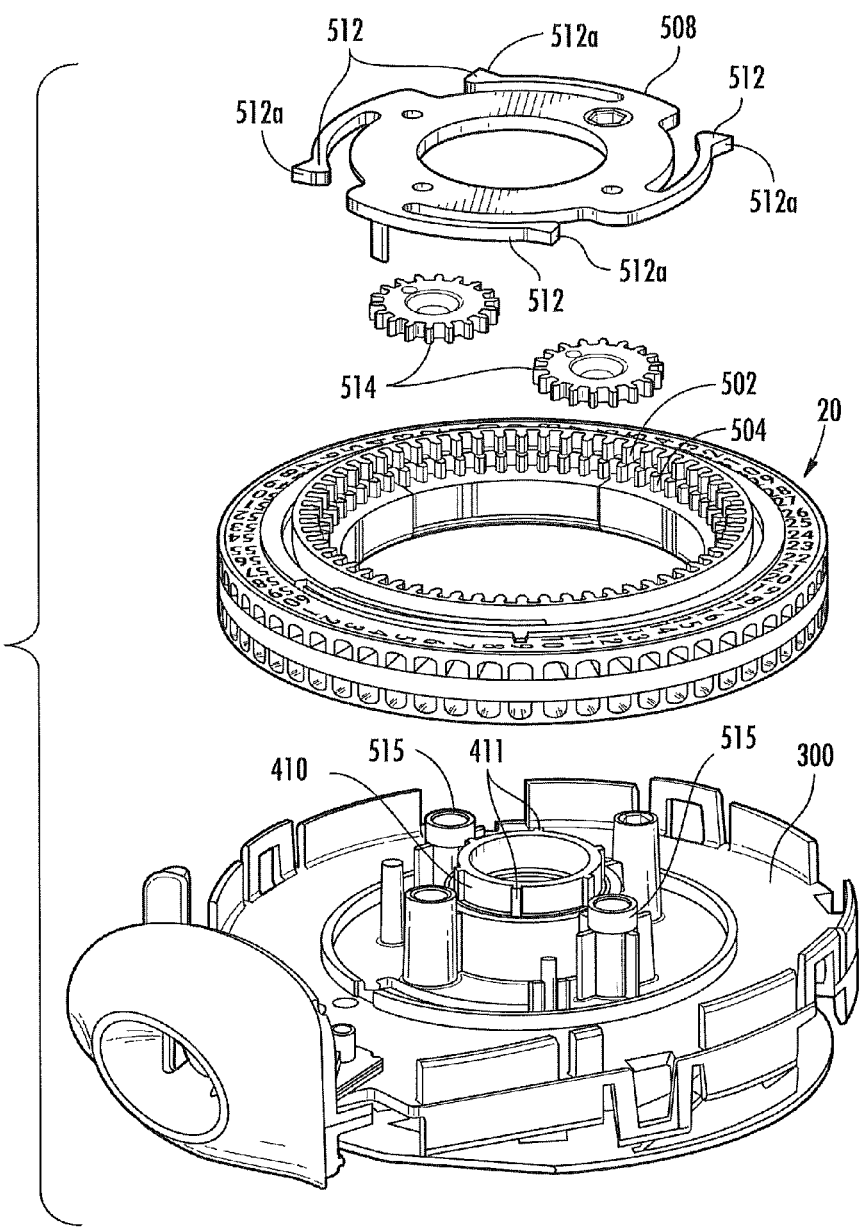
FIG. 15C is an exploded side perspective view of components of the indexing mechanism of the inhaler of FIG. 10B.

Referring to FIGS. 15B, 15C the indexing frame 508 of the inhaler 10 of FIG. 10B is secured to the piercing frame 300. A pair of idler gears 514 are rotatably secured to the piercing frame 300 and is positioned such that the teeth 516 of the idler gears 514 engage the second set of inner perimeter teeth 504 of the lower disk 40. These idler gears 514 are engaged by and caused to rotate by indexing post ribs 411. To index the dose container assembly 20 by a predetermined amount, the ramp disk 400 is rotated via user movement of the actuator mechanism 306 via user lever 320 from the first position to the second position. Rotation of the ramp disk 400 causes the indexing post 410 to rotate which, in turn, causes rotation of the idler gears 514. Rotation of the idler gears 514 rotates the dose container assembly a predetermined amount via the second set of inner perimeter teeth 504 of the lower disk 40.

FIG. 15C is an exploded side perspective view of components of the indexing mechanism of the inhaler of FIG. 10B.

Figure 17B:
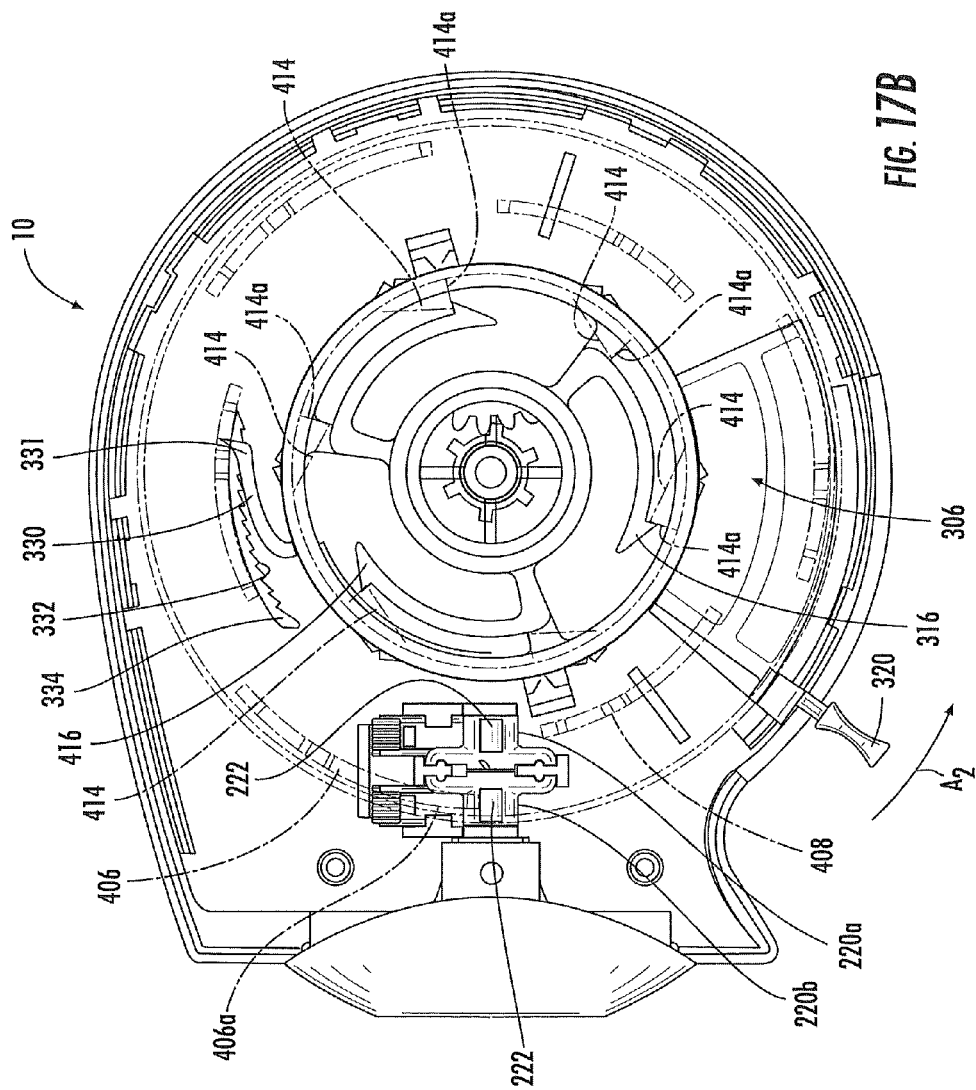

Referring now to FIGS. 17A-17E, operation of the piercing mechanism 200 of the inhaler 10 of FIG. 10A is illustrated. In FIG. 17A, a user has opened the cover 11 and the actuator mechanism is in the first position. The proximal end 222 of the inner piercing member 220a is resting on the shelf portion 408d of a ramp element 408. As such, the inner piercing member 220a is partially retracted from a dose container 30c. In FIGS. 17A-17E, the ramp disk 400 is shown in dotted line for ease of discussion and clarity.

In FIG. 17B, the user is moving the lever 320 of the actuator mechanism 306 in the direction (indicated by A$_2$) of the second position. The pawl 316 of each arcuate arm 314 of the actuator mechanism 306 is engaged with the end 414a of a respective step member 414 of the ramp disk 400. As such, movement of the actuator mechanism 306 (via lever 320) causes the ramp disk 400 to rotate along the direction indicated by arrow A$_2$. At the stage of operation illustrated in FIG. 17B, the inner piercing member 220a is fully retracted and the first inclined portion 406a of a ramp element 406 is beginning to engage the proximal end 222 of the outer piercing member 220b. Rotation of the ramp disk 400 causes the indexing post to rotate which, in turn, rotates the idler gear 514 which, in turn, indexes the dose container assembly to the next dose container 30c. Also, at the stage of operation illustrated in FIG. 17B, the pawl 331 of arm 330 is engaged with the teeth 332 of rack 334 to prevent backward movement of the actuator mechanism 306.

Figure 17C:
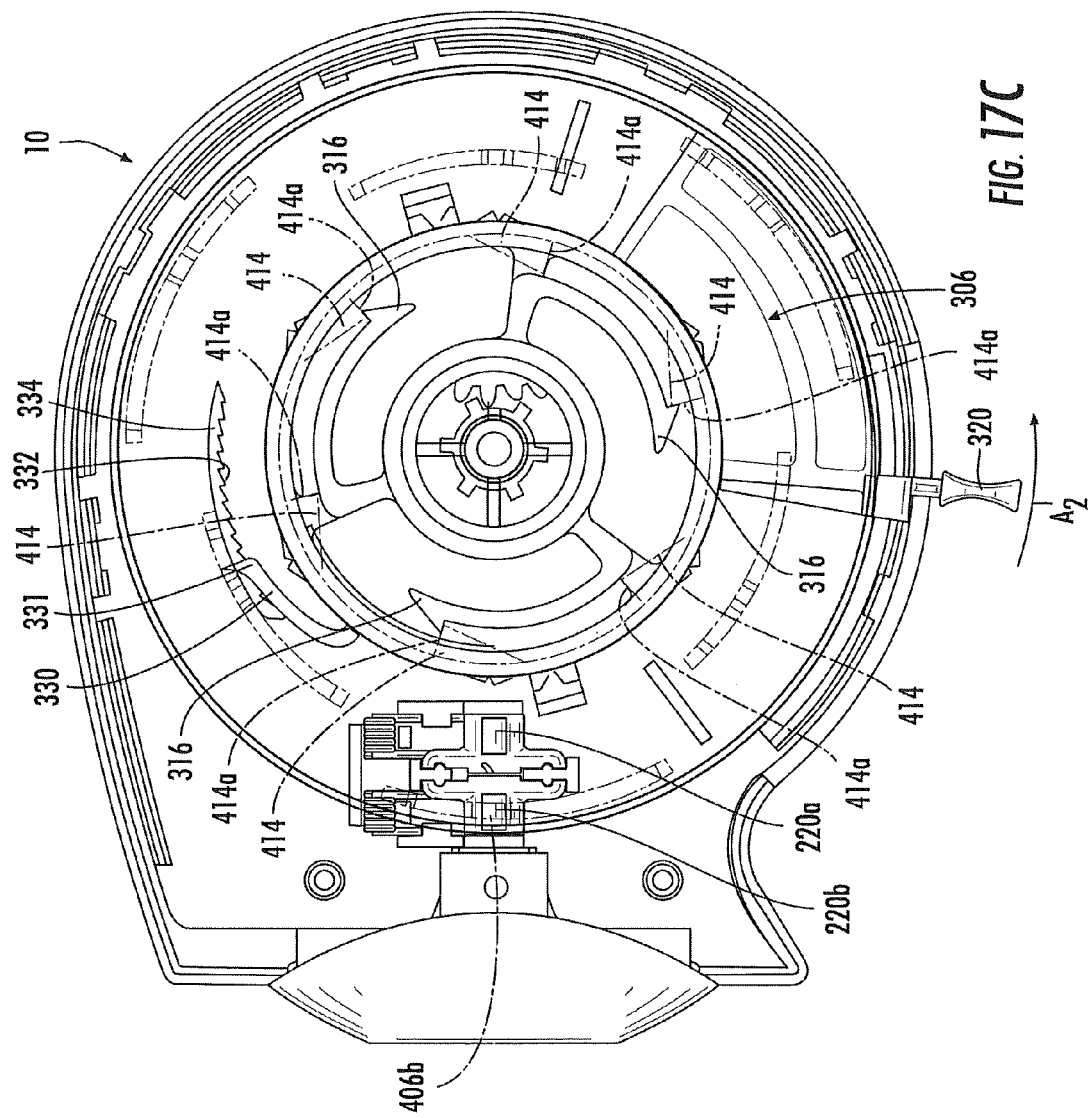

In FIG. 17C, the user has continued to move the lever 320 of the actuator mechanism 306 toward the second position, which has continued rotation of the ramp disk 400. The proximal end 222 of the outer piercing member 220b is engaged with the plateau portion 406b of the ramp element 406, such that the outer piercing member 220b is fully extended within a dose container 30c.

Figure 17D:
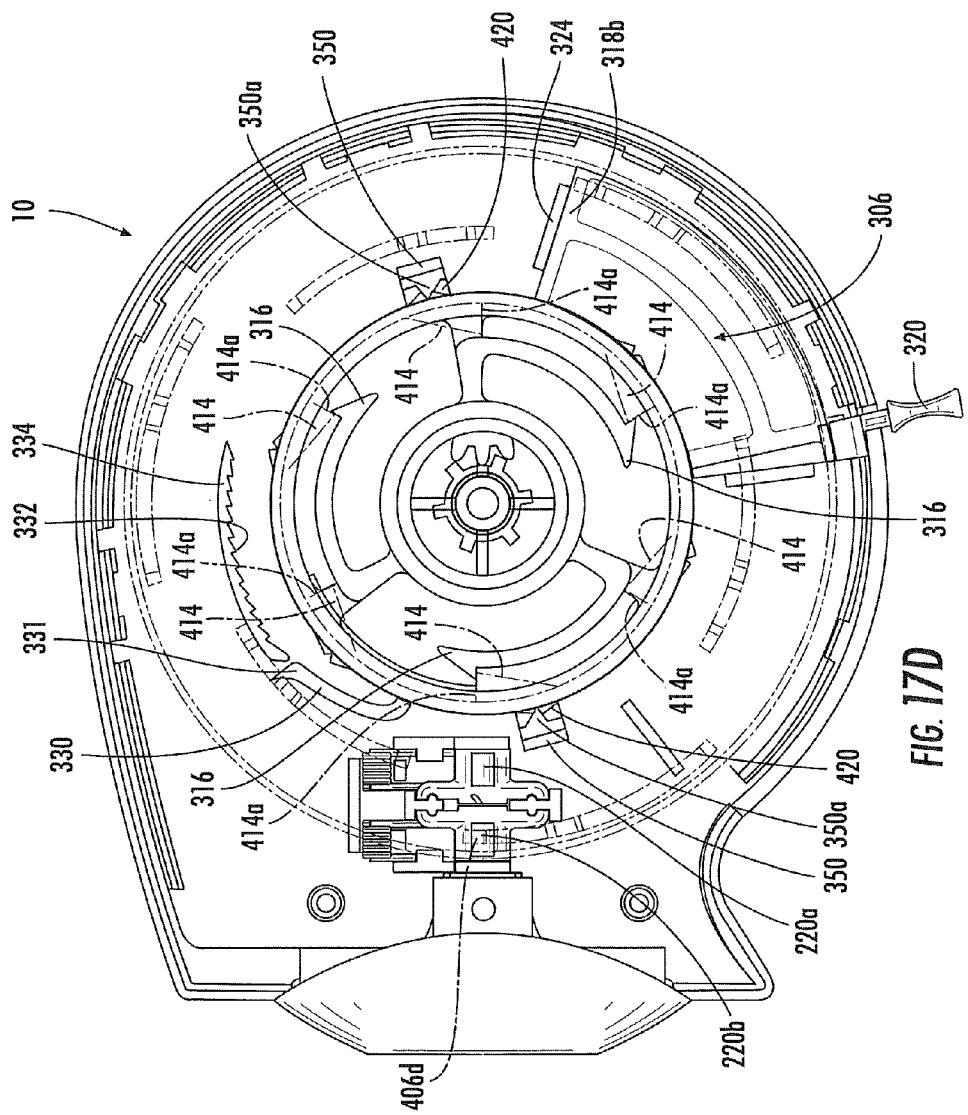

In FIG. 17D, the user has moved the lever 320 of the actuator mechanism 306 completely to the second position. As illustrated, the end 318b of the arcuate body portion 318 of the actuator mechanism 306 abuts the blocking member 324. In addition, the tooth 350a of each anti-backup post 350 is engaged with a respective catch 420 on the ramp disk 400 ring member 412 so as to prevent backwards rotation of the ramp disk 400. FIG. 17D represents the dosing position. A user at this point would inhale a dose from a pierced dose container 30c. The proximal end 222 of the outer piercing member 220b is engaged with the shelf portion 406d of the ramp element 406.

Also, in FIG. 17D, the pawl 331 has disengaged from the teeth 332 and the arm distal free end 330b has biased outwardly to a relaxed position. As the actuator mechanism 306 is returned to the first position (FIG. 17E), the arm free end 330b is configured to slide along an outside wall 336 of the rack 334 such that the pawl 331 cannot engage any of the teeth 332.

In FIG. 17E, the actuator mechanism 306 is being returned to the first position as a result of the user closing the cover 11. The ramp disk 400 does not move during the return of the actuator mechanism 306 to the first position. The tapered configuration of the distal free end 330b of arm 330 causes the pawl 331 to again be ready to engage with the teeth 332 of the rack 334 when the actuator mechanism 306 reaches the first position.

The piercing frame 300, actuator mechanism 306, ramp disk 400, piercing mechanism 200, and the various components associated therewith, may be formed from various materials including, but not limited to, polymeric materials.

Because two piercing members 220a, 220b are utilized; wear (e.g., caused by lactose in the medicament powder within the dose containers 30c) can be significantly reduced for each piercing member 220a, 220b. As such, a less expensive material may be utilized for the piercing members 220a, 220b than may otherwise be necessary if only a single piercing member were to be utilized.

In addition, because the actuator mechanism 306 and the ramp disk 400 are separate components, different materials may be utilized for each one. For example, cosmetic materials may be utilized for the user lever 320 of the actuator mechanism 306, while a less cosmetic material may be utilized for the ramp disk 400, which cannot be seen by a user of the inhaler 10.

Figure 18A:
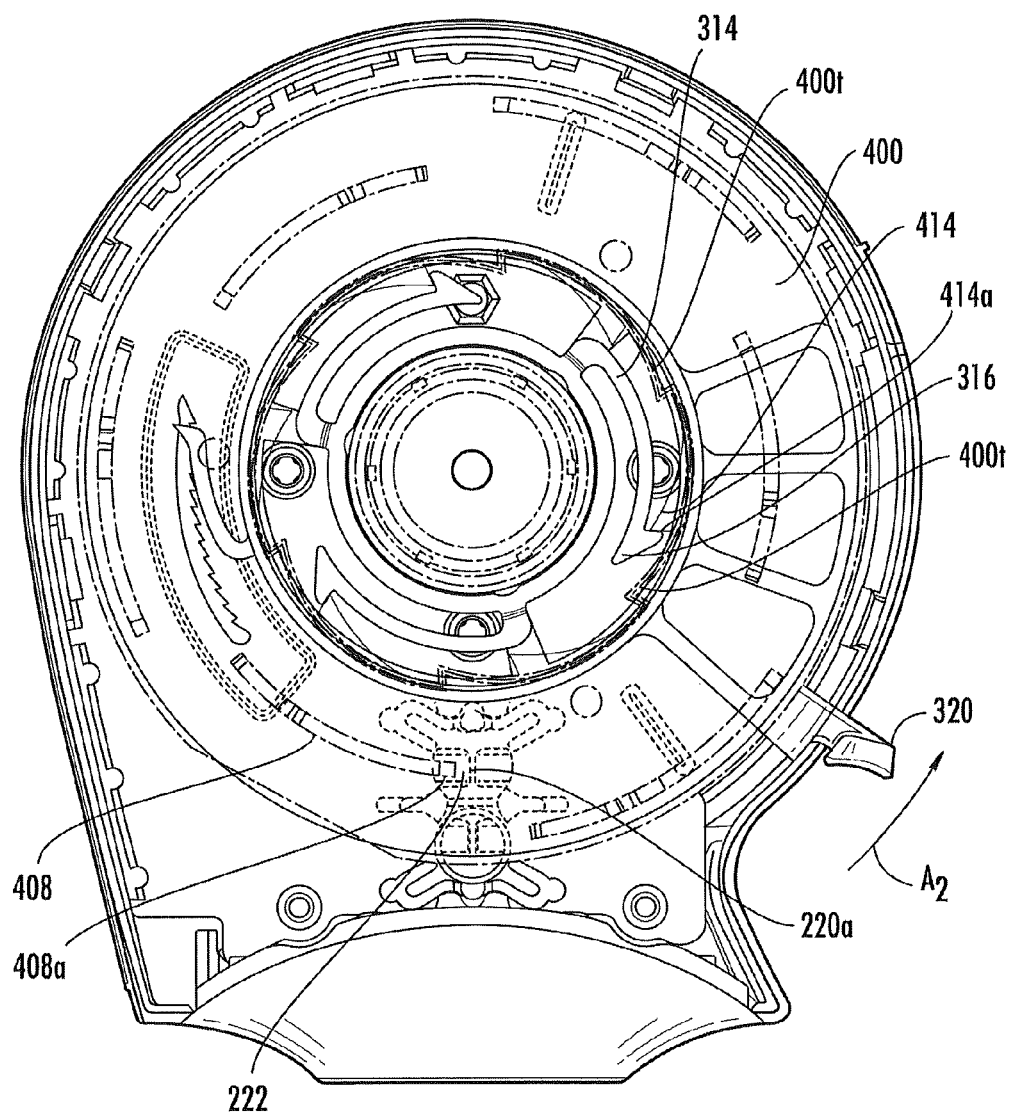
FIGS. 18A-18C are top, cutaway views, with partial transparent layers or members/disks for clarity, of the inhaler of FIG. 10B that illustrate an exemplary sequence of operations thereof, according to some embodiments of the present invention.
Figure 18B:
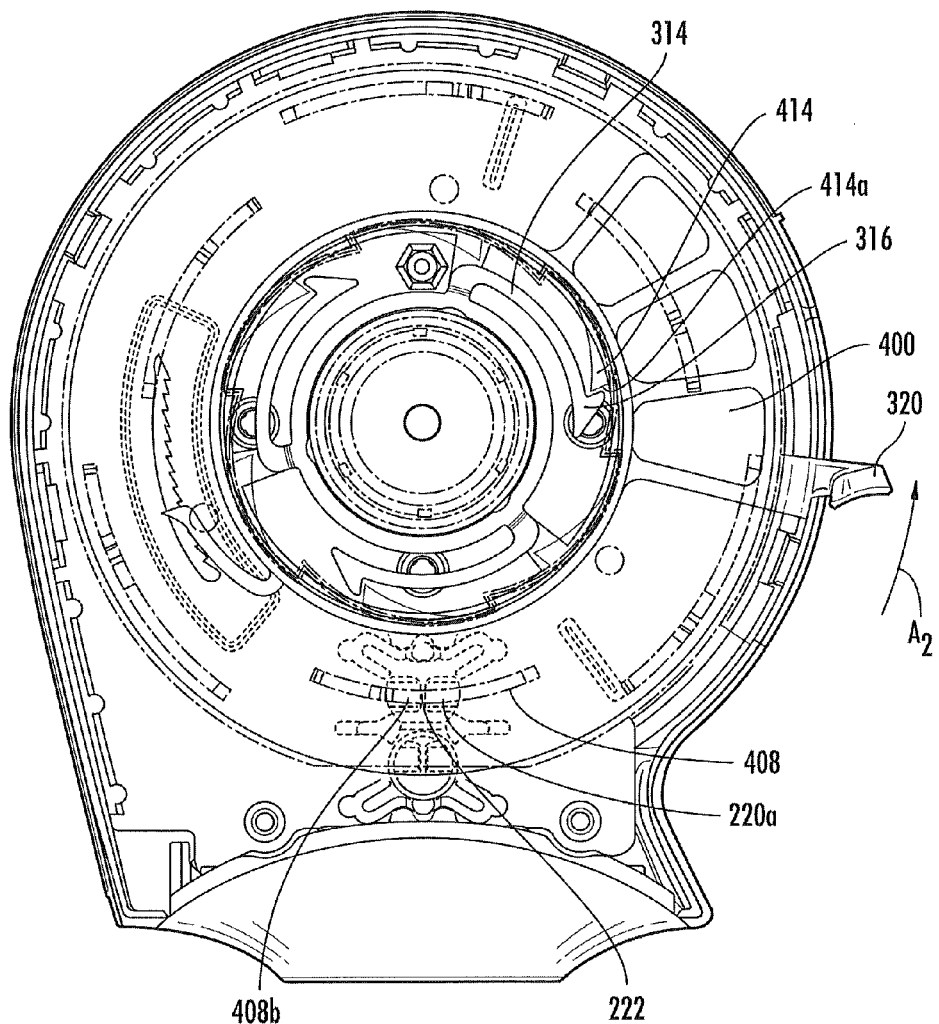
Figure 18C:
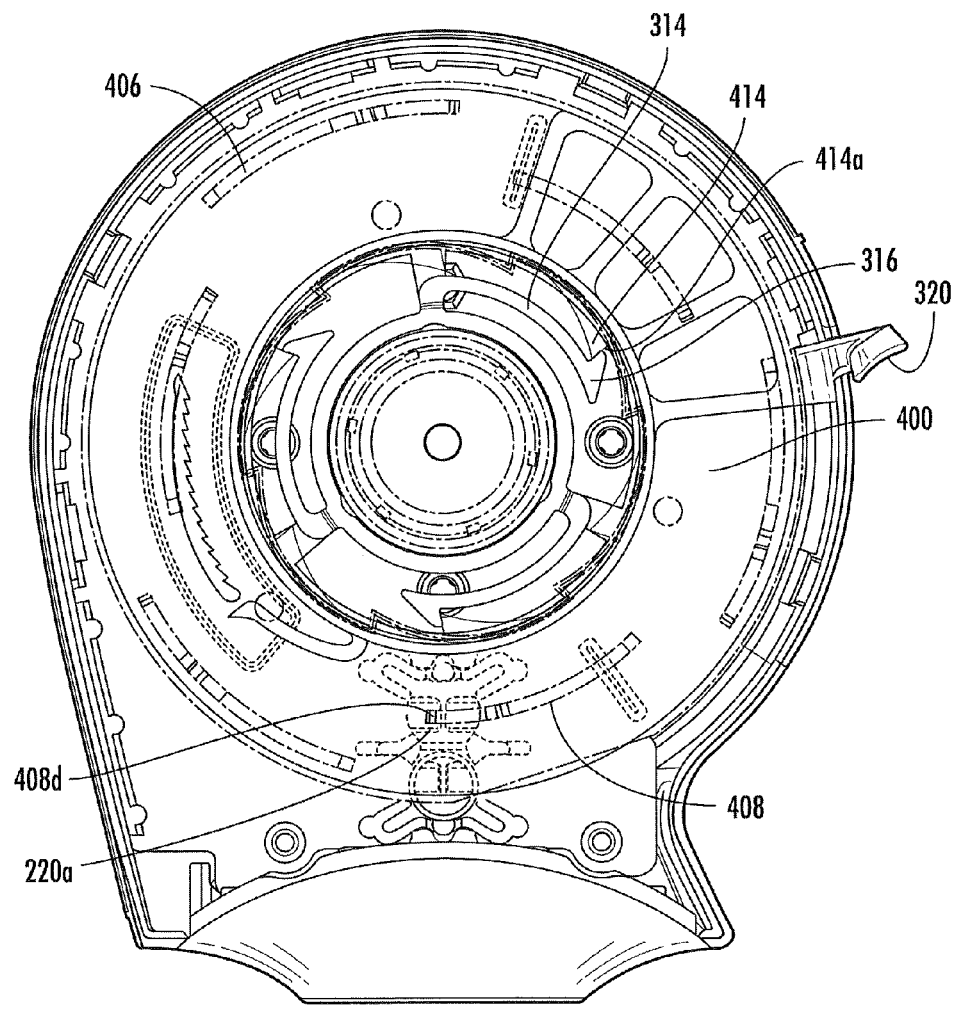

FIGS. 18A-18C are top, cutaway views, with partial transparent layers or members/disks for clarity, of the inhaler 10 of FIG. 10B that illustrate an exemplary sequence of operations thereof, according to some embodiments of the present invention. In FIG. 18A, a user is moving the lever 320 of the actuator mechanism 306 in the direction (indicated by A$_2$) from the first position to the second position, as described above. The pawl 316 of each arcuate arm 314 of the actuator mechanism 306 is engaged with the end 414a of a respective step member 414 of the ramp disk 400. As such, movement of the actuator mechanism 306 (via lever 320) causes the ramp disk 400 to rotate along the direction indicated by arrow A$_2$. At the stage of operation illustrated in FIG. 18A, the inner piercing member 220a is retracted and the first inclined portion 408a of a ramp element 408 is beginning to engage the proximal end 222 of the inner piercing member 220a. Rotation of the ramp disk 400 causes the indexing post 410 to rotate which, in turn, rotates the pair of idler gears 514 (FIG. 14C) which, in turn, indexes the dose container assembly to the next dose container 30c.

In FIG. 18B, the user has continued to move the lever 320 of the actuator mechanism 306 toward the second position, which has continued rotation of the ramp disk 400. The proximal end 222 of the inner piercing member 220a is engaged with the plateau portion 408b of the ramp element 408, such that the inner piercing member 220a is fully extended within a dose container 30c. In FIG. 18C, the user has moved the lever 320 of the actuator mechanism 306 completely to the second position. The proximal end 222 of the inner piercing member 220a is engaged with the shelf portion 408d of the ramp element 408. Also, at the stage of operation illustrated in FIG. 18A, the ratchet arms 12a in the upper housing portion 12 are cooperating with teeth 400t in the first side 402 of the ramp disk 400 to prevent backward movement of the ramp disk 400.

FIG. 19A illustrates one embodiment of a piercing mechanism 200 with a corkscrew piercing member 220. In operation the corkscrew piercing member 220 moves up and down vertically straight, typically without rotation, to create a desired opening shape (e.g., circular) through the sealant layers 36, 37. In other embodiments, the corkscrew piercing member 220 may rotate during extension and/or dispensing. In the embodiment shown, the corkscrew piercing member 220 can remain in the lower channel 41 while the dry powder is dispensed in the airflow path and the blockage of the aperture 30a can be provided by a resilient member 120 that is mounted on the corkscrew piercing member 220 and moves up and down therewith. The piercing member 220 can have a two stage operation, fully up (for indexing) and fully down. The most forward portion of the corkscrew piercing member 220 can have a point with a configuration that creates a desired cutting configuration into the sealant (e.g., foil). In some embodiments, the corkscrew piercing member 220 can cut a shape with a tab into the sealant 36, 37, then fold the tab down to release the dry powder. Positioning the corkscrew piercing member 220 in the channel 41 during dispensing may provide improved aerodynamics or shear or impaction flow turbulence for the dry powder. The resilient member 120 can comprise a foam block or other resilient member 120 (such as a hard or rigid member biased by a spring) that can be used to seal or plug the aperture 30a in disk 30.

FIG. 19B illustrates a similar corkscrew piercing member 220 that is used with a disk assembly 20 having both upper and lower airway disks 50, 40. A resilient and/or flexible member 200p such as a polymeric and/or elastomeric or foam plug can be used to occlude or seal the airway disk aperture 55. Such a resilient and/or flexible member 200p may also be used with other types of piercing members (e.g., solid piercing members, fluted piercing members, etc.

FIGS. 19C and 19D illustrate a piercing mechanism 200 with a fluted solid piercing member 220. The flute may have a straight flute configuration or the flute can have a twist or partial twist along it length, e.g., the maxima and minima of the lobes change axially along the length of the flute. The flute can have a cross section with a plurality of lobes, typically three or four lobes, shown as three lobes in FIGS. 19C and 19D, and as four lobes in FIG. 19F. The fluted configuration may extend only a partial forward length and merge into a constant diameter segment that resides in and helps occlude or seal the aperture 55 as shown in FIG. 19E. In other embodiments, the solid or fluted piercer configuration can merge into a cap or plug that resides over and/or in the aperture 55. In some embodiments, the twisted flute piercing member 220 can remain in the lower disk 40 during dispensing which may facilitate turbulence and/or compaction in the airway.

FIG. 19D illustrates that the fluted piercing member 220 can rotate as it pierces the foil or other sealant material to form a round hole or may be extended straight without rotation. In other embodiments, the fluted piercer 220 can be extended or advanced without rotation to pierce the sealant layer(s) 36, 37. FIG. 19E illustrates that the fluted piercing member 220' can include a fluted forward portion 220f with a length "$L_1$" that merges into a solid portion 112 that can have a substantially circular cross-section with a length "$L_2$". $L_1$ is typically longer than $L_2$. $L_1$ can have a length sufficient to allow the forward fluted portion 220f to reside in the dose container aperture 30a (typically just below the lower sealant line or in-line with or slightly above or below the lower surface of the disk 30) and/or through the lower sealant 37 at the same time, with the solid portion engaging the airway disk aperture 55.

The inhaler 10 can have a body that is a portable, relatively compact "pocket-sized" configuration. In some embodiments, the inhaler body can have a width/length that is less than about 115 mm (about 4.5 inches), typically less than about 89 mm (about 3.5 inches), and a thickness/depth of less than about 51 mm (about 2 inches), typically less than about 38 mm (about 1.5 inches). The inhaler body can also be configured to be generally planar on opposing primary surfaces to facilitate pocket storage.

The inhaler can include a circuit that can control certain operations of the inhaler 10. The inhaler 10 can include a computer port (not shown). The port may be, for example, an RS 232 port, an infrared data association (IrDA) or universal serial bus (USB), which may be used to download or upload selected data from/to the inhaler to a computer application or remote computer, such as a clinician or other site. The inhaler 10 can be configured to via a wired or wireless communication link (one-way or two-way) to be able to communicate with a clinician or pharmacy for reorders of medicines and/or patient compliance. The inhaler 10 may also include a second peripheral device communication port (not shown). The inhaler 10 may be able to communicate via the Internet, telephone, cell phone or other electronic communication protocol.

In some embodiments, the circuit can include computer program code and/or computer applications that communicate additional data to a user (optionally to the display) as noted above and/or communicate with another remote device (the term "remote" including communicating with devices that are local but typically not connected during normal inhalant use).

In some embodiments, the circuit can be in communication with a vibrator device (not shown). The vibrator device can be any suitable vibrator mechanism. The vibrator device can be configured to vibrate the dry powder in the airflow path. In some embodiments, the vibrator device can comprise a transducer that is configured to vibrate the opened cartridge(s) holding the dry powder. Examples of vibrator devices include, but are not limited to, one or more of: (a) ultrasound or other acoustic or sound-based sources (above, below or at audible wavelengths) that can be used to instantaneously apply non-linear pressure signals onto the dry powder; (b) electrical or mechanical vibration of the walls (sidewalls, ceiling and/or floor) of the inhalation flow channel, which can include magnetically induced vibrations and/or deflections (which can use electromagnets or permanent field magnets); (c) solenoids, piezoelectrically active portions and the like; and (d) oscillating or pulsed gas (airstreams), which can introduce changes in one or more of volume flow, linear velocity, and/or pressure. Examples of mechanical and/or electro-mechanical vibratory devices are described in U.S. Pat. Nos. 5,727,607, 5,909,829 and 5,947,169, the contents of which are incorporated by reference as if recited in full herein. Combinations of different vibrating mechanism's can also be used.

In some embodiments, the vibrator device can include a commercially available miniature transducer from Star Micronics (Shizuoka, Japan), having part number QMB-105PX. The transducer can have resonant frequencies in the range of between about 400-600 Hz.

In certain embodiments, the inhaler 10 can include visible indicia (flashing light or display "error" or alert) and/or can be configured to provide audible alerts to warn a user that a dose was properly (and/or improperly) inhaled or released from the inhaler. For example, certain dry powder dose sizes are formulated so that it can be difficult for a user to know whether they have inhaled the medicament (typically the dose is aerosolized and enters the body with little or no taste and/or tactile feel for confirmation). Thus, a sensor (not shown) can be positioned in communication with the flow path in an inhaler and configured to be in communication with a digital signal processor or microcontroller, each held in or on the inhaler. In operation, the sensor can be configured to detect a selected parameter, such as a difference in weight, a density in the exiting aerosol formulation, and the like, to confirm that the dose was released.

The sealed dose containers 30c can be configured so that the water vapor transmission rate can be less than about 1.0 g/100 in$^2$/24 hours, typically less than about 0.6 g/100 in$^2$/24 hours and an oxygen transmission rate that is suitable for the dry powder held therein. The dose container assemblies 20, 20' can be configured with a stable shelf life of between about 1-5 years, typically about 4 years.

The dose containers 30c can have a volume (prior to filling and sealing) that is less than about 24 mm$^3$, typically between 5-15 mm$^3$. The powder bulk density can be about 1 g/cm$^3$ while the power nominal density when filled (for reference)

can be about 0.5 g/cm$^3$. The maximum compression of a drug by filling and sealing in the dose container 30c can be less than about 5%, typically less than about 2%. The maximum heating of drug during the filling and sealing can be maintained to a desirable level so as not to affect the efficacy of the drug or the formulation.

Figure 20:
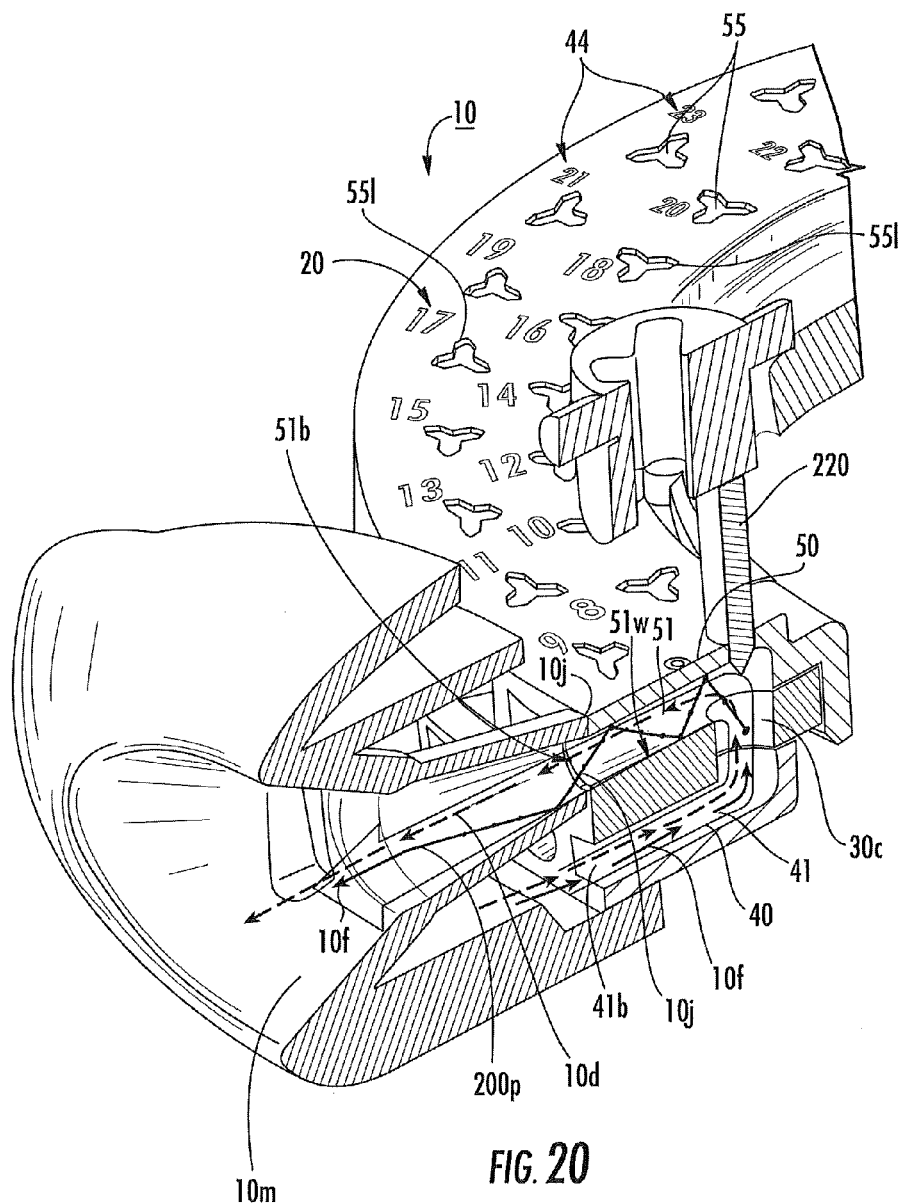
FIG. 20 is an enlarged partial section view of an inhaler having generally "U" shaped inhalation flow paths for each dose according to embodiments of the present invention.

FIG. 20 illustrates the substantially U-shaped airpaths created by the disk assembly 20 (e.g., the upper disk channel 51 and lower disk channel 41 define the long sides of the "U" which extend in a radial direction across the disk body. As shown, in this embodiment, the outer perimeter of the disk assembly 20 holds both the outlet and an inlet for the airflow path 10f. The "U" shaped flow path (or, in some embodiment, a partial "U" where only a one of the airflow disks 40, 50 is used) can function as a powder deagglomerator. The dry powder particles 10d impact the opposing wall of the airway disk channel 51 as they exit the dose container 30c with sufficient force to deagglomerate the drug powder.

FIG. 20 also illustrates an example of dry powder particle trajectories 10d entrained in air flow associated with the inspiratory airflow path 10f. After the dry powder exits the dose container 30c in the airflow path 10f, the air flow and smaller powder particles (10f) in the air are able to make the about 90 degree turn while heavier dry powder particles (10d) bounce off the inner wall 51w of the upper airway disk channel 51 with increasingly shallow angles eventually going more or less straight out of the mouthpiece 10m, The impact of the heavier dry powder against the inner wall 51w helps deagglomerate the dry powder. Referring again to FIG. 5A, in the dual row dose container 30 embodiment, the channels 51 vary in length depending on if the dose container 30 is on the inner or outer row.

In some particular embodiments, the airway channels 41, 51 can include alternating short and long channels (see, e.g., FIG. 5A). The length of the long channel (the channels with the dose container on the inner perimeter where the outer perimeter is the exit location and vice versa if the inner perimeter is the exit location) can between about 5 mm to about 15 mm, typically about 10 mm, the length of the short channel can be between about 3-10 mm, typically about 5 mm (e.g., about 40-70% the length of the long channel. The depth (vertical height) of each channel 41, 51 can be the same or can, in some embodiments vary. Exemplary depths of the channels 41, 51 are between about 1 mm to about 3 mm, typically about 2 mm, but other depths can be used.

Certain embodiments may be particularly suitable for dispensing medication to respiratory patients, diabetic patients, cystic fibrosis patients, or for treating pain. The inhalers may also be used to dispense narcotics, hormones and/or infertility treatments.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the teachings and advantages of this invention. Accordingly, all such modifications are intended to be included within the scope of this invention as defined in the claims. The invention is defined by the following claims, with equivalents of the claims to be included therein.

That which is claimed is:

1. A dry powder inhaler, comprising:
    a dose container disk having a plurality of circumferentially spaced apart dry powder dose containers arranged in first and second concentric rows of different radius; and
    a piercing mechanism configured to sequentially open a dry powder dose container on the first row then open a dry powder dose container on the second row multiple times to dispense dry powder for inhalation.

2. The dry powder inhaler of claim 1, wherein the piercing mechanism comprises:
    first and second elongate piercing members in adjacent radially spaced-apart relationship, wherein each piercing member is capable of reciprocal movement between piercing and non-piercing positions, wherein each piercing member includes a distal piercing portion and a proximal head portion, wherein the first piercing member is configured to pierce the sealant of a dose container in the first row, and wherein the second piercing member is configured to pierce the sealant of a dose container in the second row.

3. The dry powder inhaler of claim 2, wherein the piercing mechanism comprises a biasing member configured to urge each piercing member toward a retracted position.

4. The dry powder inhaler of claim 2, further comprising a rotatable ramp disk that comprises first and second sets of circumferentially spaced-apart ramp elements in staggered, concentric relationship, wherein the first set of ramp elements move the first piercing member between retracted and extended positions, and wherein the second set of ramp elements move the second piercing member between retracted and extended positions.

5. The dry powder inhaler of claim 4, wherein each ramp element in the first and second sets comprises a first inclined portion, a plateau portion, a second inclined portion, and a shelf portion.

6. The dry powder inhaler of claim 4, further comprising an actuator that is movable between first and second positions, wherein the dose container disk has a sealant over an upper primary surface thereof and a sealant over a lower primary surface thereof, wherein movement of the actuator from the first position to the second position causes the ramp disk to rotate such that a ramp element in the first set causes the first piercing member to pierce the sealants over and under a dose container in the first row.

7. The dry powder inhaler of claim 6, wherein subsequent movement of the actuator from the first position to the second position causes the ramp disk to rotate such that a ramp element in the second set causes the second piercing member to pierce the sealants over and under a dose container in the second row.

8. The dry powder inhaler of claim 4, further comprising an actuator that is movable between first and second positions, wherein the dose container disk has a sealant over an upper primary surface thereof and a sealant over a lower primary surface thereof, wherein movement of the actuator from the first position to the second position causes rotation of the ramp disk which causes one of the first or second piercing members to pierce the sealants over and under a dose container, and then partially retract therefrom.

9. The dry powder inhaler of claim 2, wherein each piercing member comprises a corkscrew piercer configured to pierce the sealant with a straight vertical non-rotational movement.

10. The dry powder inhaler of claim 2, wherein each piercing member comprises a fluted piercer configured to pierce the sealant.

11. The dry powder inhaler of claim 10, wherein the fluted piercer comprises three or four lobes.

12. The dry powder inhaler of claim 1, further comprising:
    a housing, wherein the dose container disk is rotatably secured within the housing, wherein the dose container disk has opposing upper and lower primary surfaces, a first row of circumferentially spaced apart apertures associated with dose containers at a first radius and a second row of circumferentially spaced apart apertures associated with dose containers at a second radius so that the first and second rows are concentric with respect to a center of the disk, wherein the dose containers have dry powder therein; and a flexible sealant residing over at least one of the dose container disk upper and lower primary surfaces;

wherein the piercing mechanism is operably associated with the dose container disk and is configured to pierce the sealant of a dose container in the first row, then pierce the sealant of a dose container in the second row.

13. The dry powder inhaler of claim 1, further comprising an actuator that is movable between first and second positions, wherein movement of the actuator from the first position to the second position causes the dose container disk to sealably engage an interface or wall associated with an exit airflow path in the inhaler.

14. The dry powder inhaler of claim 13, wherein the actuator comprises a biasing post, and wherein movement of the actuator from the first position to the second position causes the biasing post to urge the dose container disk to sealably engage an interface or wall associated with an exit airflow path in the inhaler.

15. The dry powder inhaler of claim 1, wherein the first row of dose container apertures have centerlines that are circumferentially spaced apart from centerlines of the second row of dose containers.

16. The dry powder inhaler of claim 1, wherein there are 30 dose container apertures in the first row and 30 dose container apertures in the second row.

17. The dry powder inhaler of claim 1, wherein each dose container comprises a dry powder having a pharmaceutically active agent selected from the group consisting of bronchodilators, inhaled corticosteroids (ICS), and anticholinergics.

18. The dry powder inhaler of claim 1, wherein each dose container comprises a dry powder having a pharmaceutically active agent, and wherein the agent comprises one or more of the following bronchodilators:

albuterol, salmeterol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol, or (−)-4-amino-3, 5-dichloro-α-[[6-[2-(2-pyridinyl)ethoxy]hexyl] methyl] benzenemethanol;

wherein the bronchodilator may be used in the form of salts, esters or solvates to thereby optimize the activity and/or stability of the medicament.

19. The dry powder inhaler of claim 1, wherein each dose container comprises a dry powder having a pharmaceutically active agent, and wherein the agent comprises one or more of the following inhaled corticosteroids: beclomethasone dipropionate, fluticasone propionate, flunisolide, budesonide, mometasone furoate, and triamcinolone acetonide.

20. The dry powder inhaler of claim 1, wherein each dose container comprises a dry powder having a pharmaceutically active agent, and wherein the agent comprises one or more of the following anticholinergics:

ipratropium, tiotropium, atropine, and oxitropium.

* * * * *

UNITED STATES PATENT AND TRADEMARK OFFICE
CERTIFICATE OF CORRECTION

PATENT NO. : 8,985,103 B2
APPLICATION NO. : 13/744923
DATED : March 24, 2015
INVENTOR(S) : Thoe et al.

Page 1 of 1

It is certified that error appears in the above-identified patent and that said Letters Patent is hereby corrected as shown below:

In the specification,

Column 18, Line 53: Please correct "between .respective"
to read -- between respective --

Column 29, Line 16: Please correct "members, etc."
to read -- members, etc.). --

Signed and Sealed this
Twelfth Day of January, 2016

Michelle K. Lee
*Director of the United States Patent and Trademark Office*